US012807723B2

(12) United States Patent
Chen et al.

(10) Patent No.: US 12,807,723 B2
(45) Date of Patent: Nov. 24, 2026

(54) ANTIBODIES BINDING IL6R AND USES THEREOF

(71) Applicant: BIOSION INC., Nanjing (CN)

(72) Inventors: Mingjiu Chen, Nanjing (CN); Shukai Xia, Nanjing (CN)

(73) Assignee: BIOSION INC., Nanjing (CN)

( * ) Notice: Subject to any disclaimer, the term of this patent is extended or adjusted under 35 U.S.C. 154(b) by 868 days.

(21) Appl. No.: 17/997,583

(22) PCT Filed: May 17, 2021

(86) PCT No.: PCT/CN2021/094107
§ 371 (c)(1),
(2) Date: Oct. 31, 2022

(87) PCT Pub. No.: WO2021/233246
PCT Pub. Date: Nov. 25, 2021

(65) Prior Publication Data

US 2023/0167182 A1 Jun. 1, 2023

Related U.S. Application Data

(60) Provisional application No. 63/026,274, filed on May 18, 2020.

(51) Int. Cl.
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/24* (2013.01); (Continued)

(58) Field of Classification Search
None
See application file for complete search history.

(56) References Cited

U.S. PATENT DOCUMENTS 5,795,965 A 8/1998 Tsuchiya et al.
8,753,634 B2 6/2014 Lee et al.
(Continued)

FOREIGN PATENT DOCUMENTS

CN 110114370 A 8/2019
CN 110483640 B 5/2020
(Continued)

OTHER PUBLICATIONS

JPO, Office Action issued on Oct. 3, 2023 to counterpart JP Application No. 2022-569148.
(Continued)

*Primary Examiner* — Aurora M Fontainhas
*Assistant Examiner* — Selam Berhane
(74) *Attorney, Agent, or Firm* — Duane Morris LLP; Thomas J. Kowalski

(57) ABSTRACT

An isolated monoclonal antibody that specifically binds human IL6R, or an antigen-binding portion thereof is provided. A nucleic acid molecule encoding the antibody or the antigen-binding portion thereof, an expression vector, a host cell and a method for expressing the antibody or the antigen-binding portion thereof are also provided. Further provided is a bispecific molecule, an immunoconjugate, a chimeric antigen receptor, an oncolytic virus and a pharmaceutical composition comprising the antibody or the antigen-binding portion thereof, as well as a treatment method using an Anti-IL6R antibody or the antigen-binding portion thereof.

18 Claims, 18 Drawing Sheets

Specification includes a Sequence Listing.

| | mouse 1F7 | mouse 1D4 | Actemra |
|---|---|---|---|
| EC50 | 0.05935 | 0.05584 | 0.2205 |

| | mouse 1A3 | mouse 1G8 | mouse 1B5 | Actemra |
|---|---|---|---|---|
| EC50 | 0.07295 | 0.05018 | 0.03721 | 0.21 |

(52) U.S. Cl.
CPC .... *C07K 2317/52* (2013.01); *C07K 2317/565* (2013.01); *C07K 2317/76* (2013.01)

(56) References Cited

U.S. PATENT DOCUMENTS

| | | | |
|---|---|---|---|
| 9,017,678 | B1 | 4/2015 | Clube |
| 2013/0157313 | A1 | 6/2013 | Stevens et al. |

FOREIGN PATENT DOCUMENTS

| | | | |
|---|---|---|---|
| JP | 2016530495 | A | 9/2016 |
| WO | 2007143168 | A2 | 12/2007 |
| WO | 2019052457 | A1 | 3/2019 |

OTHER PUBLICATIONS

CNIPA, Office Action issued on May 16, 2025 to counterpart CN Application No. 202180035889.5.
KIPO, Office Action issued on Aug. 20, 2025 to counterpart KR Application No. 10-2022-7043558.
EPO, Supplementary European Search Report and Written Opinion issued on Apr. 30, 2024 to counterpart EP Application No. 21808161.
S. J. Jiang, et al., Research progress on IL-6 / IL-6 receptor axis and its targeted inhibitors, Chinese Journal of Cellular and Molecular Immunology (Dec. 31, 2019) vol. 35, No. 6, p. 569-574.
T. Kishimoto, Discovery of IL-6 and Development of Anti-IL-6R Antibody, The Keio Journal Of Medicine (Dec. 31, 2019) vol. 68, No. 4.
M. Sheppard, et al., Tocilizumab (Actemra) Human Vaccines & Immunotherapeutics (Dec. 31, 2017) vol. 13, No. 9, p. 1972-1988.
International Search Report issued Aug. 20, 2021 in International Application No. PCT/CN2021/094107.

| | mouse 1F7 | mouse 1D4 | Actemra |
|---|---|---|---|
| EC50 | 0.05935 | 0.05584 | 0.2205 |

| | mouse 1A3 | mouse 1G8 | mouse 1B5 | Actemra |
|---|---|---|---|---|
| EC50 | 0.07295 | 0.05018 | 0.03721 | 0.21 |

| | mouse 3C2 | mouse 1G1 | Actemra |
|---|---|---|---|
| EC50 | 0.05364 | 0.08503 | 0.2213 |

| | mouse 1H9 | mouse 1H7 | Actemra |
|---|---|---|---|
| EC50 | 0.06789 | 0.04358 | 0.1986 |

| | mouse 1H7 | mouse 1F7 | mouse 1B5 | mouse 3C2 | Actemra |
|---|---|---|---|---|---|
| EC50 | 0.2126 | 0.1404 | 0.2051 | 0.2961 | 0.05706 |

| | mouse 1A3 | mouse 1D4 | mouse 1G8 | Actemra |
|---|---|---|---|---|
| EC50 | 0.2276 | 0.1749 | 0.2321 | 0.05886 |

| | mouse 1H9 | mouse 1G1 | Actemra |
|---|---|---|---|
| EC50 | 0.3405 | 0.5013 | 0.0575 |

| | mouse 1F7 | mouse 1D4 | Actemra |
|---|---|---|---|
| EC50 | 0.3043 | 0.2739 | 1.644 |

| | mouse 1A3 | mouse 1G8 | mouse 1B5 | Actemra |
|---|---|---|---|---|
| EC50 | 0.2288 | 0.2579 | 0.204 | 1.702 |

| | mouse 3C2 | mouse 1G1 | Actemra |
|---|---|---|---|
| EC50 | 0.2861 | 0.3395 | 1.492 |

| | mouse 1H9 | mouse 1H7 | Actemra |
|---|---|---|---|
| EC50 | 0.3908 | 0.2461 | 2.103 |

| | mouse 1F7 | mouse 1D4 | Actemra |
|---|---|---|---|
| IC50 | 0.6166 | 0.9567 | 2.303 |

| | mouse 1A3 | mouse 1G8 | mouse 1B5 | Actemra |
|---|---|---|---|---|
| IC50 | 0.8074 | 0.9708 | 0.6968 | 2.332 |

| | mouse 3C2 | mouse 1G1 | Actemra |
|---|---|---|---|
| IC50 | 0.7036 | ~ 1.442 | 2.512 |

| | mouse 1H9 | mouse 1H7 | Actemra |
|---|---|---|---|
| IC50 | 1.055 | 0.6013 | 2.544 |

| | mouse 1F7 | mouse 1D4 | Actemra |
|---|---|---|---|
| IC50 | 0.311 | 0.4665 | 2.58 |

| | mouse 1A3 | mouse 1G8 | mouse 1B5 | Actemra |
|---|---|---|---|---|
| IC50 | 0.1655 | 0.1623 | 0.1615 | 1.409 |

| | mouse 3C2 | mouse 1G1 | Actemra |
|---|---|---|---|
| IC50 | 0.7078 | 0.4814 | 2.228 |

| | mouse 1H9 | mouse 1H7 | Actemra |
|---|---|---|---|
| IC50 | 0.3231 | 0.1054 | 1.584 |

| | mouse 1F7 | mouse 1G1 | Actemra |
|---|---|---|---|
| IC50 | 1.414 | 2.508 | 0.4545 |

| | mouse 1D4 | mouse 1H9 | Actemra |
|---|---|---|---|
| IC50 | 1.167 | 1.647 | 0.6044 |

| | mouse 1A3 | mouse 1B5 | Actemra |
|---|---|---|---|
| IC50 | 1.24 | 1.355 | 1.278 |

| | mouse 1G8 | mouse 1H7 | Actemra |
|---|---|---|---|
| IC50 | 0.7297 | 0.6796 | 0.3628 |

| | mouse 3C2 | Actemra |
|---|---|---|
| IC50 | 5.296 | 0.4223 |

| | mouse 1B5 | chimeric 1B5 | mouse 1H7 | chimeric 1H7 | Actemra |
|---|---|---|---|---|---|
| EC50 | 0.06269 | 0.1013 | 0.05533 | 0.07795 | 0.1907 |

| | mouse 1H9 | chimeric 1H9 | Actemra |
|---|---|---|---|
| EC50 | 0.08342 | 0.08971 | 0.1802 |

| | mouse 1B5 | chimeric 1B5 | mouse 1H7 | chimeric 1H7 | Actemra |
|---|---|---|---|---|---|
| IC50 | 0.2811 | 0.2995 | 0.2305 | 0.2612 | 0.7734 |

| | mouse 1H9 | chimeric 1H9 | Actemra |
|---|---|---|---|
| IC50 | 0.2737 | 0.2133 | 0.6161 |

| | mouse 1B5 | chimeric1B5 | mouse 1H7 | chimeric 1H7 | Actemra |
|---|---|---|---|---|---|
| IC50 | 0.2295 | 0.3168 | 0.1865 | 0.1939 | 0.8123 |

| | mouse 1H9 | chimeric 1H9 | Actemra |
|---|---|---|---|
| IC50 | 0.3935 | 0.3377 | 0.7696 |

| | mouse 1H7 | chimeric 1H7 | mouse 1B5 |
|---|---|---|---|
| IC50 | 0.3784 | 0.4507 | 0.6192 |

| chimeric 1B5 | mouse 1H9 | chimeric 1H9 | Actemra |
|---|---|---|---|
| 0.8416 | 0.8442 | 0.6288 | 0.5973 |

| | mouse 1H7 | chimeric 1H7 | hu1H7-V5 | Actemra |
|---|---|---|---|---|
| EC50 | 0.1639 | 0.2008 | 0.3102 | 0.5036 |

| | mouse 1H7 | chimeric 1H7 | hu1H7-V5 | Actemra |
|---|---|---|---|---|
| EC50 | 0.1471 | 0.2266 | 0.2421 | 0.2009 |

| | mouse 1H7 | chimeric 1H7 | hu1H7-V5 | Actemra |
|---|---|---|---|---|
| EC50 | 0.3008 | 0.298 | 0.4169 | 1.762 |

| | mouse 1H7 | chimeric 1H7 | hu1H7-V5 | Actemra |
|---|---|---|---|---|
| IC50 | 0.1892 | 0.1613 | 0.223 | 1.027 |

| | mouse 1H7 | chimeric 1H7 | hu1H7-V5 | Actemra |
|---|---|---|---|---|
| IC50 | 0.2375 | 0.2027 | 0.3639 | 0.8622 |

| | chimeric 1H7 | hu1H7-V5 | Actemra |
|---|---|---|---|
| IC50 | 0.4091 | 0.9457 | 1.224 |

ANTIBODIES BINDING IL6R AND USES THEREOF

RELATED APPLICATIONS AND INCORPORATION BY REFERENCE

This application claims priority to U.S. provisional patent application Ser. No. 63/026,274 filed May 18, 2020.

All documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing, which has been submitted electronically and is hereby incorporated by reference in its entirety. Said ASCII copy, created on Sep. 12, 2025 and revised on May 7, 2026, is named 55532-00066_ST25.txt and is 64,204 bytes in size.

FIELD OF THE INVENTION

The present disclosure relates generally to an isolated monoclonal antibody, particularly a mouse, chimeric or humanized monoclonal antibody, or an antigen-binding portion thereof, that binds to human IL6R, with high affinity and functionality. A nucleic acid molecule encoding the antibody or the antigen-binding portion thereof, an expression vector, a host cell and a method for expressing the antibody or the antigen-binding portion thereof are also provided. The present disclosure further provides a bispecific molecule, an immunoconjugate, a chimeric antigen receptor, an oncolytic virus, and a pharmaceutical composition which may comprise the antibody or the antigen-binding portion thereof, as well as a diagnostic or treatment method using the anti-IL6R antibody or antigen-binding portion thereof of the disclosure.

BACKGROUND OF THE INVENTION

Interleukin-6 (IL6) is a multifunctional cytokine, playing roles in, e.g., immunity and metabolism, through interaction with two transmembrane proteins, IL6R (also known as IL6Rα, gp80 or CD126) and gp130 (Kang, S et al., (2019) *Immunity* 50(4): 1007-1023).

IL6R expression is restricted to hepatocytes, monocytes and lymphocytes, and two forms of IL6R have been found to participate in IL6 signaling, i.e., the membrane bound IL6R (mIL6R) and the soluble IL6R (sIL6R). The sIL6R is cleaved from the mIL6R by proteases or translated from an alternatively spliced IL6R mRNA (Riethmueller, S et al., (2017) *Plos Biology* 15(1): e2000080; Lust, J. A et al., (1992) *Cytokine* 4(2): 96-100). The presence of two IL6R forms plus gp30's ubiquitous expression enables IL6 to exert its activity in various systems and organs. In specific, IL6 binds to the mIL6R and membrane bound gp130 (mgp130) to initiate classic IL6 signaling, while trans-signaling of IL6 is activated by the formation of IL6-sIL6-mgp130 complex on cells that express gp130 but not IL6R. A third type of IL6 signaling has been recently discovered to be required for priming of pathogenic T helper 17 cells where the complex formed by IL6 and mIL6R on dendritic cells is presented to mgp130-expressing T cells (Heinrich, P. C et al., (2003) *Biochem. J.* 374: 1-20). The sIL6 mediated signaling cascade may be down-regulated by soluble gp130 existing in circulating blood upon interaction with IL6-sIL6R (Jostock, T et al., (2001) *Eur. J. Biochem* 268(1): 160-167). The IL6 signaling mainly activates two downstream pathways, the JAK and STAT3 pathway and the JAK-SHP2-MAP kinase pathway (Kang, S et al., (2019) supra).

IL6 has been reported to differentiate activated B cells into immunoglobulin-producing cells, and to drive native CD4+ T cells to Th17 lineage producing inflammatory cytokine IL17 (Hirano, T et al., (1986) *Nature* 324(6092): 73-76; Bettelli, E et al., (2006) *Nature* 441(7090): 235-238). Excessive IL6 expression may disrupt immune tolerance, leading to inflammatory diseases. For example, autoimmune symptoms were observed in patients with cardiac myxoma with high IL6 level (Hirano, T et al., (1987) *Proc. Natl. Acad. Sci. U.S.A.* 84(1): 228-231). IL6 is further found to stimulate tumor cell proliferation, and is associated with poor prognosis in cancers such as renal cell carcinoma, lymphoma, ovarian cancer, melanoma and prostate cancer (Lee, S. O et al., (2007) *Prostate* 67: 764-773). In addition, IL6 plays roles in bone homeostasis, tissue regeneration, lipid metabolism, angiogenesis and etc.

IL6 signaling has been targeted for treatment of inflammatory diseases, including autoimmune diseases. For example, Actemra® tocilizumab, the first developed IL6R blocker that inhibits IL6 binding to both mIL6R and sIL6R, has been approved in more than 100 countries around the world for treatment of rheumatoid arthritis, systemic and polyarticular juvenile idiopathic arthritis, giant cell arteritis, Takayasu arteritis, Castleman's disease and chimeric antigen receptor T cell complicated cytokine release syndrome. Tocilizumab is also being tested in clinical trials for potential efficacy against cancers and other inflammatory diseases such as systemic sclerosis. Some other biologics targeting IL6 and/or IL6R are reported to be tested for efficacy and safety profile. Antibodies with improved efficacy and safety are always desired.

Citation or identification of any document in this application is not an admission that such document is available as prior art to the present invention.

SUMMARY OF THE INVENTION

The present disclosure provides an isolated monoclonal antibody, for example, a mouse, chimeric or humanized monoclonal antibody, or an antigen-binding portion thereof, that binds to IL6R (e.g., the human IL6R) and has comparable, if not higher, binding affinity/capacity to human and/or monkey IL6R, and comparable, if not higher, blocking activity on IL6-IL6R interaction, as compared to prior art anti-IL6R antibodies such as tocilizumab.

The antibody or antigen-binding portion of the disclosure can be used for a variety of applications, including treatment of IL6 and/or IL6R associated diseases, such as inflammatory diseases, and cancers.

Accordingly, in one aspect, the disclosure pertains to an isolated monoclonal antibody (e.g., a mouse, chimeric or humanized antibody), or an antigen-binding portion thereof, that binds IL6R, having i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 4 and 11, respectively; (2) SEQ ID NOs: 2, 5 and 12, respectively; (3) SEQ ID NOs: 2, 6 and 13, respectively; (4) SEQ ID NOs: 3, 7 and 11, respectively; (5) SEQ ID NOs: 2, 8 and 13, respectively; (6) SEQ ID NOs: 2, 9 and 13, respectively; or (7) SEQ ID NOs: 2, 10 and 14, respectively; and/or ii) a light chain variable region that may comprise a VL CDR1 region, a VL CDR2 region and a VL CDR3 region, wherein the VL CDR1 region, the VL CDR2 region, and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 15, 18 and 22, respectively; (2) SEQ ID NOs: 16, 19 and 22, respectively; (3) SEQ ID NOs: 15, 20 and 22, respectively; (4) SEQ ID NOs: 16, 20 and 22, respectively; or (5) SEQ ID NOs: 17, 21 and 23, respectively.

The isolated monoclonal antibody, or the antigen-binding portion thereof, of the present disclosure may comprise a heavy chain variable region and a light chain variable region, wherein the VH CDR1, VH CDR2 and VH CDR3, and the VL CDR1, VL CDR2 and VL CDR3 may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 4, 11, 15, 18 and 22, respectively; (2) SEQ ID NOs: 2, 5, 12, 16, 19 and 22, respectively; (3) SEQ ID NOs: 2, 6, 13, 15, 20 and 22, respectively; (4) SEQ ID NOs: 3, 7, 11, 16, 20 and 22, respectively; (5) SEQ ID NOs: 2, 8, 13, 16, 20 and 22, respectively; (6) SEQ ID NOs: 2, 9, 13, 15, 20 and 22, respectively; or (7) SEQ ID NOs: 2, 10, 14, 17, 21 and 23, respectively.

The heavy chain variable region may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs:24, 25 (X1=I, X2=K, X3=A; X1=M, X2=T, X3=V; or X1=I, X2=T, X3=V), 26, 27 (X1=K, X2=L, X3=R; X1=K, X2=M, X3=V; or X1=R, X2=L, X3=V), 28, 29, 30, 31, 32 (X1=N, X2=L; or X1=E, X2=F) or 33. The amino acid sequence of SEQ ID NO: 24 may be encoded by the nucleotide sequences of SEQ ID NOs: 46 or 47. The amino acid sequence of SEQ ID NO: 27 (X1=R, X2=L, X3=V) may be encoded by the nucleotide sequence of SEQ ID NO: 48.

The light chain variable region may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 34, 35 (X1=Y, X2=M; or X1=F, X2=L), 36, 37, 38, 39 (X1=Y, X2=H, X3=E; or X1=S, X2=R, X3=G) or 40. The amino acid sequence of SEQ ID NO: 34 may be encoded by the nucleotide sequences of SEQ ID NOs: 49 or 50. The amino acid sequence of SEQ ID NO: 35 (X1=Y, X2=M) may be encoded by the nucleotide sequence of SEQ ID NO: 51.

The isolated monoclonal antibody, or the antigen-binding portion thereof, of the present disclosure may comprise a heavy chain variable region and a light chain variable region, the heavy chain variable region and the light chain variable region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 24 and 34, respectively; (2) SEQ ID NOs: 25 (X1=I, X2=K, X3=A) and 35 (X1=Y, X2=M), respectively; (3) SEQ ID NOs: 26 and 36, respectively; (4) SEQ ID NOs: 27 (X1=K, X2=L, X3=R) and 35 (X1=Y, X2=M), respectively; (5) SEQ ID NOs: 27 (X1=K, X2=M, X3=V) and 35 (X1=Y, X2=M), respectively; (6) SEQ ID NOs: 25 (X1=M, X2=T, X3=V) and 35 (X1=Y, X2=M), respectively; (7) SEQ ID NOs: 27 (X1=R, X2=L, X3=V) and 35 (X1=Y, X2=M), respectively; (8) SEQ ID NOs: 25 (X1=I, X2=T, X3=V) and 35 (X1=Y, X2=M), respectively; (9) SEQ ID NOs: 25 (X1=I, X2=K, X3=A) and 35 (X1=F, X2=L), respectively; (10) 27 (X1=K, X2=L, X3=R) and 35 (X1=F, X2=L), respectively; (11) 27 (X1=K, X2=M, X3=V) and 35 (X1=F, X2=L), respectively; (12) SEQ ID NOs: 25 (X1=M, X2=T, X3=V) and 35 (X1=F, X2=L), respectively; (13) 27 (X1=R, X2=L, X3=V) and 35 (X1=F, X2=L), respectively; (14) SEQ ID NOs: 25 (X1=I, X2=T, X3=V) and 35 (X1=F, X2=L), respectively; (15) SEQ ID NOs: 28 and 37, respectively; (16) SEQ ID NOs: 29 and 38, respectively; (17) SEQ ID NOs: 30 and 39 (X1=Y, X2=H, X3=E), respectively; (18) SEQ ID NOs: 31 and 39 (X1=S, X2=R, X3=G), respectively; (19) SEQ ID NOs: 32 (X1=N, X2=L) and 38, respectively; (20) SEQ ID NOs: 32 (X1=E, X2=F) and 38, respectively; or (21) SEQ ID NOs: 33 and 40, respectively.

The isolated monoclonal antibody, or the antigen-binding portion thereof, of the present disclosure may comprise a heavy chain and a light chain linked by disulfide bonds, the heavy chain may comprise a heavy chain variable region and a heavy chain constant region, the light chain may comprise a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region may comprise amino acid sequences described above, and the antibody or antigen-binding portion thereof binds to IL6R. The heavy chain constant region may be human IgG1 constant region having an amino acid sequence set forth in e.g., SEQ ID NO.: 41, or a functional fragment thereof, and the light chain constant region may be human kappa constant region having an amino acid sequences set forth in e.g., SEQ ID NO.: 42, or a functional fragment thereof. The heavy chain constant region may also be human IgG4 constant region. The light chain constant region may be human kappa constant region. The amino acid sequence of SEQ ID NO: 41 and 42 may be encoded by the nucleotide sequences of SEQ ID NOs: 52 and 53, respectively.

The antibody of the present disclosure in some embodiments may comprise or consist of two heavy chains and two light chains, wherein each heavy chain may comprise the heavy chain constant region, heavy chain variable region or CDR sequences mentioned above, and each light chain may comprise the light chain constant region, light chain variable region or CDR sequences mentioned above, wherein the antibody binds to IL6R. The antibody of the disclosure can be a full-length antibody, for example, of an IgG1, IgG2 or IgG4 isotype. The antibody or the antigen-binding portion thereof of the present disclosure in other embodiments may be a single chain variable fragment (scFv) antibody, or antibody fragments, such as Fab or $Fab'_2$ fragments.

The disclosure also provides a bispecific molecule that may comprise the antibody, or the antigen-binding portion thereof, of the disclosure, linked to a second functional moiety (e.g., a second antibody) having a different binding specificity than said antibody, or antigen-binding portion thereof. The disclosure also provides an immunoconjugate, such as an antibody-drug conjugate, that may comprise an antibody, or antigen-binding portion thereof, of the disclosure, linked to a therapeutic agent, such as a cytotoxin. In another aspect, the antibody or the antigen binding portion thereof of the present disclosure can be made into part of a chimeric antigen receptor (CAR). Also provided is an immune cell that may comprise the antigen chimeric receptor, such as a T cell and a NK cell. The antibody or the antigen binding portion thereof of the present disclosure can also be encoded by or used in conjunction with an oncolytic virus.

Nucleic acid molecules encoding the antibody, or the antigen-binding portion thereof, of the disclosure are also encompassed by the disclosure, as well as expression vectors that may comprise such nucleic acids and host cells that may comprise such expression vectors. A method for preparing the anti-IL6R antibody or the antigen-binding portion thereof of the disclosure using the host cell is also provided, that may comprise steps of (i) expressing the antibody in the host cell and (ii) isolating the antibody from the host cell or its cell culture.

Compositions that may comprise the antibody or the antigen-binding portion thereof, the immunoconjugate, bispecific molecule, oncolytic virus, CAR, CAR-T cell, the nucleic acid molecule, the expression vector or the host cell of the disclosure, and a pharmaceutically acceptable carrier, are also provided. In some embodiments, the pharmaceutical composition may further contain a therapeutic agent for treating a specific disease, such as an anti-inflammatory agent, or an anti-cancer agent.

In yet another aspect, the disclosure provides a method for treating a disease associated with excessive IL6/IL6R signaling, which may comprise administering to a subject a therapeutically effective amount of the composition of the present disclosure.

The disease may be an inflammatory disease, such as an autoimmune disease. The inflammatory disease includes, but not limited to, rheumatoid arthritis, systemic and polyarticular juvenile idiopathic arthritis, giant cell arteritis, Takayasu arteritis, Castleman's disease, cytokine release syndrome (e.g., chimeric antigen receptor T cell complicated cytokine release syndrome), Schnitzler syndrome, and neuromyelitis optica. The method may comprise further administering an anti-inflammatory agent, including, but not limited to, an anti-CD3 antibody, an anti-CD20 antibody, an anti-CD22 antibody, an anti-IL2R antibody, an anti-IL6 antibody, and an anti-IL17 antibody.

The disease may be a tumor or cancer. The tumor may be a solid tumor or a hematological tumor, including, but not limited to, non-small cell lung cancer, and diffuse large B-cell lymphoma. In some embodiments, at least one additional anti-cancer antibody may be further administered, such as an anti-VISTA antibody, an anti-PD-1 antibody, an anti-PD-L1 antibody, an anti-LAG-3 antibody, an anti-CTLA-4 antibody, an anti-TIM 3 antibody, an anti-STAT3 antibody, and/or an anti-ROR1 antibody.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
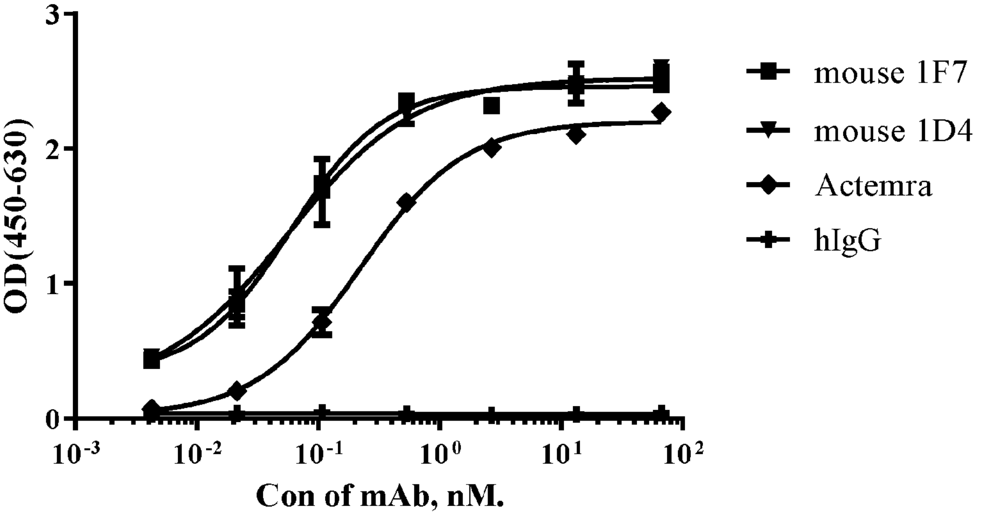
FIGS. 1A-1D show the binding capacities of mouse antibodies 1F7 and 1D4 (A), 1A3, 1B5 and 1G8 (B), 3C2 and 1G1 (C), 1H9 and 1H7 (D) to human IL6R in the capture ELISA.
Figure 1B:
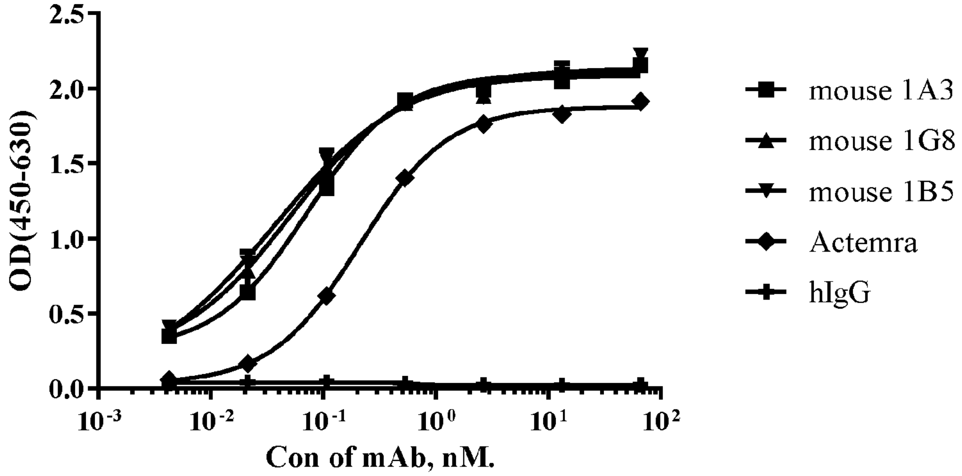
Figure 1C:
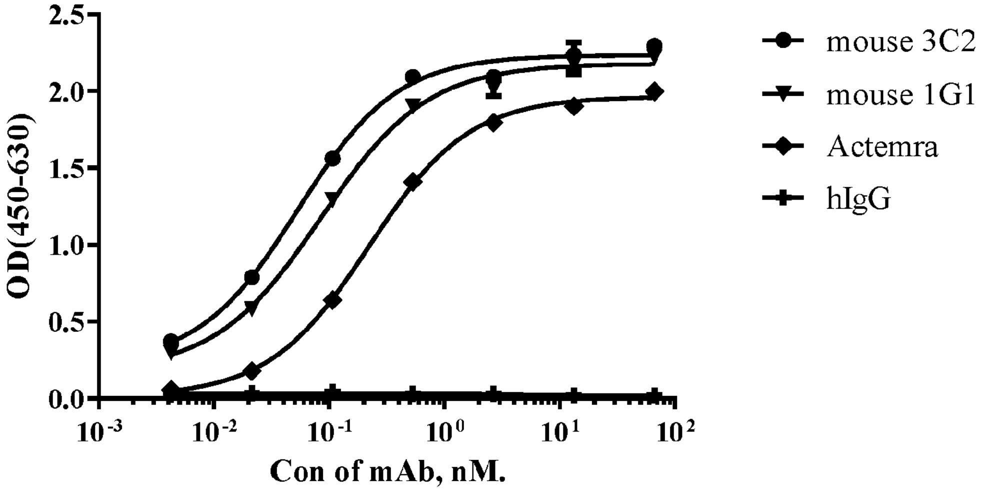
Figure 1D:
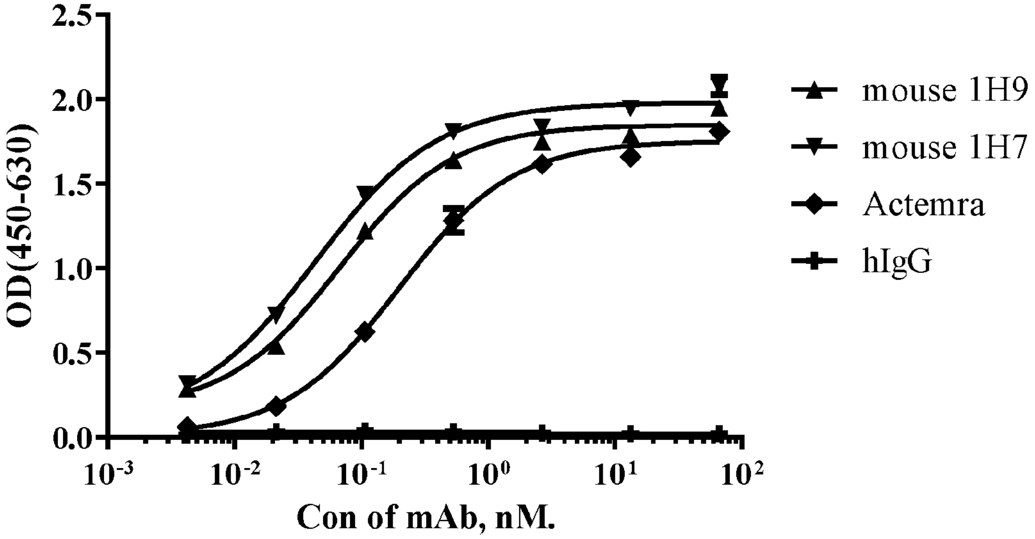

To ensure that the present disclosure may be more readily understood, certain terms are first defined. Additional definitions are set forth throughout the detailed description.

The term "IL6R" refers to interleukin 6 receptor, also known as Cluster of Differentiation 126 (CD126). The term "IL6R" may comprise variants, isoforms, homologs, orthologs and paralogs. For example, an antibody specific for a human IL6R protein may, in certain cases, cross-react with an IL6R protein from a species other than human, such as monkey. In other embodiments, an antibody specific for a human IL6R protein may be completely specific for the human IL6R protein and exhibit no cross-reactivity to other species or of other types, or may cross-react with IL6R from certain other species but not all other species.

The term "human IL6R" refers to an IL6R protein having an amino acid sequence from a human, such as the amino acid sequence of human IL6R having a Genbank accession number of NP_000556.1. The terms "macaca IL6R" refer to an IL6R protein having an amino acid sequence from macaca mulatta, such as the amino acid sequence having Genbank Accession No. NP_001036198.2.

The term "antibody" as referred to herein includes whole antibodies and any antigen binding fragment (i.e., "antigen-binding portion") or single chains thereof. Whole antibodies are glycoproteins which may comprise two heavy (H) chains and two light (L) chains inter-connected by disulfide bonds. Each heavy chain may be comprised of a heavy chain variable region (abbreviated herein as VH) and a heavy chain constant region. The heavy chain constant region may be comprised of three domains, $C_{H1}$, $C_{H2}$ and $C_{H3}$. Each light chain may be comprised of a light chain variable region (abbreviated herein as $V_L$) and a light chain constant region. The light chain constant region may be comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., an IL6R protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds an IL6R protein is substantially free of antibodies that specifically bind antigens other than IL6R proteins). An isolated antibody that specifically binds a human IL6R protein may, however, have cross-reactivity to other antigens, such as IL6R proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human IL6R" is intended to refer to an antibody that binds to human IL6R protein (and possibly an IL6R protein from one or more non-human species) but does not substantially bind to non-IL6R proteins. Preferably, the antibody binds to human IL6R protein with "high affinity", namely with a $K_D$ of $5.0\times10^{-8}$ M or less, more preferably $1.0\times10^{-8}$ M or less, and more preferably $7.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, even more preferably $3.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ System.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

The antibody, or the antigen-binding portion thereof, of the disclosure specifically binds to human IL6R with comparable, if not better, binding affinity/capacity as compared to previously described anti-IL6R antibodies, such as Tocilizumab.

The antibody, or the antigen-binding portion thereof, of the disclosure blocks IL6 binding to IL6R and thus the generation of IL6-IL6R-gp130 complex, with comparable or higher activity, as compared to previously described anti-IL6R antibodies, such as Tocilizumab.

The antibodies of the disclosure are mouse, chimeric and humanized monoclonal antibodies.

The antibody of the disclosure is the monoclonal antibody structurally and chemically characterized as described below and in the following Examples. The amino acid sequence ID numbers of the heavy/light chain variable regions of the antibodies are summarized in Table 1 below, some antibodies sharing the same $V_H$ or $V_L$. The heavy chain constant region for the antibodies may be human IgG1 heavy chain constant region having an amino acid sequence set forth in, e.g., SEQ ID NO: 41, and the light chain constant region for the antibodies may be human kappa constant region having an amino acid sequence set forth in, e.g., SEQ ID NO: 42. The antibodies of the disclosure may also contain human IgG4 heavy chain constant region and human kappa light chain constant region.

TABLE 1

Amino acid sequence ID numbers of heavy/light chain CDRs and variable regions

| Antibody ID | VH-CDR1 (SEQ ID NO.) | VH-CDR2 (SEQ ID NO.) | VH-CDR3 (SEQ ID NO.) | VH (SEQ ID NO.) | VL-CDR1 (SEQ ID NO.) | VL-CDR2 (SEQ ID NO.) | VL-CDR3 (SEQ ID NO.) | VL (SEQ ID NO.) |
|---|---|---|---|---|---|---|---|---|
| 1H7 | 1 | 4 | 11 | 24 | 15 | 18 | 22 | 34 |
| hu1H7-V1 | 1 | 4 | 11 | 25, X1 = I, X2 = K, X3 = A | 15 | 18 | 22 | 35, X1 = Y, X2 = M |

TABLE 1-continued

Amino acid sequence ID numbers of heavy/light chain CDRs and variable regions

| Antibody ID | VH-CDR1 (SEQ ID NO.) | VH-CDR2 (SEQ ID NO.) | VH-CDR3 (SEQ ID NO.) | VH (SEQ ID NO.) | VL-CDR1 (SEQ ID NO.) | VL-CDR2 (SEQ ID NO.) | VL-CDR3 (SEQ ID NO.) | VL (SEQ ID NO.) |
|---|---|---|---|---|---|---|---|---|
| hu1H7-Vl-2 | 1 | 4 | 11 | 26 | 15 | 18 | 22 | 36 |
| hu1H7-V2 | 1 | 4 | 11 | 27, X1 = K, X2 = L, X3 = R | 15 | 18 | 22 | 35, X1 = Y, X2 = M |
| hu1H7-V3 | 1 | 4 | 11 | 27, X1 = K, X2 = M, X3 = V | 15 | 18 | 22 | 35, X1 = Y, X2 = M |
| hu1H7-V4 | 1 | 4 | 11 | 25, X1 = M, X2 = T, X3 = V | 15 | 18 | 22 | 35, X1 = Y, X2 = M |
| hu1H7-V5 | 1 | 4 | 11 | 27, X1 = R, X2 = L, X3 = V | 15 | 18 | 22 | 35, X1 = Y, X2 = M |
| hu1H7-V6 | 1 | 4 | 11 | 25, X1 = I, X2 = T, X3 = V | 15 | 18 | 22 | 35, X1 = Y, X2 = M |
| hu1H7-V7 | 1 | 4 | 11 | 25, X1 = I, X2 = K, X3 = A | 15 | 18 | 22 | 35, X1 = F, X2 = L |
| hu1H7-V8 | 1 | 4 | 11 | 27, X1 = K, X2 = L, X3 = R | 15 | 18 | 22 | 35, X1 = F, X2 = L |
| hu1H7-V9 | 1 | 4 | 11 | 27, X1 = K, X2 = M, X3 = V | 15 | 18 | 22 | 35, X1 = F, X2 = L |
| hu1H7-V10 | 1 | 4 | 11 | 25, X1 = M, X2 = T, X3 = V | 15 | 18 | 22 | 35, X1 = F, X2 = L |
| hu1H7-V11 | 1 | 4 | 11 | 27, X1 = R, X2 = L, X3 = V | 15 | 18 | 22 | 35, X1 = F, X2 = L |
| hu1H7-V12 | 1 | 4 | 11 | 25 , X1 = I, X2 = T, X3 = V | 15 | 18 | 22 | 35, X1 = F, X2 = L |
| 1F7 | 2 | 5 | 12 | 28 | 16 | 19 | 22 | 37 |
| 1B5 | 2 | 6 | 13 | 29 | 15 | 20 | 22 | 38 |
| 3C2 | 3 | 7 | 11 | 30 | 16 | 20 | 22 | 39, X1 = Y, X2 = H, X3 = E |
| 1A3 | 2 | 8 | 13 | 31 | 16 | 20 | 22 | 39, X1 = S, X2 = R, X3 = G |
| 1D4 | 2 | 9 | 13 | 32, X1 = N, X2 = L | 15 | 20 | 22 | 38 |
| 1G1 | 2 | 9 | 13 | 32, X1 = E, X2 = F | 15 | 20 | 22 | 38 |
| 1H9 | 2 | 10 | 14 | 33 | 17 | 21 | 23 | 40 |

TABLE 2

Amino acid sequences of heavy and light chain CDRs

| mAh ID | VH-CDR1 VH-CDR2 | VH-CDR3 VL-CDR1 | VL-CDR2 | VL-CDR3 |
|---|---|---|---|---|
| 1H7 | **N**YW**M**HEINP**T**NGRT<br>N**Y**NE**N**FK**S** | L**NT**HYS**V**SSSIS<br>VFD**S** SNYLH | **R**T**S**TLAS | QQGS<br>GIPFT |
| 1F7 | **S**YW**M**HEINP**S**NGRT<br>N**Y**NE**K**FK**N** | L**SI**HYS**A**SSSIS<br>VFD**Y** SNYLH | **G**T**S**NLAS | QQGSG<br>IPFT |
| 1B5 | **S**YW**M**HEINP**S**NGRT<br>N**Y**NE**N**FK**S** | L**NT**HYS**V**SSSIS<br>VFD**Y** SNYLH | **R**T**S**NLAS | QQGSG<br>IPFT |
| 3C2 | **T**YW**I**HEINP**S**NGRT<br>N**Y**NE**H**FK**S** | L**NT**HYS**A**SSSIS<br>VFD**S** SNYLH | **R**T**S**NLAS | QQGSG<br>IPFT |
| 1A3 | **S**YW**M**HEINP**S**NGRT<br>N**F**NE**K**FK**T** | L**NT**HYS**A**SSSIS<br>VFD**Y** SNYLH | **R**T**S**NLAS | QQGSG<br>IPFT |
| 1D4 | **S**YW**M**HEINP**T**NGRT<br>N**Y**NE**D**FK**S** | L**NT**HYS**V**SSSIS<br>VFD**Y** SNYLH | **R**T**S**NLAS | QQGSG<br>IPFT |
| 1G1 | **S**YW**M**HEINP**T**NGRT<br>N**Y**NE**D**FK**S** | L**NT**HYS**V**SSSIS<br>VFD**Y** SNYLH | **R**T**S**NLAS | QQGSG<br>IPFT |

The heavy chain variable region CDRs and the light chain variable region CDRs in Table 1 have been defined by the Kabat numbering system. However, as is well known in the art, CDR regions can also be determined by other systems such as Chothia, and IMGT, AbM, or Contact numbering system/method, based on heavy chain/light chain variable region sequences.

The detailed heavy chain or light chain CDR sequences of the disclosure are set forth in Table 2, expect 1H9 whose CDR sequences are quite different from others. It can be seen that the 7 antibodies contain exactly the same light chain CDR3, and quite similar heavy chain CDR1, CDR2, CDR3 and light chain CDR1, CDR2.

The $V_H$ and $V_L$ sequences (or CDR sequences) of other Anti-IL6R antibodies which bind to human IL6R can be "mixed and matched" with the $V_H$ and $V_L$ sequences (or CDR sequences) of the anti-IL6R antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, may comprise:

(a) a heavy chain variable region which may comprise an amino acid sequence listed above in Table 1; and (b) a light chain variable region which may comprise an amino acid sequence listed above in Table 1, or the $V_L$ of another Anti-IL6R antibody, wherein the antibody specifically binds human IL6R.

In another embodiment, an antibody of the disclosure, or an antigen binding portion thereof, may comprise:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-IL6R antibody, wherein the antibody specifically binds human IL6R.

In yet another embodiment, the antibody, or antigen binding portion thereof, includes the heavy chain variable CDR2 region of anti-IL6R antibody combined with CDRs of other antibodies which bind human IL6R, e.g., CDR1 and/or CDR3 from the heavy chain variable region, and/or CDR1, CDR2, and/or CDR3 from the light chain variable region of a different anti-IL6R antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure may comprise the CDR2 of the heavy chain variable region of the anti-IL6R antibody and at least the CDR3 of the heavy and/or light chain variable region of the anti-IL6R antibody, or the CDR3 of the heavy and/or light chain variable region of another anti-IL6R antibody, wherein the antibody is capable of specifically binding to human IL6R. These antibodies preferably (a) compete for binding with IL6R; (b) retain the functional characteristics; (c) bind to the same epitope; and/or (d) have a similar binding affinity as the anti-IL6R antibody of the present disclosure. In yet another embodiment, the antibodies further may comprise the CDR2 of the light chain variable region of the anti-IL6R antibody, or the CDR2 of the light chain variable region of another anti-IL6R antibody, wherein the antibody is capable of specifically binding to human IL6R. In another embodiment, the antibodies of the disclosure may include the CDR1 of the heavy and/or light chain variable region of the anti-IL6R antibody, or the CDR1 of the heavy and/or light chain variable region of another anti-IL6R antibody, wherein the antibody is capable of specifically binding to human IL6R.

In another embodiment, an antibody of the disclosure may comprise a heavy and/or light chain variable region sequences of CDR1, CDR2 and CDR3 sequences which differ from those of the anti-IL6R antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody may comprise a heavy chain variable region which may comprise CDR1, CDR2, and CDR3 sequences and/or a light chain variable region which may comprise CDR1, CDR2, and CDR3 sequences, wherein:

(a) the heavy chain variable region CDR1 sequence may comprise a sequence listed in Table 1 above, and/or conservative modifications thereof; and/or (b) the heavy chain variable region CDR2 sequence may comprise a sequence listed in Table 1 above, and/or conservative modifications thereof; and/or (c) the heavy chain variable region CDR3 sequence may comprise a sequence listed in Table 1 above, and conservative modifications thereof; and/or (d) the light chain variable region CDR1, and/or CDR2, and/or CDR3 sequences may comprise the sequence(s) listed in Table 1 above; and/or conservative modifications thereof; and (e) the antibody specifically binds human IL6R.

The antibody of the present disclosure possesses one or more of the following functional properties described above, such as high affinity binding to human IL6R, and blocking activity on IL6R-IL6 binding.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-IL6R antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, which may comprise a heavy chain variable region that may comprise CDR1, CDR2, and CDR3 sequences which may comprise the sequences of the present disclosure, as described above, and/or a light chain variable region which may comprise CDR1, CDR2, and CDR3 sequences which may comprise the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-IL6R monoclonal antibodies, or antigen binding portions thereof, which may comprise a heavy chain variable region that may comprise: (a) a $V_H$ CDR1 region which may comprise the sequence of the present disclosure, or an amino acid sequence having one, two, three, four or five amino acid substitutions, deletions or additions; (b) a $V_H$ CDR2 region which may comprise the sequence of the present disclosure, or an amino acid sequence having one, two, three, four or five amino acid substitutions, deletions or additions; (c) a $V_H$ CDR3 region which may comprise the sequence of the present disclosure, or an amino acid sequence having one, two, three, four or five amino acid substitutions, deletions or additions; (d) a $V_L$ CDR1 region which may comprise the sequence of the present disclosure, or an amino acid sequence having one, two, three, four or five amino acid substitutions, deletions or additions; (e) a $V_L$ CDR2 region which may comprise the sequence of the present disclosure, or an amino acid sequence having one, two, three, four or five amino acid substitutions, deletions or additions; and (f) a $V_L$ CDR3 region which may comprise the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fe hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (a (1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1, 6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application 60/836,998, filed on Aug. 11, 2006. The fucose residues of the antibody can be cleaved off using a fucosidase enzyme; e.g., the fucosidase α-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-IL6R antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-IL6R antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the IL6R monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyomavirus enhancer. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In another aspect, the present disclosure features bispecific molecules which may comprise one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-IL6R binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6), 635-644 (1998); and van Spriel et al., *Immunology Today,* 21 (8), 391-397 (2000), and the references cited therein.

In yet another aspect, the invention provides diagnostic methods, compositions and kits. In an embodiment, an antibody of the invention is used to determine the presence and expression of IL6Rα in a cell or tissue. In an embodiment, the diagnostic indicates prognosis and/or directs treatment and/or follow-up treatment. For example, IL6 signaling has been targeted for treatment of inflammatory diseases, including autoimmune diseases and/or IL6/IL6R related tumors or cancers. In an embodiment, an antibody of the invention is employed in diagnostic kit or method to determine prognosis and appropriate treatment and followup of an autoimmune disease and/or IL6/IL6R related tumors or cancers.

Antibodies of the disclosure can be conjugated to a therapeutic agent to form an immunoconjugate such as an antibody-drug conjugate (ADC). Suitable therapeutic agents include an anti-inflammatory agent and an anti-cancer agent. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

An oncolytic virus preferentially infects and kills cancer cells. Antibodies of the present disclosure can be used in conjunction with oncolytic viruses. Alternatively, oncolytic viruses encoding antibodies of the present disclosure can be introduced into human body.

Also provided herein are a chimeric antigen receptor (CAR) containing an anti-IL6R scFv, the anti-IL6R scFv may comprise CDRs and heavy/light chain variable regions described herein.

The anti-IL6R CAR may comprise (a) an extracellular antigen binding domain which may comprise an anti-IL6R scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, which may comprise the CAR provided herein. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

In another aspect, the present disclosure provides a pharmaceutical composition which may comprise one or more antibodies ((or antigen-binding portion thereof, or the bispecifics, CAR-T cells, oncolytic viruses, immunoconjugates) of the present disclosure formulated together with a pharmaceutically acceptable carrier. The antibodies (or antigen-binding portion thereof, or the bispecifics, CAR-T cells, oncolytic viruses, immunoconjugates) can be dosed separately when the composition contains more than one antibody (or antigen-binding portion thereof, or the bispecifics, CAR-T cells, oncolytic viruses, immunoconjugates). The composition may optionally contain one or more additional pharmaceutically active ingredients, such as another antibody or a drug, such as an anti-tumor drug or an anti-inflammatory agent.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg.

A "therapeutically effective dosage" of an anti-IL6R antibody, or the antigen-binding portion thereof, or the bispecifics, CAR-T cells, oncolytic viruses, immunoconjugates of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition which may comprise the antibodies or the antigen-binding portion thereof, or the bispecifics, CAR-T cells, oncolytic viruses, immunoconjugates of the present disclosure have numerous in vitro and in vivo utilities involving, for example, treatment of inflammatory diseases with excessive IL6 signaling.

Given the ability of anti-IL6R antibodies of the disclosure to block IL6 binding with IL6R, the disclosure provides methods for treating IL6/IL6R related inflammatory diseases such as autoimmune diseases, and Castleman's disease, which may comprise administering to the subject the pharmaceutical composition of the disclosure. The inflammatory diseases includes, but not limited to, rheumatoid arthritis, systemic and polyarticular juvenile idiopathic arthritis, giant cell arteritis, Takayasu arteritis, Castleman's disease, chimeric antigen receptor T cell complicated cytokine release syndrome, cytokine release syndrome, Schnitzler syndrome, and neuromyelitis optica.

In one aspect, the disclosure provides combination therapy in which the pharmaceutical composition of the present disclosure is co-administered with one or more additional agents that are effective in ameliorating IL6/IL6R related inflammatory diseases. Such agents may be an anti-CD3 antibody, an anti-CD20 antibody, an anti-CD22 antibody, an anti-IL2R antibody, an anti-IL6 antibody, and an anti-IL17 antibody. In certain embodiments, the subject is human.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Although the present invention and its advantages have been described in detail, it should be understood that various changes, substitutions and alterations can be made herein without departing from the spirit and scope of the invention as defined in the appended claims.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-IL6R Monoclonal Antibodies Using Hybridoma Technology Immunization Mice were immunized according to the method described in E Harlow, D. Lane, Antibody: A Laboratory Manual, Cold Spring Harbor Laboratory Press, Cold Spring Harbor, N.Y., 1998. Recombinant human IL6Rα-his protein (Acro biosystems, Cat #ILR-H4223) was used as immunogen, and in house made human IL6R-Fc protein (amino acid sequence set forth in SEQ ID NO: 43) was used for determining anti-sera titer and screening hybridomas secreting antigen-specific antibodies. Immunizing dosages contained 50 μg human IL6Rα-his per mouse per injection for primary immunization, and 25 μg human IL6Rα-his per mouse per injection for boost immunizations. To increase immune response, the complete Freud's adjuvant and incomplete Freud's adjuvant (Sigma, St. Louis, Mo., USA) were used respectively for primary and boost immunizations. Briefly, the desired amount of adjuvant was transferred into an autoclaved 1.5 mL micro-centrifuge tube. The antigen was prepared in PBS or saline with concentration ranging from 0.25-1.0 mg/ml. The calculated amount of antigen was then added to the micro-centrifuge tube with the adjuvant, and the solution was mixed by gently vortexing for 2 minutes to generate water-in-oil emulsion. The adjuvant-antigen mixture was then drawn into the proper syringe for animal injection. A total of 50 or 25 μg of antigen was injected in a volume of 100-200 μl. Each animal was immunized, and then boosted for 2 to 3 times depending on the anti-sera titer. Animals with good titers were given a final boost by intraperitoneal injection before fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method described in E Harlow, D. Lane, Antibody: A Laboratory Manual, Cold Spring Harbor Laboratory Press, Cold Spring Harbor, N.Y., 1998. Fused "hybrid cells" were subsequently dispensed into 96-well cell plates in DMEM/20% v/v FCS/HAT media. Surviving hybridoma colonies were observed under the microscope seven to ten days post-fusion. After two weeks, the supernatant from each well was subjected to indirect ELISA and Capture ELISA using human IL6R-Fc protein (in house made with SEQ ID NO: 43). Positive hybridomas secreting antibodies binding to human IL6R-Fc were then selected and transferred to 24-well plates. These hybridomas were further tested for the activity for blocking IL6R-IL6 binding. Hybridoma clones producing antibodies that showed high specificity to human IL6R and high IL6-IL6R blocking activity were subcloned by limiting dilution to ensure the clonality of the cell line, and then monoclonal antibodies were purified. Briefly, Protein A sepharose column (from bestchrom (Shanghai) Biosciences, Cat #AA0273) was washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C. Subsequently, the functional activities of purified monoclonal antibodies were characterized in vitro as follows.

Example 2 Affinity Determination of Mouse Anti-IL6R Monoclonal Antibodies Using BIACORE Surface Plasmon Resonance The purified anti-IL6R mouse monoclonal antibodies (mAbs) generated in Example 1 were characterized for binding affinity and kinetics by Biacore T200 system (GE healthcare, Pittsburgh, PA, USA).

Briefly, goat anti-mouse IgG (GE healthcare, Cat #BR100838, Mouse Antibody Capture Kit) was covalently linked to a CM5 chip (carboxy methyl dextran coated chip from GE healthcare #BR100530) via primary amines using a standard amine coupling kit (GE healthcare, Pittsburgh, PA, USA) provided by Biacore, and a Protein G chip (GE healthcare, Cat #29-1793-15) was used for the benchmark's affinity determination. Un-reacted moieties on the biosensor surface were blocked with ethanolamine. Then purified anti-IL6R antibodies of the disclosure and an anti-IL6R benchmark (Tocilizumab, also referred to as benchmark or Actemra® herein, in house made with heavy chain and light chain amino acid sequences set forth in SEQ ID NOs: 55 and 56, respectively), at the concentration of 2 μg/ml, were respectively flown onto the chip at a flow rate of 10 μL/min. Then, serially diluted recombinant human IL6R-his (in house made, amino acid sequence set forth in SEQ ID NO: 44) or macaca IL6R-his protein (in house made, amino acid sequence set forth in SEQ ID NO: 45), starting at 100 nM with a 2-fold serial dilution in HBS-EPV buffer (provided by Biacore), was flowed onto the chip at a flow rate of 30 μL/min. The antigen-antibody association kinetics was followed for 2 minutes and the dissociation kinetics was followed for 10 minutes. The association and dissociation curves were fit to a 1:1 Langmuir binding model using BIAcore evaluation software. The $K_D$, $K_a$ and $K_d$ values were determined and summarized in Table 3 below.

All the tested anti-IL6R antibodies of the present disclosure specifically bound to human IL6R and macaca IL6R at higher binding affinity than Tocilizumab.

TABLE 3

Biacore Kinetics of mouse Anti-IL6R monoclonal Antibodies Binding to Human and Macaca IL6R

| | Kinetics on Biacore | | | | | |
|---|---|---|---|---|---|---|
| | Human IL6R-his | | | Macaca IL6R-his | | |
| mAb ID | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| 1A3 | 1.48E+05 | 4.32E−05 | 2.93E−10 | 1.39E+05 | 4.54E−05 | 3.28E−10 |
| 1B5 | 1.41E+05 | 6.70E−05 | 4.76E−10 | 1.29E+05 | 7.86E−05 | 6.09E−10 |
| 1G1 | 1.41E+05 | 9.09E−05 | 6.47E−10 | 1.20E+05 | 8.85E−05 | 7.36E−10 |
| 1F7 | 1.39E+05 | 7.46E−05 | 5.37E−10 | 1.24E+05 | 6.46E−05 | 5.23E−10 |
| 1D4 | 1.38E+05 | 8.64E−05 | 6.28E−10 | 1.23E+05 | 7.39E−05 | 6.00E−10 |
| 1G8 | 1.54E+05 | 4.94E−05 | 3.21E−10 | 1.38E+05 | 3.33E−05 | 2.42E−10 |
| 1H9 | 1.12E+05 | 1.20E−04 | 1.08E−09 | 9.41E+04 | 1.55E−04 | 1.65E−09 |
| 1H7 | 1.53E+05 | 4.73E−05 | 3.08E−10 | 1.37E+05 | 3.14E−05 | 2.29E−10 |
| 3C2 | 1.48E+05 | 1.35E−04 | 9.11E−10 | 1.30E+05 | 1.27E−04 | 9.77E−10 |
| Tocilizumab | 1.01E+05 | 3.28E−04 | 3.26E−09 | 8.23E+04 | 3.13E−04 | 3.80E−09 |

Example 3 Binding Activities of Mouse Anti-IL6R Monoclonal Antibodies

The mouse anti-IL6R antibodies were tested for their binding activities by Capture ELISA, Indirect ELISA and Flow Cytometry (FACS).

3.1 Capture ELISA

For the capture ELISA, 96-well micro plates were coated with 2 μg/ml AffiniPure Goat Anti-Mouse IgG, F(ab')$_2$ fragment specific (Jackson ImmunoResearch Laboratories, Inc., Cat #115-005-072) in PBS, 100 μl/well, and incubated for 2 hours at 37° C. Plates were washed once with wash buffer (PBS+0.05% v/v Tween-20, PBST) and then blocked with 200 μl/well blocking buffer (5% w/v non-fatty milk in PBST) overnight at 4° C. Plates were washed 4 times and incubated respectively with 100 μl/well serially diluted mouse anti-IL6R antibodies of the disclosure, the benchmark and a negative control hIgG (human immunoglobulin (pH4) for intravenous injection, Hualan Biological Engineering Inc.), 5-fold dilution in 2.5% w/v non-fatty milk in PBST, starting at 10000 ng/ml, for 40 minutes at 37° C., and then washed 4 times again. Plates containing captured anti-IL6R antibodies were incubated with biotin-labeled human IL6R-Fc protein (prepared in house, SEQ ID NO: 43, 39.5 ng/ml in 2.5% w/v non-fatty milk in PBST, 100 μl/well) for 40 minutes at 37° C., washed 4 times, and incubated with streptavidin conjugated HRP (1:10000 dilution in PBST, Jackson ImmunoResearch Laboratories, Inc., Cat #016-030-084, 100 μl/well) for 40 minutes at 37° C. After a final wash, plates were incubated with 100 μl/well ELISA substrate TMB (InnoReagents, Cat #TMB-S-002). The reaction was stopped 3-10 minutes later at room temperature with 50 μl/well 1M $H_2SO_4$, and the absorbance of each well was read on a microplate reader using dual wavelength mode at 450 nm for TMB and 630 nm as the reference wavelength. Then the OD (450-630) values were plotted against antibody concentration. Data was analyzed using Graphpad Prism software and $EC_{50}$ values were reported.

3.2 Indirect ELISA

The anti-IL6R antibodies were tested for their cross-reaction with macaca IL6R. Briefly, 96-well micro plates were coated with 2 μg/ml macaca IL6R-his protein (in house made, amino acid sequence set forth in SEQ ID NO:45) in carbonate/bicarbonate buffer (pH 9.6), 100 μl/well, for 2 hours at 37° C. ELISA plates were washed once with wash buffer (PBS+0.05% v/v Tween-20, PBST) and then blocked with 200 μl/well blocking buffer (5% w/v non-fatty milk in PBST) for 2 hours at 37° C. Plates were washed 4 times and incubated with 100 μl/well serially diluted anti-IL6R antibodies of the disclosure or controls, starting at 66.67 nM with 5-fold serial dilution in PBST with 2.5% w/v non-fat milk, and incubated at 37° C. for 40 minutes. ELISA plates were washed 4 times again and incubated with 100 μl/well Peroxidase AffiniPure Goat Anti-Mouse IgG, Fcγ Fragment Specific (1:5000 dilution in PBST buffer, Jackson ImmunoResearch Laboratories, Inc., Cat #115-035-071) for 40 minutes at 37° C. After the final wash, plates were incubated with 100 μl/well TMB (InnoReagents). The reaction was stopped 3-10 minutes later at room temperature with 50 μl/well 1M $H_2SO_4$, and the absorbance of each well was read on a microplate reader using dual wavelength mode with 450 nm for TMB and 630 nm as the reference wavelength. Then the OD (450-630) values were plotted against antibody concentration. Data was analyzed using Graphpad Prism software and $EC_{50}$ values were reported.

3.3 Cell-Based Binding FACS

The binding activities of the mouse anti-IL6R antibodies to IL6R expressed on cell surface were tested by flow cytometry (FACS). Briefly, human myeloma cells U266 (ATCC® TIB-196™) were harvested from cell culture flasks, washed twice and resuspended in phosphate buffered saline (PBS) containing 2% v/v Fetal Bovine Serum (FACS buffer). $2\times10^5$ U266 cells per well were incubated in 96 well-plates with 100 μl of the anti-IL6R antibodies or controls at various concentrations (starting at 40 nM with a 3-fold serial dilution in FACS buffer) for 40 minutes on ice. Cells were washed twice with FACS buffer, and added with 100 μL/well R-Phycoerythrin AffiniPure F(ab')$_2$ Fragment Goat Anti-Mouse IgG (H+L) (1:1000 dilution in FACS buffer, Jackson ImmunoResearch Laboratories, Inc., Cat #115-116-146). Following an incubation of 40 minutes at 4° C. in dark, cells were washed three times and resuspended in FACS buffer. Fluorescence was measured using a Becton Dickinson FACS Canto II-HTS equipment. Data was analyzed using Graphpad Prism software and $EC_{50}$ values were reported.

The results were summarized and shown in FIGS. 1A-1D, 2A-2C and 3A-3D.

It can be seen from FIGS. 1A-1D that the anti-IL6R antibodies of the disclosure specifically bound to human IL6R with higher Bmax (maximal binding) and lower $EC_{50}$ compared to Tocilizumab, suggesting that they more efficiently bound to more IL6R.

Figure 2A:
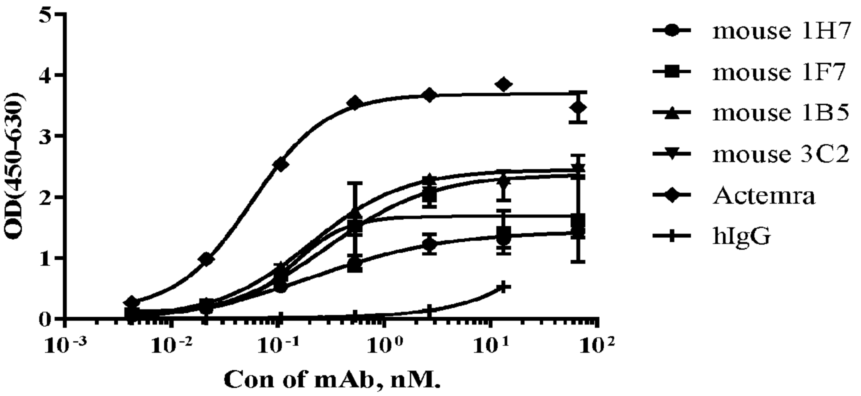
FIGS. 2A-2C show the binding capacities of mouse antibodies 1H7, 1F7, 1B5 and 3C2 (A), 1A3, 1D4 and 1G8 (B), 1H9 and 1G1 (C) to macaca IL6R in the indirect ELISA.
Figure 2B:
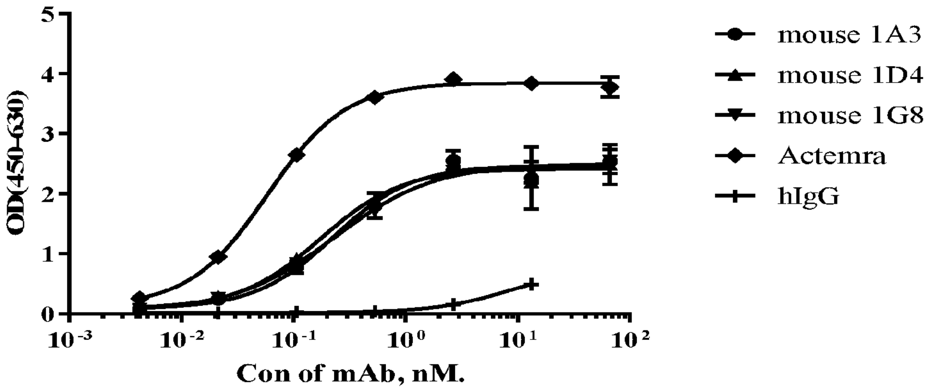
Figure 2C:
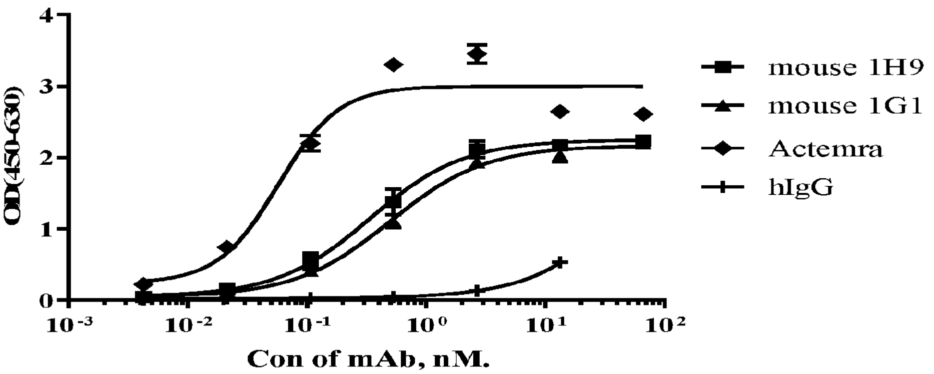
Figure 3A:
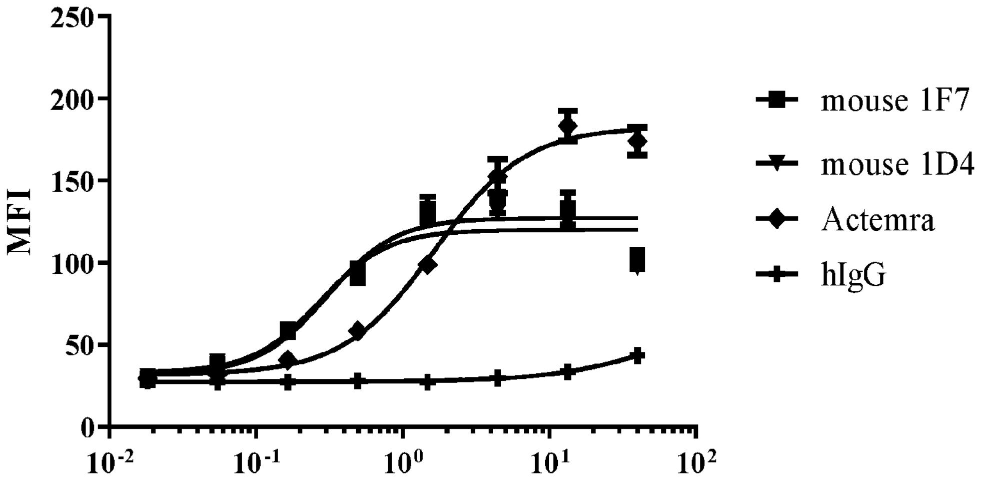
FIGS. 3A-3D show the binding capacities of mouse antibodies 1F7 and 1D4 (A), 1A3, 1G8 and 1B5 (B), 3C2 and 1G1 (C), 1H9 and 1H7 (D) to U266 cells expressing human IL6R in the cell-based binding FACS assay.
Figure 3B:
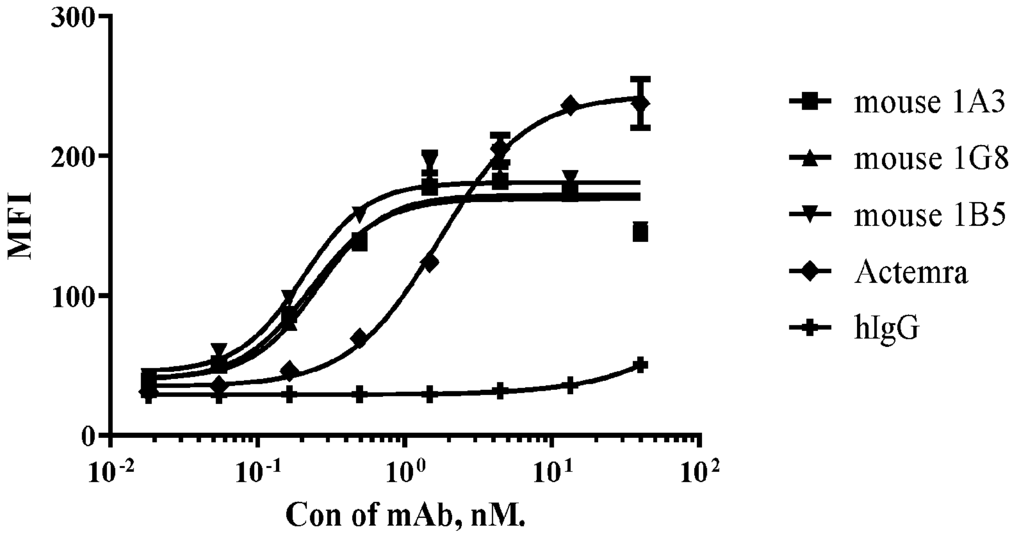
Figure 3C:
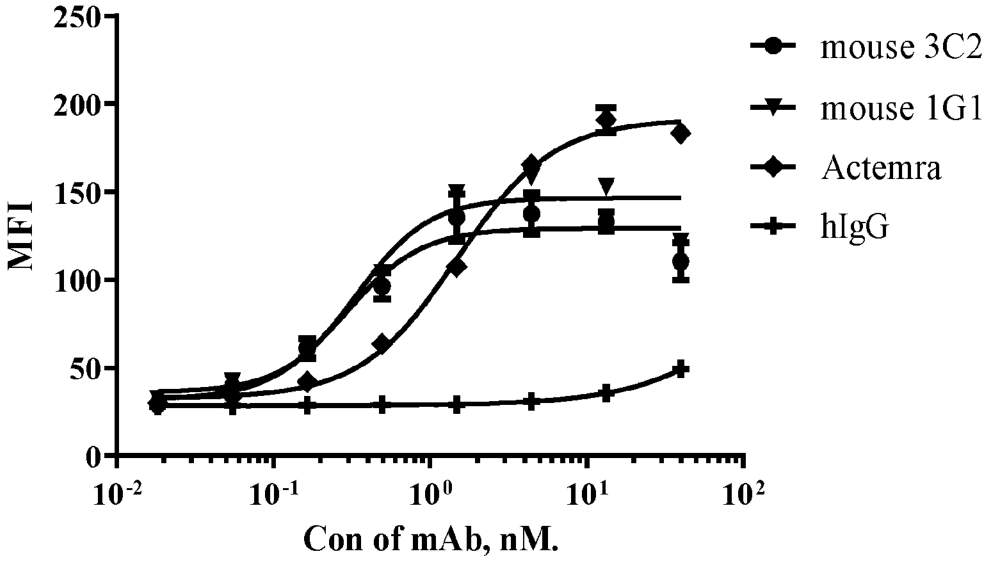
Figure 3D:
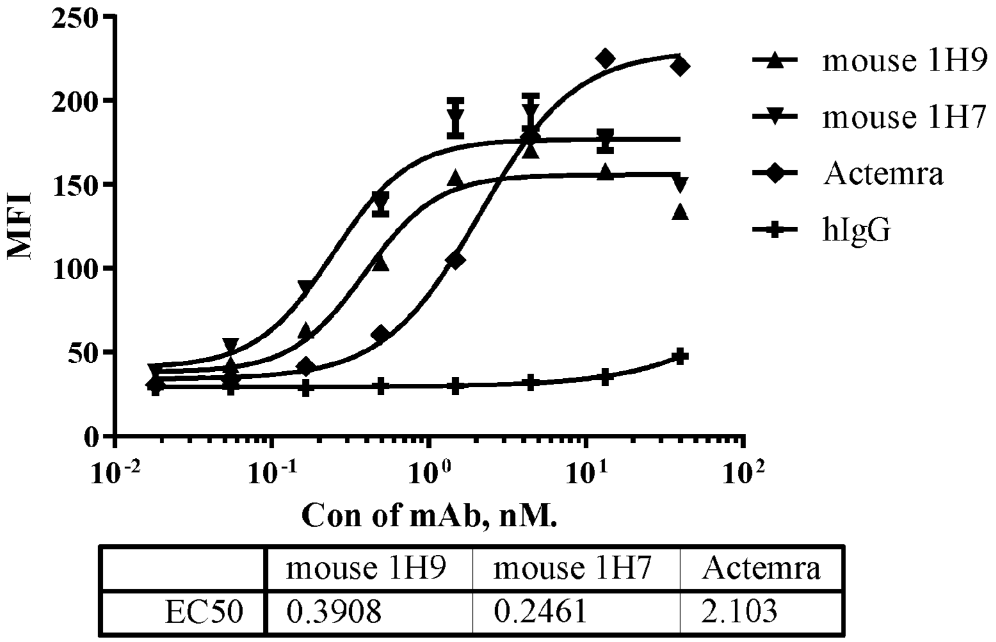
Figure 4A:
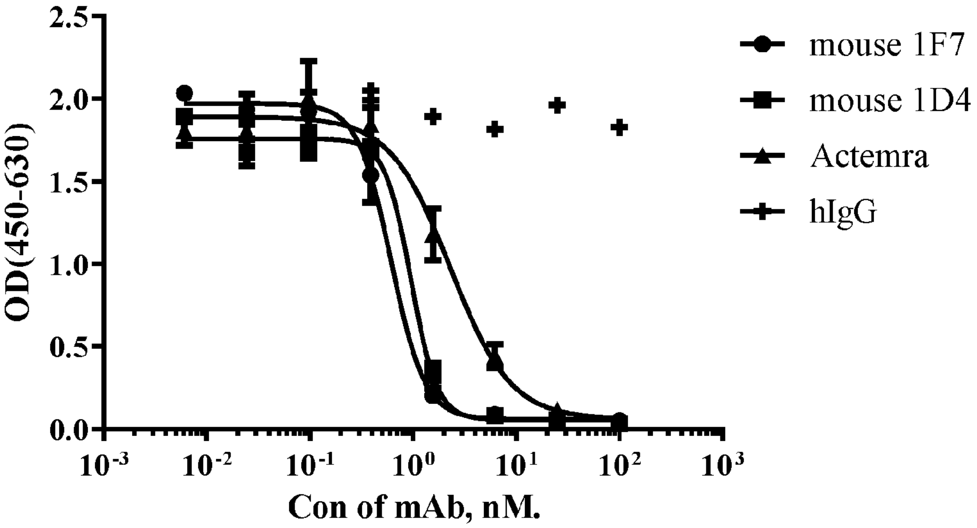
FIGS. 4A-4D show the blocking abilities of mouse antibodies 1F7 and 1D4 (A), 1A3, 1G8 and 1B5 (B), 3C2 and 1G1 (C), 1H9 and 1H7 (D) on human IL6R-IL6 binding in the ligand blocking ELISA.
Figure 4B:
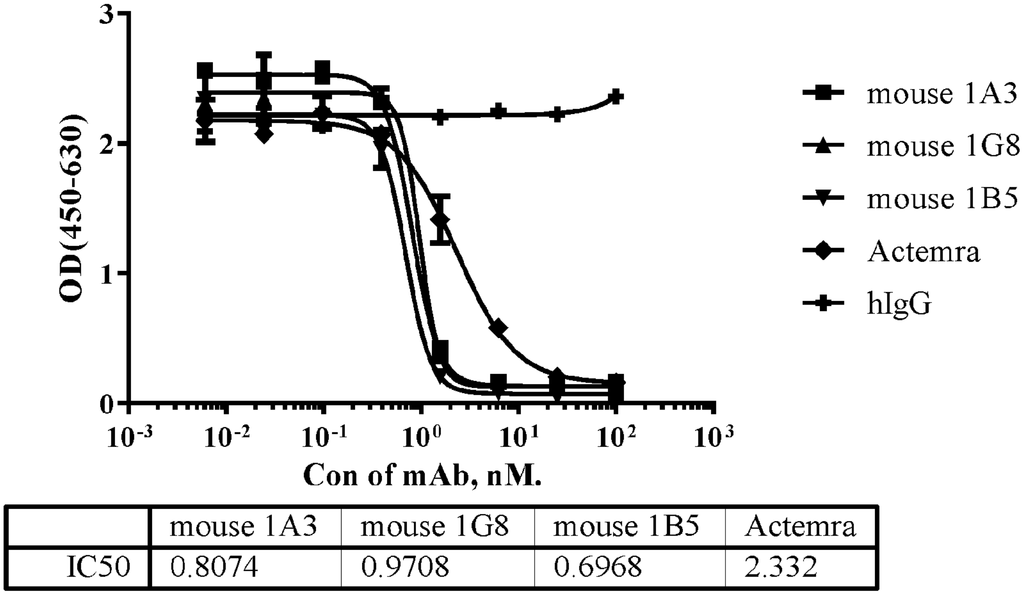
Figure 4C:
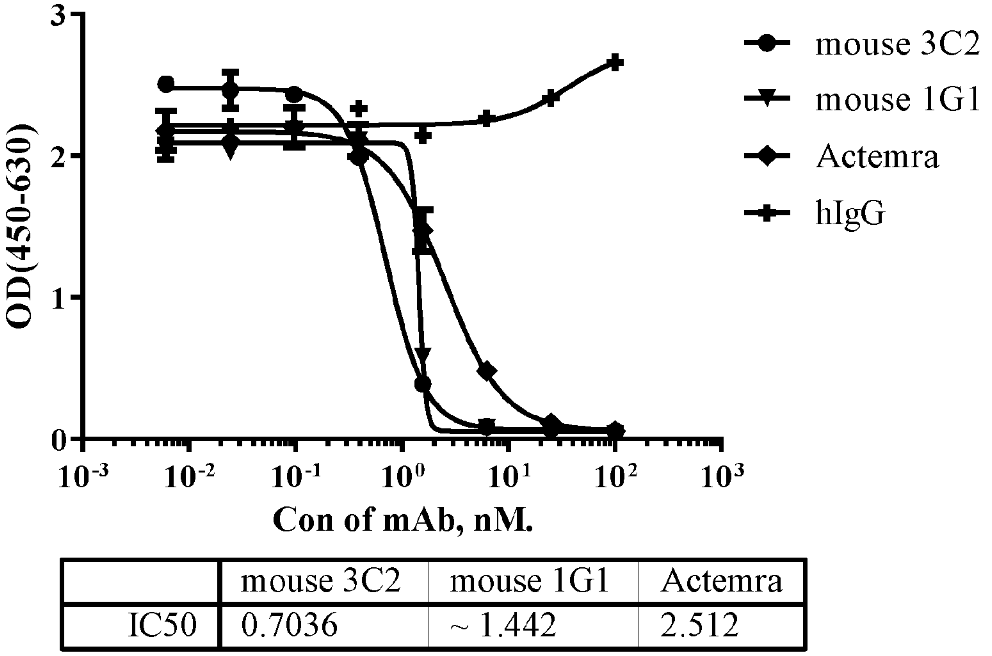
Figure 4D:
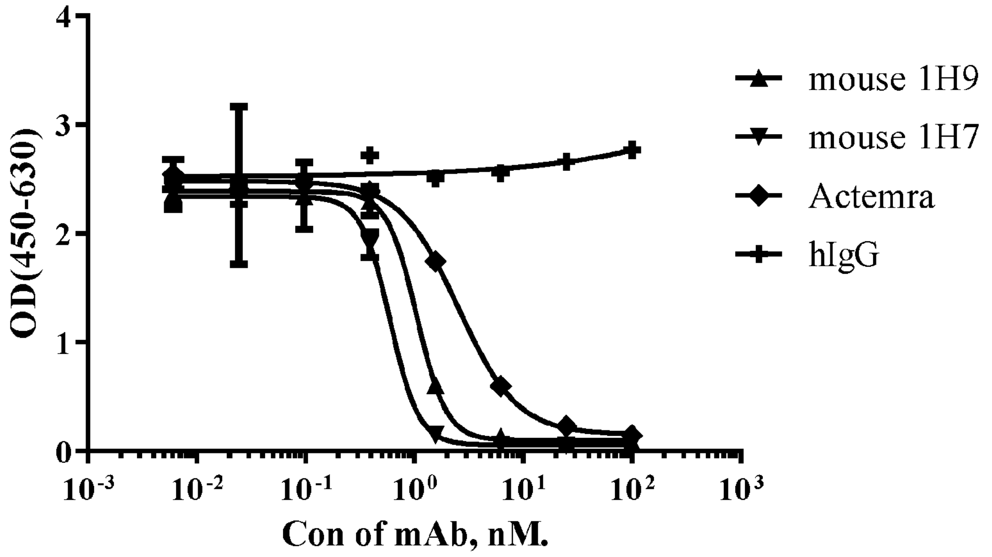
Figure 5A:
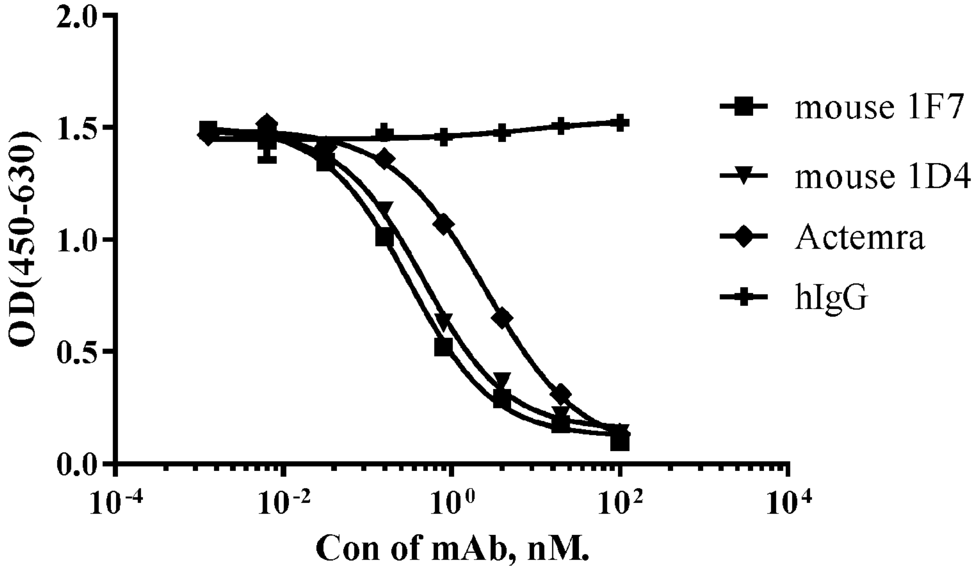
FIGS. 5A-5D show the abilities of mouse antibodies 1F7 and 1D4 (A), 1A3, 1G8 and 1B5 (B), 3C2 and 1G1 (C), 1H9 and 1H7 (D) to block benchmark-human IL6R binding in the benchmark blocking ELISA.
Figure 5B:
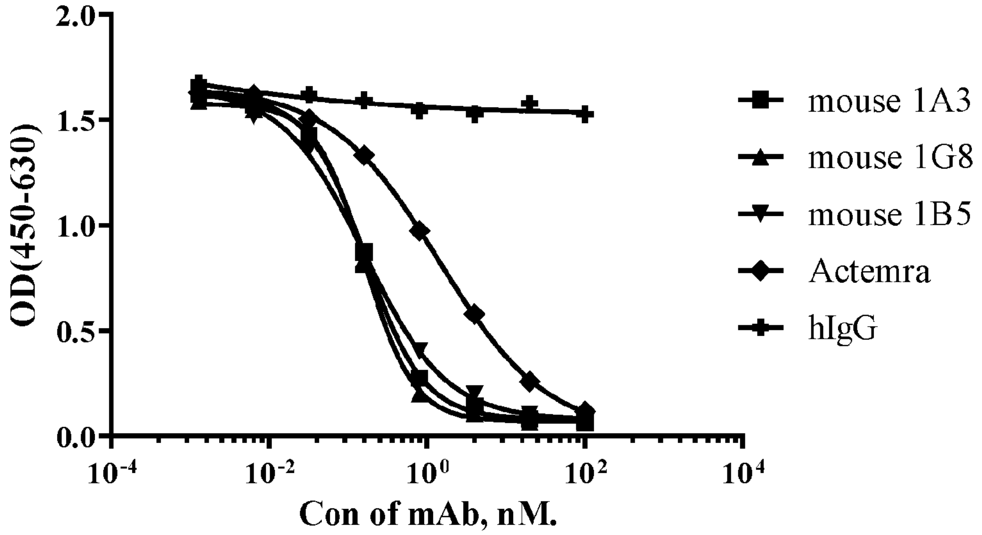
Figure 5C:
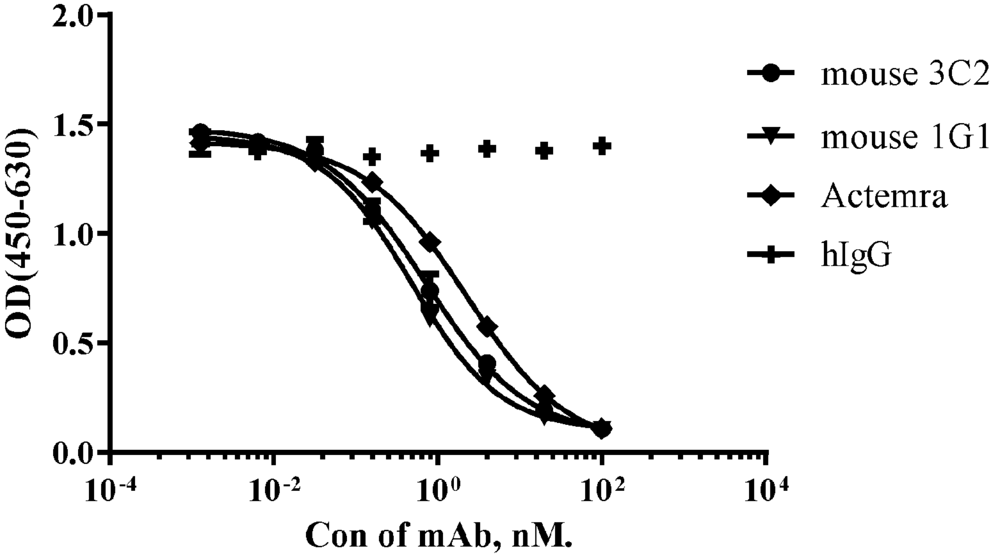
Figure 5D:
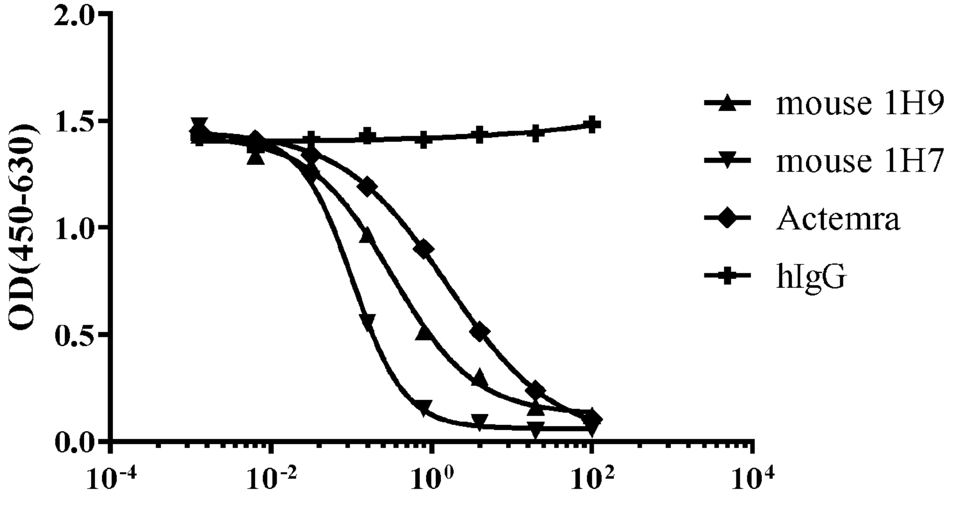
Figure 6A:
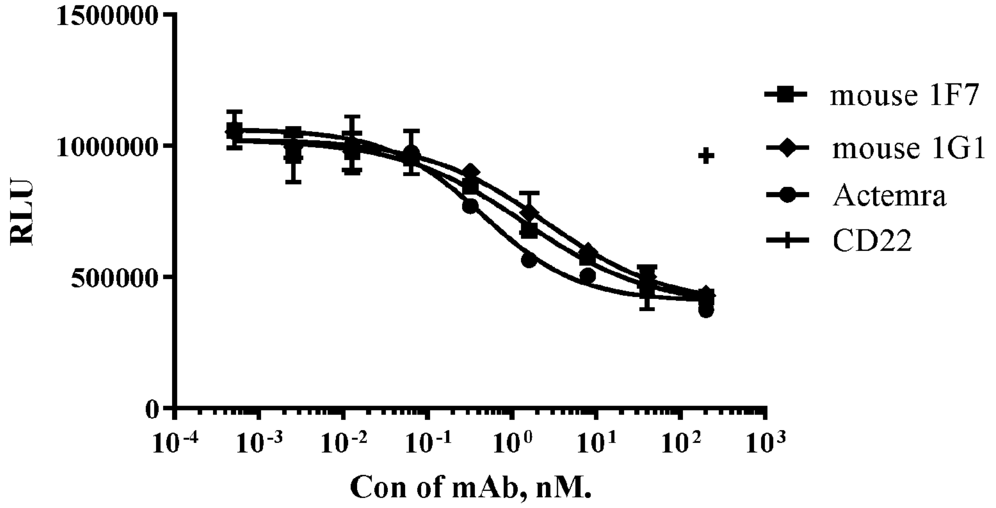
FIGS. 6A-6E show the inhibitory effects of mouse antibodies 1F7 and 1G1 (A), 1D4 and 1H9 (B), 1A3 and 1B5 (C), 1G8 and 1H7 (D), and 3C2 (E) on IL6 mediated proliferation of TF-1 cells in the cell based functional assay.
Figure 6B:
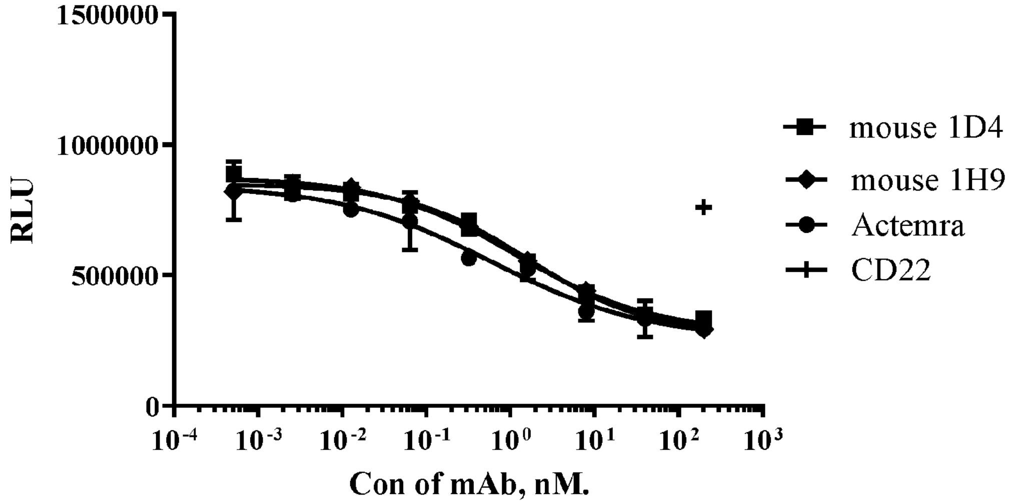
Figure 6C:
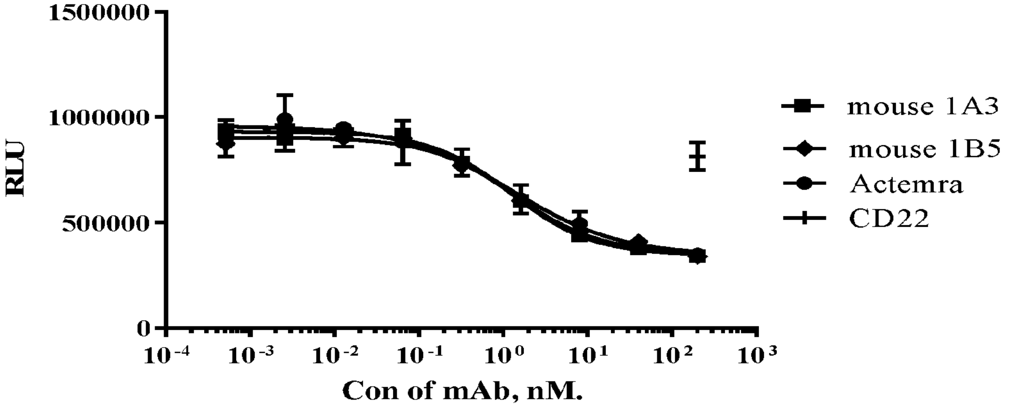
Figure 6D:
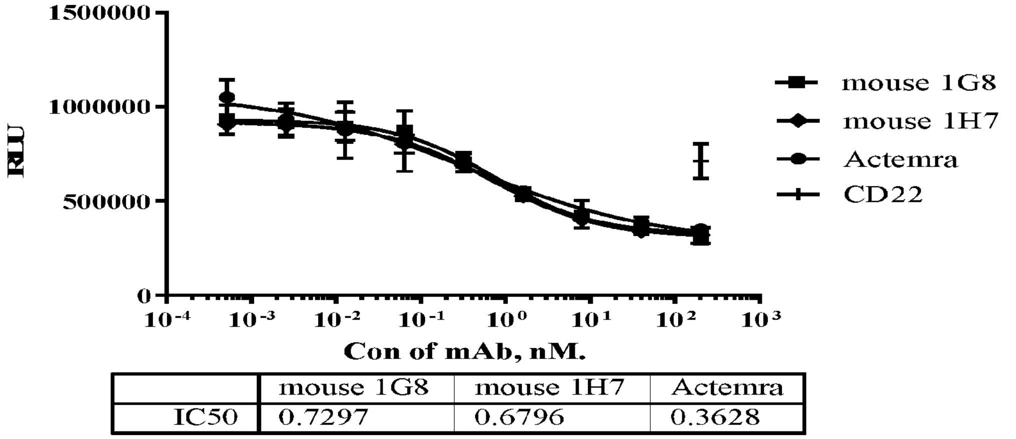
Figure 6E:
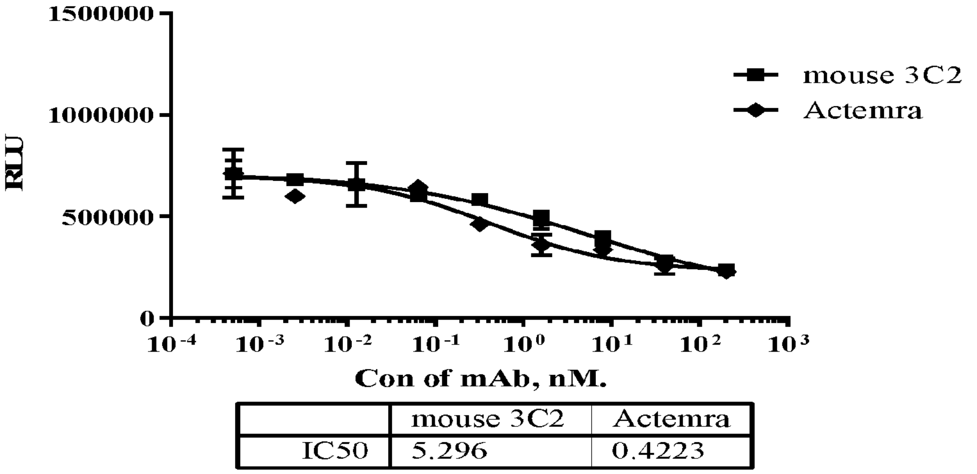
Figure 7A:
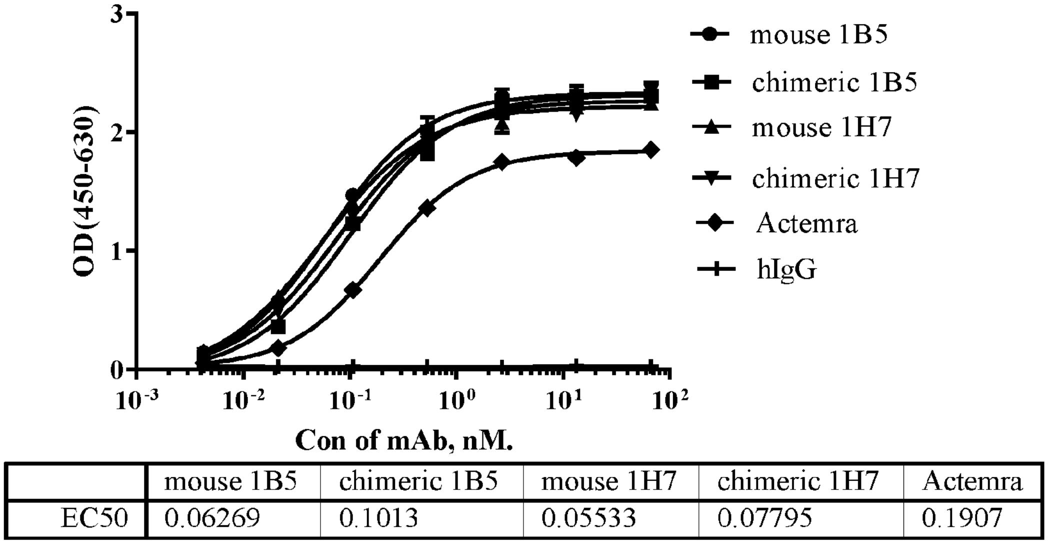
FIGS. 7A-7B show the binding capacities of chimeric antibodies 1B5 and 1H7 (A), and 1H9 (B) to human IL6R in the capture ELISA.
Figure 7B:
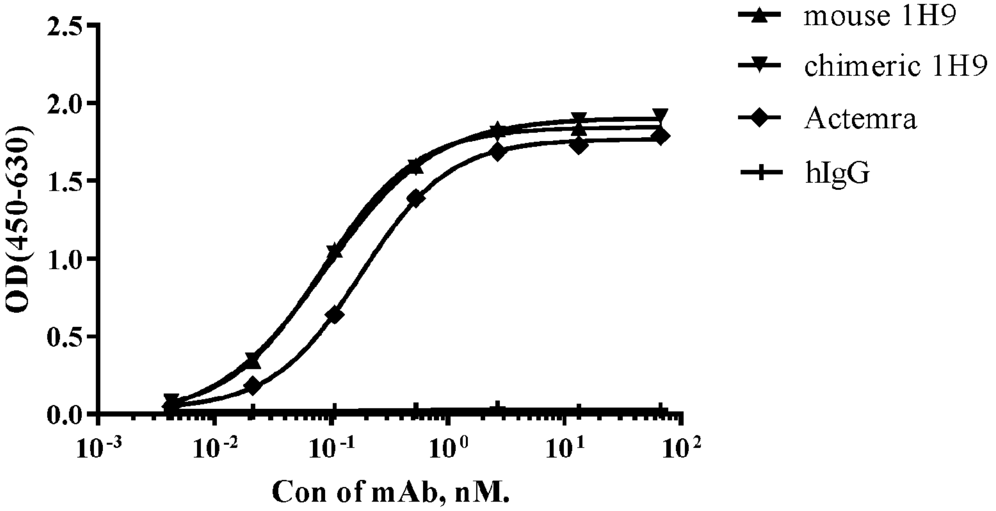
Figure 8A:
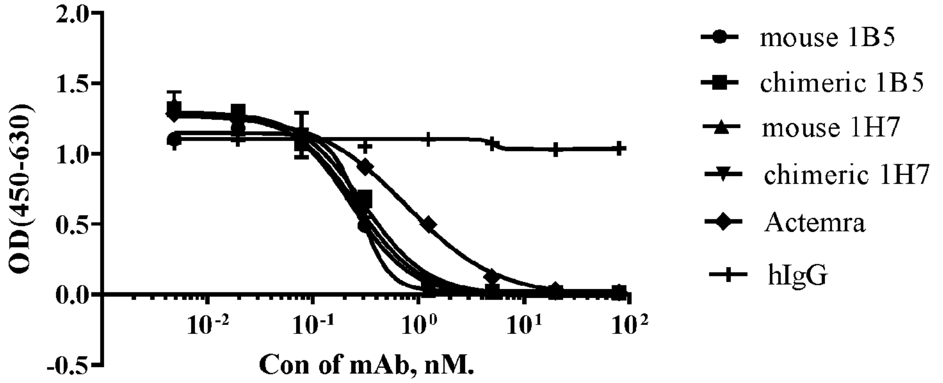
FIGS. 8A-8B show the blocking abilities of chimeric antibodies 1B5 and 1H7 (A), and 1H9 (B) on human IL6R-IL6 binding in the ligand blocking ELISA.
Figure 8B:
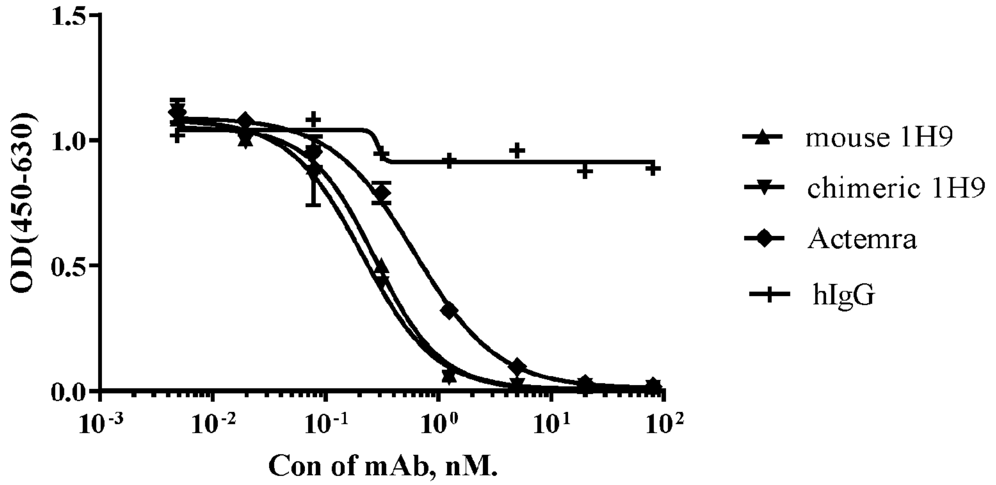
Figure 9A:
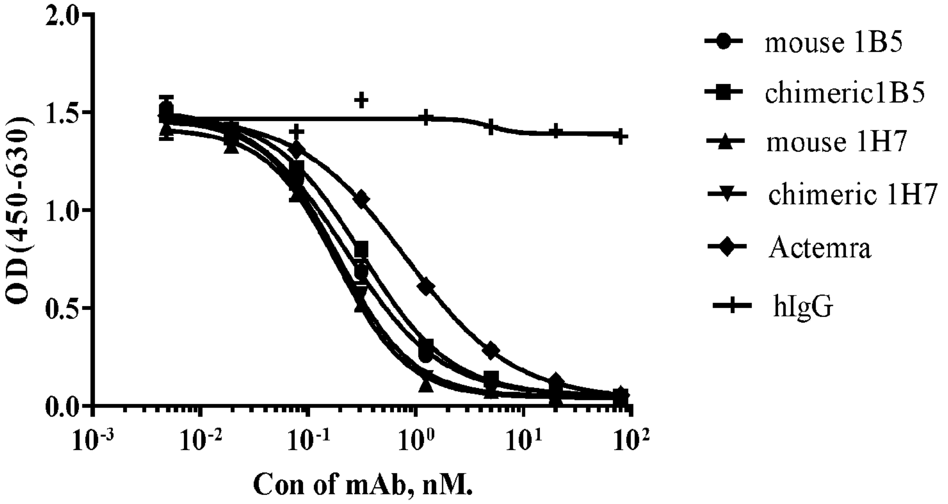
FIGS. 9A-9B show the abilities of chimeric antibodies 1B5 and 1H7 (A), and 1H9 (B) to block benchmark-human IL6R binding in the benchmark blocking ELISA.
Figure 9B:
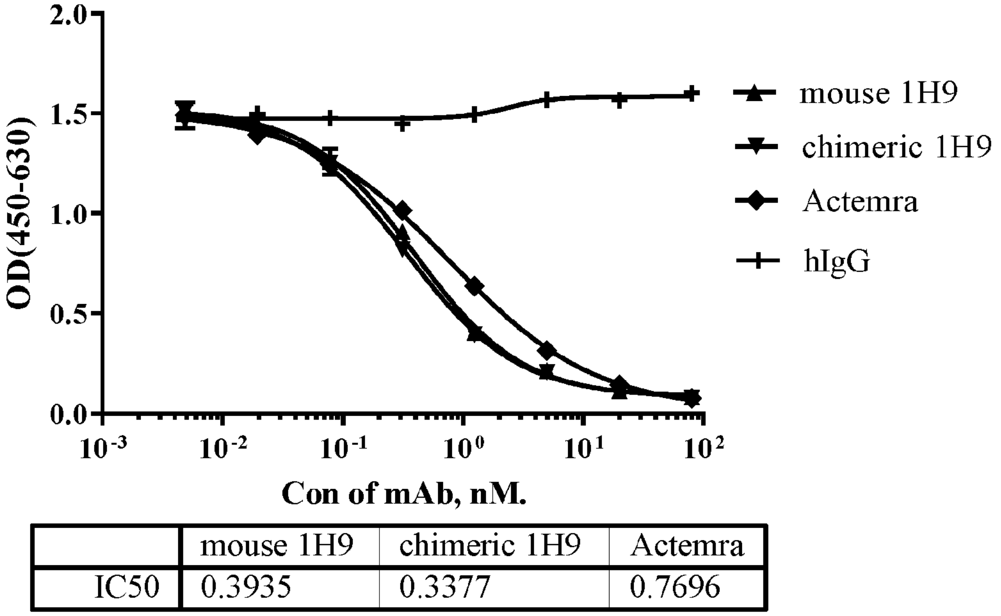
Figure 10:
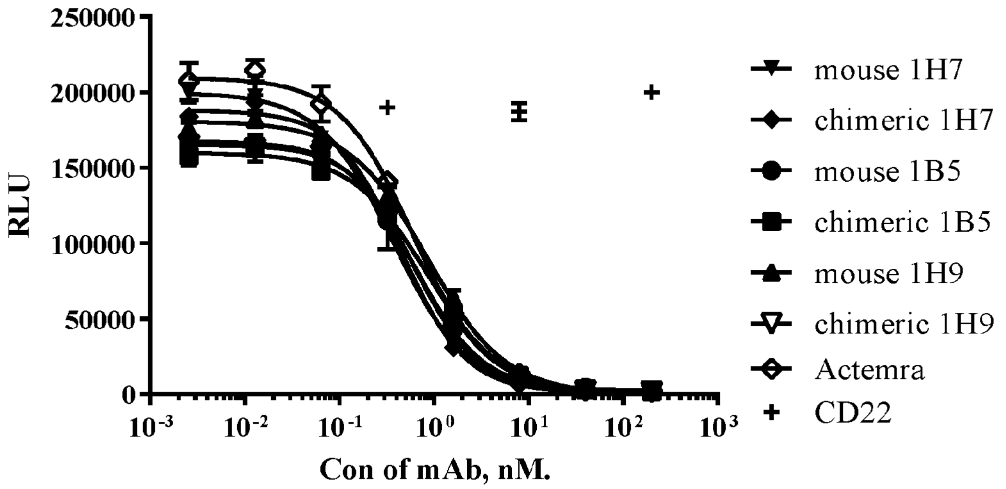
FIG. 10 shows the activities of chimeric antibodies 1H7, 1B5, and 1H9 on inhibiting IL6-mediated luciferase activity in the HEK293T-SIE-B4 reporter assay.

For the antibodies' binding activities to macaca IL6R, as shown in FIGS. 2A-2C, the Bmax was lower and $EC_{50}$ was higher for all as compared to Tocilizumab.

According to FIGS. 3A-3D, all antibodies of the disclosure bound to cell surface human IL6R more efficiently, although with a lower Bmax, as compared to Tocilizumab.

Example 4 Blocking Activities of Mouse Anti-IL6R Antibodies on IL6R-Tocilizumab or IL6R-IL6 Binding 4.1 Ligand Blocking ELISA The abilities of anti-IL6R antibodies of the disclosure to block IL6-IL6R binding were measured in a competitive ELISA assay. Briefly, human IL6 proteins (Sino biological Inc., Cat #10395-HNAE) were coated on 96-well micro plates at 2 μg/mL in carbonate/bicarbonate buffer (pH 9.6), 100 μl/well, for 2 hours at 37° C. ELISA plates were washed once with wash buffer (PBS+0.05% v/v Tween-20, PBST) and then blocked with 200 μl/well blocking buffer (5% w/v non-fatty milk in PBST) overnight at 4° C.

The next day, anti-IL6R antibodies or controls were diluted with biotin labeled human IL6R-Fc protein (prepared in house, SEQ ID NO: 43, 39.5 ng/ml in 2.5% w/v non-fatty milk in PBST), starting at 100 nM with a 4-fold serial dilution, and incubated at room temperature for 40 minutes. After plate washing for 4 times, the antibody/IL6R-Fc mixtures were added to human IL6 coated plates, 100 μl per well, and incubated for 40 minutes at 37° C. Plates were washed for 4 times using wash buffer, and added and incubated with 100 μl/well of streptavidin conjugated HRP (1:10000 dilution in PBST buffer, Jackson ImmunoResearch Laboratories, Inc., Cat #016-030-084) for 40 minutes at 37° C. Plates were washed again using wash buffer. Finally, TMB was added and the reaction was stopped using 1M $H_2SO_4$. The absorbance was read on a microplate reader using dual wavelength mode with 450 nm for TMB and 630 nm as the reference wavelength, and then the OD (450-630) values were plotted against antibody concentration. Data was analyzed using Graphpad Prism software and $IC_{50}$ values were reported.

4.2 Benchmark Blocking ELISA

The abilities of anti-IL6R antibodies of the disclosure to block binding of benchmark (Tocilizumab) to human IL6R protein were measured in a competitive ELISA assay. Briefly, the benchmark was coated on 96-well micro plates at 2 μg/mL in PBS, 100 μl/well, and incubated for 2 hours at 37° C. ELISA plates were washed once with wash buffer (PBS+0.05% v/v Tween-20, PBST) and then blocked with 200 μl/well blocking buffer (5% w/v non-fatty milk in PBST) overnight at 4° C.

The next day, the anti-IL6R antibodies of the disclosure or controls were diluted with biotin labeled human IL6R-Fc protein (SEQ ID NO: 43, 13.6 ng/ml in 2.5% w/v non-fatty milk in PBST), starting at 100 nM with a 5-fold serial dilution, and incubated at room temperature for 40 minutes. After plate washing for 4 times, the antibody/IL6R-Fc mixtures were added to the benchmark coated plates, 100 μl per well. After incubation at 37° C. for 40 minutes, plates were washed 4 times using wash buffer. Then streptavidin conjugated HRP was added, and the plates were incubated for 40 minutes at 37° C. The plates were finally washed using wash buffer, and added with TMB. The reaction was stopped using 1M $H_2SO_4$, and the absorbance was read on a microplate reader using dual wavelength mode with 450 nm for TMB and 630 nm as the reference wavelength. The OD (450-630) values were plotted against antibody concentration. Data was analyzed using Graphpad Prism software and $IC_{50}$ values were reported.

The results of the two assays were shown in FIGS. 4A-4D and 5A-5D.

It can be seen from FIGS. 4A-4D that all anti-IL6R antibodies of the disclosure were capable of blocking human IL6-human IL6R binding more efficiently at lower $IC_{50}$ as compared to Tocilizumab.

FIGS. 5A-5D showed that all the anti-IL6R antibodies of the disclosure were able to block IL6R binding to Tocilizumab, suggesting that these antibodies might bind to the same or similar epitope as Tocilizumab did.

Example 5 Cell Based Functional Assay of Mouse Anti-IL6R Antibodies

All anti-IL6R antibodies of the disclosure were further tested for the inhibitory effects on IL6 induced TF-1 cell proliferation.

Briefly, $8\times10^3$ TF-1 cells (human premyeloid cell line, ATCC® CRL-2003) at the log phase stage in 100 μL RPMI1640 medium (Gibco, Cat #A10491-01) supplemented with 10% v/v FBS (Gibco, Cat #10099-141) were plated into 96-well plates. Then, the plates were added with 50 μl serially diluted anti-IL6R antibodies of the disclosure or controls (including an in house made anti-CD22 antibody as a negative control) (starting from 800 nM, 5-fold serial dilution with the culture medium), and incubated at 37° C. for 30 minutes. The plates were then added with 50 μl human IL6 protein (Sino biological, Cat #10395-HNAE, 6.4 ng/mL in the culture medium), and then put in a 5% $CO_2$ incubator at 37° C. for 4 days. The plates were centrifuged and the supernatants were discarded. Then, the plates were added with the reagents of Cell Titer-Glo® Luminescent Cell Viability Assay (Promega, Cat #G7572, 50 μl/well) and incubated for 10 minutes at 25° C. Chemiluminescence was measured using a Tecan Infinit® 200 Pro equipment. Data was analyzed using Graphpad Prism software and $IC_{50}$ values were reported.

The results of the assay were shown in FIGS. 6A-6E.

It can be seen that all anti-IL6R antibodies were able to inhibit IL-6 induced TF-1 cell growth, at comparable or a bit lower activities as compared to Tocilizumab.

Example 6 Generation and Characterization of Chimeric Antibodies

The heavy and light chain variable regions of the anti-IL6R mouse mAbs were sequenced, and the sequence ID numbers were summarized in Table 1.

The heavy and light chain variable regions of the of the anti-IL6R mouse mAbs 1B5, 1H9 and 1H7 were cloned in frame to human IgG1 heavy-chain (SEQ ID NO.: 41) and human kappa light-chain constant regions (SEQ ID NO.: 42), respectively, wherein the C terminus of variable region was linked to the N terminus of the respective constant region.

The vectors each containing a nucleotide encoding a heavy chain variable region linked to human IgG1 heavy-chain constant region, and the vectors each containing a nucleotide encoding a light chain variable region linked to human kappa light-chain constant region were transiently transfected into 50 ml of 293F suspension cell cultures in a ratio of 1.1:1 light to heavy chain construct, with 1 mg/mL PEI.

Cell supernatants were harvested after six days in shaking flasks, spun down to pellet cells, and then chimeric antibodies were purified from cell supernatants as described above. The purified antibodies were tested in the capture ELISA, competitive ELISA, BIAcore affinity test and cell-based reporter assay following the protocols in the foregoing Examples with or without modifications as well as protocols described below.

For the reporter assay, an in house made cell line HEK293T-SIE-B4 with SIE (sis-inducible element) driven luciferase reporter gene luc2P (Photinus pyralis) was used. The HEK293T-SIE-B4 cells were prepared, following the instruction of lipofectamine 3000 transfection reagent (Thermo Fisher), by transfecting HEK293T cells with pGL4.47[luc2P/SIE/Hygro] vector (Promega, Cat #E404A). Briefly, $2\times10^4$ HEK293T-SIE-B4 cells in 100 μl DMEM medium (Gibco, Cat #10566-016) supplemented with 10% v/v FBS (Gibco, Cat #10099-141) and 10% w/v Sodium Pyruvate (Gibco, Cat #1360-070) were plated into each well of 96 well-plates (Corning, Cat #3903). Then, the plates were added with 50 μl serially diluted chimeric anti-IL6R antibodies of the disclosure or controls (including an in house made anti-CD22 antibody as a negative control) (starting from 800 nM, 5-fold serial dilution in the culture medium), and incubated at 37° C. for 30 minutes. The plates were then added with 50 μl human IL6 protein (Sino biological, Cat #10395-HNAE, 4 ng/mL in the culture medium), and then placed in a 5% $CO_2$ incubator at 37° C. for 24 hours. The plates were centrifuged, and 100 μl supernatant was discarded per well. Luciferase detection Reagent (50 μL/well, Promega, Cat #E6120) was added. Within five minutes, the plates were subject to analysis by Tecan infinite 200Pro plate-reader. Data was analyzed using Graphpad Prism software and $IC_{50}$ values were reported.

For the capture ELISA, AffiniPure Goat Anti-Human IgG, $F(ab')_2$ fragment specific (Jackson Immuno Research, Cat #109-005-097) was used instead of AffiniPure Goat Anti-Mouse IgG, $F(ab')_2$ fragment specific, 100 μl/well.

For the BIAcore, goat anti-human IgG (GE healthcare, Cat #BR100839, Human Antibody Capture Kit) was covalently linked to a CM5 chip instead of goat anti-mouse IgG, and a CM5 chip was used for Tocilizumab instead of a Protein G chip. The recombinant human IL6R-his (amino acid sequence set forth in SEQ ID NO: 44) at the concentration of 100 nM instead of serially diluted recombinant human IL6R-his, was flowed onto the chip at a flow rate of 30 μL/min.

The results were shown in Table 4 and FIGS. 7A-7B, 8A-8B, 9A-9B and 10.

TABLE 4

Binding Affinity of Chimeric Anti-IL6R Antibodies to Human IL6R

| | BIAcore Affinity to human IL6R | | |
|---|---|---|---|
| Clone ID | $K_a$ ($M^{-1}s^{-1}$) | $K_d$ ($s^{-1}$) | $K_D$ (M) |
| Chimeric 1B5 | 2.12E+05 | 1.94E−04 | 9.15E−10 |
| Chimeric 1H7 | 1.30E+05 | 5.21E−05 | 4.00E−10 |
| Chimeric 1H9 | 2.122E+5 | 1.942E−4 | 9.151E−10 |
| Tocilizumab | 1.01E+05 | 3.28E−04 | 3.26E−09 |

The data showed that the chimeric anti-IL6R antibodies had similar binding affinities/capacities to human IL6R and similar blocking activities on IL6-IL6R interaction to their parental mouse mAbs, which were comparable to tocilizumab in the cell based reporter assay (see FIG. 10) and better than tocilizumab in the other assays (see FIGS. 7A-7B, 8A-8B and 9A-9B).

Example 7 Humanization of Anti-IL6R Antibody 1H7

Mouse anti-IL6R antibody 1H7 was humanized and further characterized. Humanization of the antibody was conducted using the well-established CDR-grafting method as described in detail below.

To select acceptor frameworks for humanization of mouse antibody 1H7, the light and heavy chain variable region sequences of 1H7 were blasted against the human immunoglobulin gene database. The human germlines with the highest homology were selected as the acceptor frameworks for humanization. The antibody heavy/light chain variable region CDRs were inserted into the selected frameworks, and the residue(s) in the frameworks was/were further back mutated to obtain more candidate heavy chain/light chain variable regions. A total of 13 exemplary humanized 1H7 antibodies, namely hu1H7-V1 to hu1H7-V12 and hu1H7-V1-2, were obtained whose heavy/light chain variable region sequence ID numbers were in Table 1.

The vectors each containing a nucleotide encoding a humanized heavy chain variable region linked to human IgG1 heavy-chain constant region (SEQ ID NO: 41), and the vectors each containing a nucleotide encoding a humanized light chain variable region linked to human kappa light-chain constant region (SEQ ID NO: 42) were transiently transfected into 50 ml of 293F suspension cell cultures in a ratio of 1.1:1 light to heavy chain construct, with 1 mg/mL PEI.

Example 8 Characterization of Exemplary Humanized Antibodies

Cell supernatants containing humanized antibodies were harvested after six days in shaking flasks and directly subjected to BIAcore test following the protocol described above with modifications. In specific, goat anti-human IgG (GE healthcare, Cat #BR100839, Human Antibody Capture Kit) was covalently linked to a CM5 chip instead of goat anti-mouse IgG, and a CM5 chip was used for Tocilizumab instead of a Protein G chip. The chimeric antibody and Tocilizumab were prepared in HBS-EPV at 10 μg/ml concentration, and cell supernatants containing humanized antibodies were diluted 10 times. The $K_a$, $K_d$ and $K_D$ values were determined and summarized in Table 5 below.

The data indicated that the exemplary humanized antibodies had similar human IL6R binding affinities to the chimeric antibody, which were higher than that of Tocilizumab.

TABLE 5

Biacore Kinetics of Exemplary Humanized Anti-IL6R monoclonal Antibodies Binding to Human IL6R

| | Kinetics on BIAcore Human IL6R | | |
|---|---|---|---|
| Clone ID | $K_a$ ($M^{-1}s^{-1}$) | $K_d$ ($s^{-1}$) | $K_D$ (M) |
| Chimeric 1H7 | 2.04E+05 | 1.23E−04 | 6.04E−10 |
| hu1H7-V1 | 2.58E+05 | 1.73E−04 | 6.69E−10 |
| hu1H7-V1-2 | 2.62E+05 | 1.65E−04 | 6.30E−10 |
| hu1H7-V2 | 2.69E+05 | 1.97E−04 | 7.33E−10 |
| hu1H7-V3 | 3.11E+05 | 1.76E−04 | 5.68E−10 |
| hu1H7-V4 | | Not tested | |
| hu1H7-V5 | 3.70E+05 | 1.95E−04 | 5.26E−10 |
| hu1H7-V6 | 3.34E+05 | 1.95E−04 | 5.84E−10 |
| hu1H7-V7 | 2.33E+05 | 1.99E−04 | 8.55E−10 |
| hu1H7-V8 | 2.18E+05 | 1.99E−04 | 9.10E−10 |
| hu1H7-V9 | 2.12E+05 | 2.22E−04 | 1.05E−09 |
| hu1H7-V10 | | Not tested | |
| hu1H7-V11 | 2.38E+05 | 2.02E−04 | 8.49E−10 |
| hu1H7-V12 | 2.79E+05 | 2.07E−04 | 7.44E−10 |
| Tocilizumab | 1.30E+05 | 4.94E−04 | 3.81E−09 |

The humanized antibody hu1H7-V5 was purified as described above and tested in Biacore, capture ELISA, indirect ELISA, cell-based binding FACS, competitive ELISA and cell-based reporter assay, following the protocols in the foregoing Examples with minor modifications described below.

For the capture ELISA, 96-well micro plates were coated with 2 μg/ml goat anti-human IgG (AffiniPure Goat Anti-Human IgG, $F(ab')_2$ fragment specific, Jackson ImmunoResearch Laboratories, Inc., Cat #109-005-097) instead of goat anti-mouse IgG $F(ab')_2$ fragment, 100 μl/well.

For the Indirect ELISA, Peroxidase AffiniPure $F(ab')_2$ Fragment Goat Anti-Human IgG, Fcγ Fragment Specific (Jackson ImmunoResearch Laboratories, Inc., Cat #109-036-098) was used instead of Peroxidase AffiniPure Goat Anti-Mouse IgG, Fcγ Fragment Specific, 100 μl/well.

For the BIAcore, goat anti-human IgG (GE healthcare, Cat #BR100839, Human Antibody Capture Kit) was covalently linked to a CM5 chip instead of goat anti-mouse IgG, a CM5 chip was used for the Tocilizumab instead of a Protein G chip.

For the cell-based binding FACS, R-Phycoerythrin AffiniPure Goat Anti-human IgG Fcγ fragment specific (Jackson ImmunoResearch Laboratories, Inc., Cat #109-115-098) was used instead of R-Phycoerythrin AffiniPure $F(ab')_2$ Fragment Goat Anti-Mouse IgG (H+L), 1:1000 dilution in FACS buffer, 100 μl/well.

The humanized antibody hu1H7-V5 was also tested in the thermal stability assay to determine Tm (melting temperature) using a GloMelt™ Thermal Shift Protein Stability Kit (Biotium, Cat #33022-T). Briefly, the GloMelt™ dye was allowed to thaw and reach room temperature. The vial containing the dye was vortexed and centrifuged. Then, 10× dye was prepared by adding 5 μL 200× dye to 95 μL PBS. 2 μL 10× dye and 10 μg humanized antibodies were added, and PBS was added to a total reaction volume of 20 μL. The tubes containing the dye and antibodies were briefly spun and placed in real-time PCR thermos-cycler (Roche, LightCycler 480 II) set up with a melt curve program having the parameters in Table 6.

TABLE 6

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA |

The results were shown in Table 7 and FIGS. 11 to 17.

According to the data, the humanized antibody hu1H7-V5 showed higher binding affinity/activity to human IL6R and higher IL6R-IL6 blocking capacity when compared to Tocilizumab. In particular, the antibody hu1H7-V5 exhibited better bioactivity on inhibiting IL6-mediated luciferase activity in the HEK293T-SIE-B4 cell reporter assay than Tocilizumab.

TABLE 7

Binding Affinity of Humanized Antibody hu1H7-V5

| | Kinetics on Biacore | | | | | |
|---|---|---|---|---|---|---|
| | Human IL6R-his | | | Macaca-IL6R -his | | |
| Clone ID | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| Chimeric 1H7 | 1.32E+05 | 1.12E−04 | 8.50E−10 | 9.48E+04 | 1.12E−04 | 1.18E−09 |
| hu1H7-V5 | 1.45E+05 | 1.12E−04 | 7.73E−10 | 7.58E+04 | 1.20E−04 | 1.58E−09 |
| Tocilizumab | 5.49E+04 | 4.07E−04 | 7.42E−09 | 4.87E+04 | 4.46E−04 | 9.16E−09 |

It can be seen from Table 7 that the humanized antibody hu1H7-V5 showed comparable binding affinity to human and macaca IL6R compared to the chimeric antibody 1H7. In other words, the hu1H7-V5's binding affinity to human and macaca IL6R was higher than that of Tocilizumab.

Figure 11:
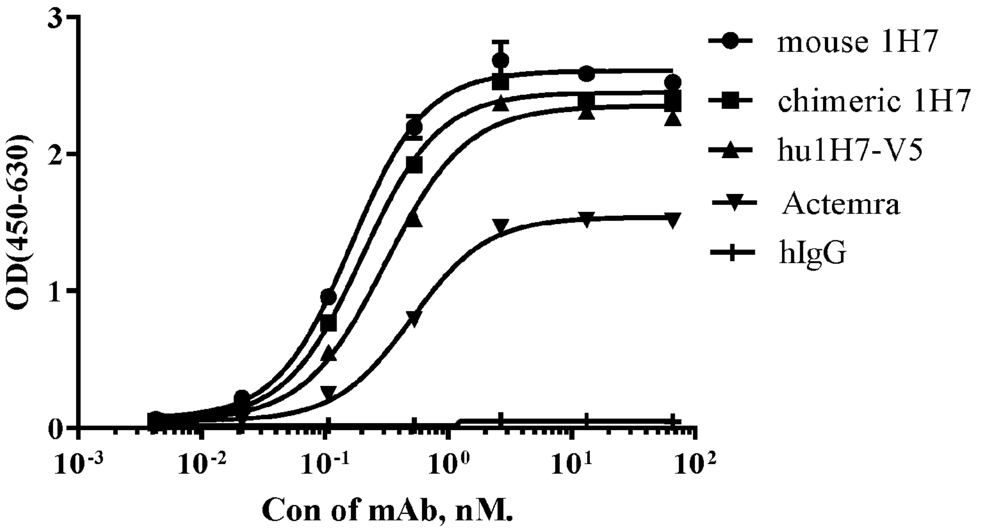
FIG. 11 shows the binding capacity of humanized antibody hu1H7-V5 to human IL6R in the capture ELISA.

It can be seen from FIG. 11 that the humanized antibody hu1H7-V5 specifically bound to human IL6R with higher Bmax (maximal binding) and lower $EC_{50}$ compared to Tocilizumab, suggesting that it more efficiently bound to more IL6R.

Figure 12:
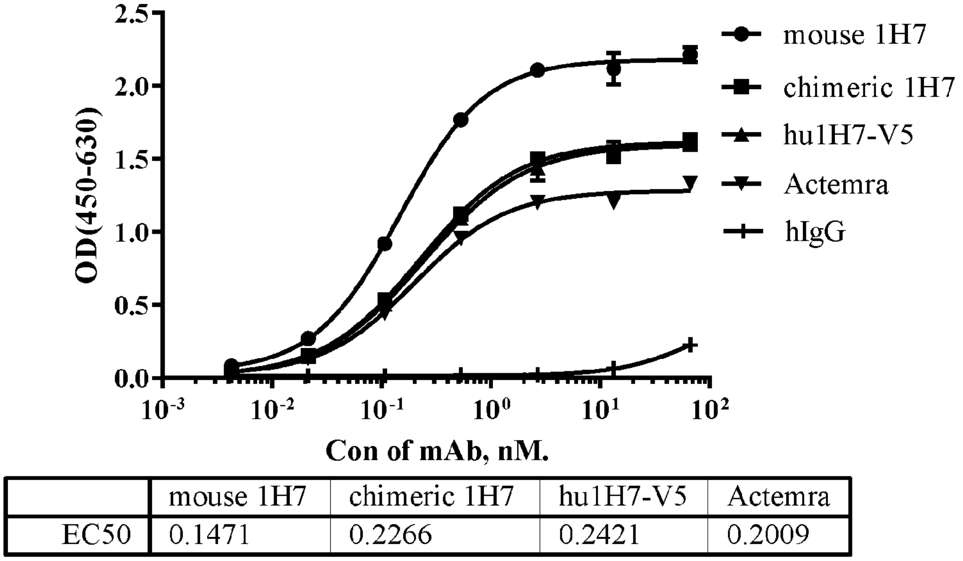
FIG. 12 shows the binding capacity of humanized antibody hu1H7-V5 to macaca IL6R in the indirect ELISA.

For the antibody's binding activity to macaca IL6R, as shown in FIG. 12, the Bmax was higher and $EC_{50}$ was lower as compared to Tocilizumab.

Figure 13:
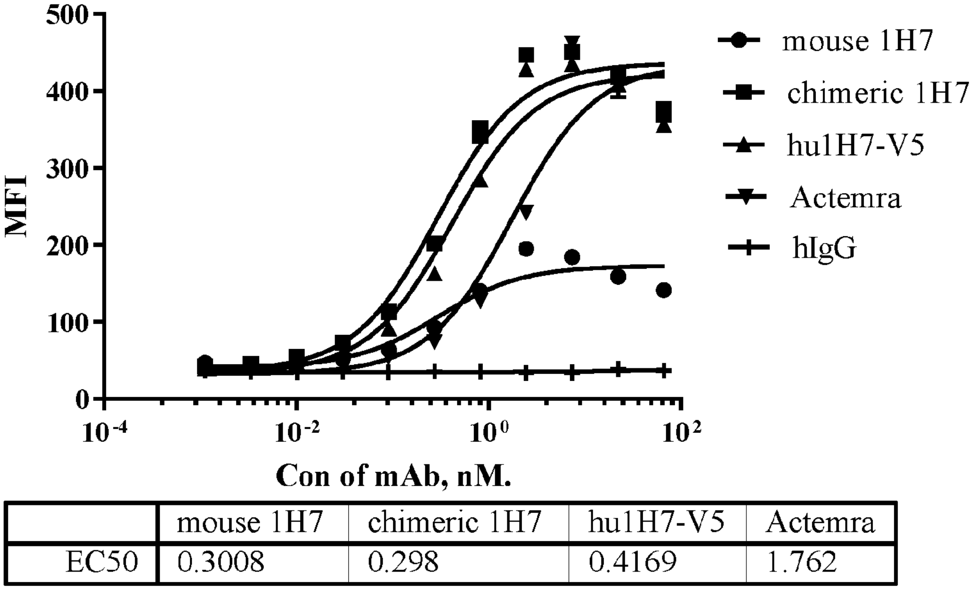
FIG. 13 shows the binding capacity of humanized antibody hu1H7-V5 to U266 cells expressing human IL6R in the cell-based binding FACS assay.

According to FIG. 13, the humanized antibody hu1H7-V5 bound to cell surface human IL6R more efficiently, with higher Bmax (maximal binding) and lower $EC_{50}$ than Tocilizumab, suggesting that it more efficiently bound to more IL6R.

Figure 14:
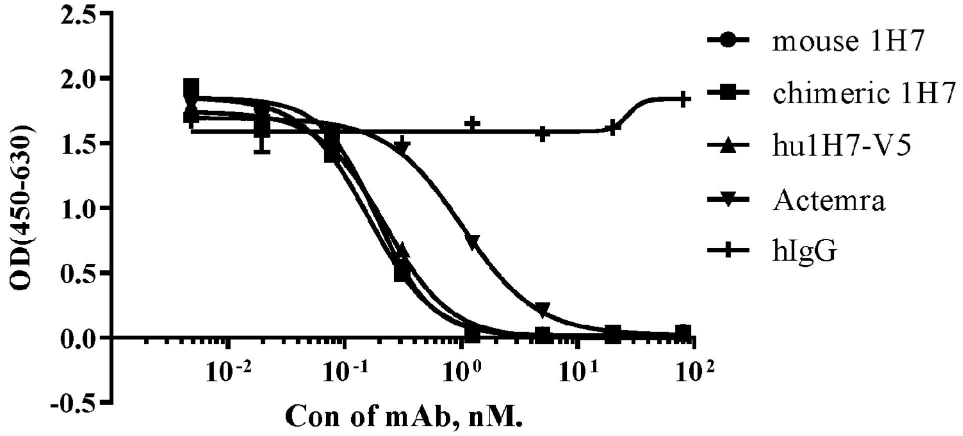
FIG. 14 shows the blocking ability of humanized antibody hu1H7-V5 on human IL6R-IL6 binding in the ligand blocking ELISA.

FIG. 14 showed that the humanized antibody hu1H7-V5 was capable of blocking IL6R-IL6 binding, and the blocking activity was higher than that of Tocilizumnab.

Figure 15:
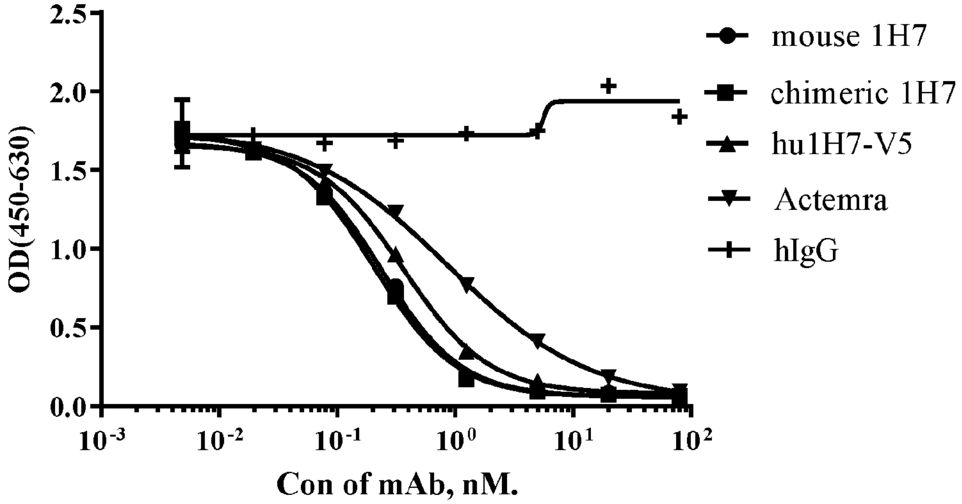
FIG. 15 shows the ability of humanized antibody hu1H7-V5 to block benchmark-human IL6R binding in the benchmark blocking ELISA.

According to FIG. 15, the humanized antibody hu1H7-V5 was able to block human IL6R-Tocilizumab binding, suggesting that hu1H7-V5 might bind to a similar epitope as Tocilizumnab did.

Figure 16:
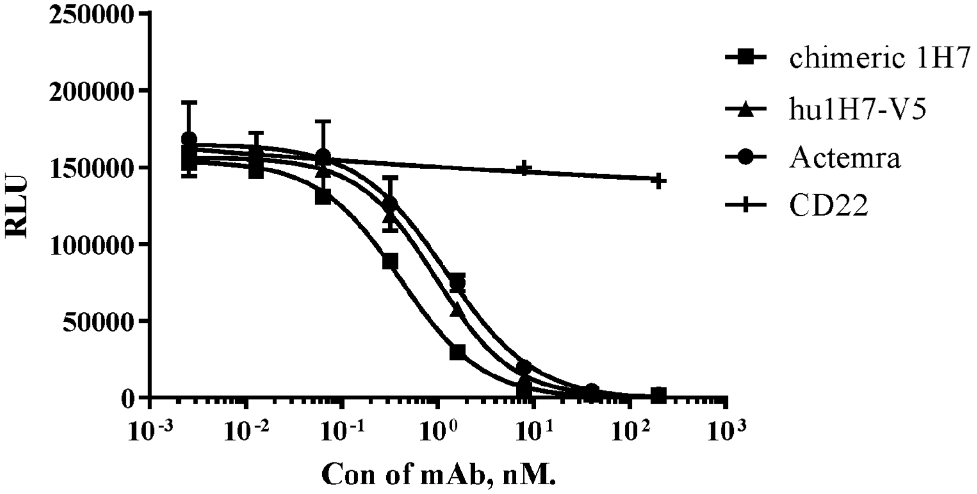
FIG. 16 shows the activity of humanized antibody hu1H7-V5 on inhibiting IL6-mediated luciferase activity in the HEK293T-SIE-B4 reporter assay.

As shown in FIG. 16, the humanized antibody hu1H7-V5 had higher functional activity in the cell-based reporter assay than Tocilizumab.

Figure 17:
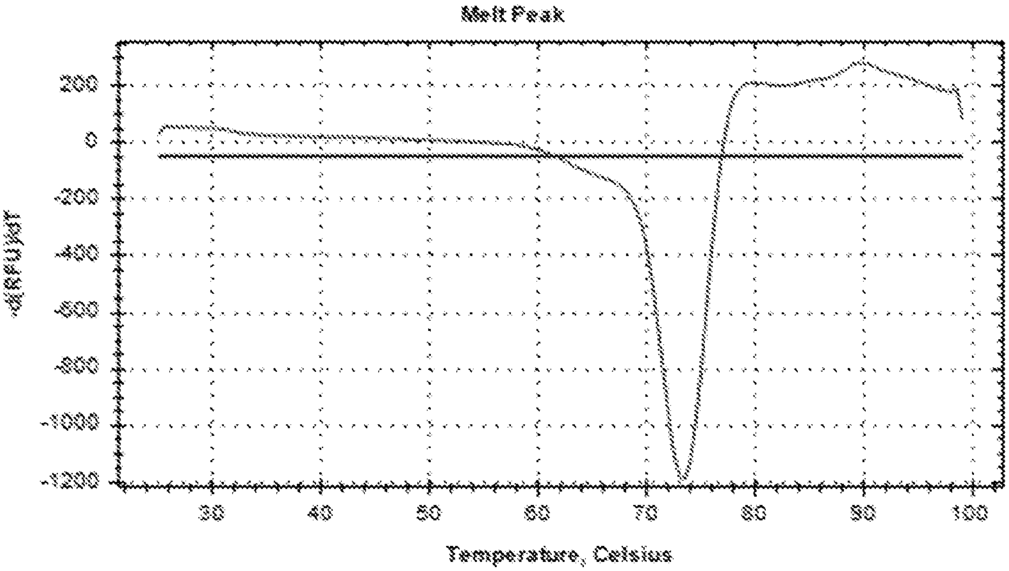
FIG. 17 shows the protein thermal shift assay result of antibody hu1H7-V5.

Further, as shown in FIG. 17, with the melting temperature, the humanized antibody hu1H7-V5 was probably stable in human body.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

Description/Sequence/SEQ ID NO.

VH CDR1 for mouse, chimeric and humanized 1H7

(SEQ ID NO: 1)

NYWMH

VH CDR2 for mouse, chimeric and humanized 1H7

(SEQ ID NO: 4)

EINPTNGRTNYNENFKS

VH CDR3 for mouse, chimeric and humanized 1H7

(SEQ ID NO: 11)

LNTHYVFDS

VL CDR1 formouse, chimeric and humanized 1H7

(SEQ ID NO: 15)

SVSSSISSNYLH

VL CDR2 for mouse, chimeric and humanized 1H7

(SEQ ID NO: 18)

RTSTLAS

VL CDR3 for mouse, chimeric and humanized 1H7

(SEQ ID NO: 22)

QQGSGIPFT

VH for mouse and chimeric 1H7

(SEQ ID NO: 24)

QVQLQQPGTELVKPGASVKLSCKASGYTFTNYWMHWVKQRPGQGLDWIGEINPTNGRTNYN

ENFKSKATLTVDKSSSTAYMQLSSLTSEDSAVYYCARLNTHYVFDSWGQGTTLTLSS

VH for mouse 1H7

(SEQ ID NO: 46)

CAGGTCCAACTGCAGCAGCCTGGGACTGAACTGGTGAAGCCTGGGGCTTCAGTGAAACTGT

CCTGCAAGGCTTCTGGCTACACCTTCACCAACTACTGGATGCACTGGGTGAAACAGAGGCC

TGGACAAGGCCTTGACTGGATTGGAGAGATTAATCCTACCAACGGTCGTACAAACTACAAT

GAGAATTTCAAGAGTAAGGCCACACTGACTGTAGACAAATCCTCCAGCACAGCCTACATGC

AACTCAGTAGCCTGACATCTGAAGACTCTGCGGTCTATTACTGTGCAAGATTGAATACTCA

CTACGTTTTTGACTCCTGGGGCCAAGGCACCACTCTCACACTGTCCTCA

VH for chimeric 1H7

(SEQ ID NO: 47)

CAAGTGCAGCTGCAGCAGCCCGGCACAGAGCTGGTGAAACCCGGCGCCAGCGTGAAGCTG

AGCTGCAAGGCCAGCGGCTATACCTTCACCAACTACTGGATGCACTGGGTGAAGCAGAGA

CCCGGCCAAGGACTGGATTGGATCGGCGAGATCAATCCCACCAACGGAAGAACCAACTAC

AACGAGAACTTCAAGTCCAAGGCCACACTGACCGTGGACAAGAGCAGCAGCACAGCCTAC

ATGCAGCTGAGCTCTCTGACCAGCGAGGACTCCGCCGTGTACTACTGCGCCAGACTGAACA

CCCACTACGTGTTCGACAGCTGGGGCCAAGGCACCACACTGACACTGTCCAGC

VH for hu1H7-V1-2

(SEQ ID NO: 26)

QVQLVQSGAEVKKPGASVKVSCKASGYTFTNYWMHWVKQAPGQGLDWIGEINPTNGRTNYN

ENFKSKATLTVDKSTSTAYMELSSLRSEDTAVYYCARLNTHYVFDSWGQGTLVTVSS

-continued

VH for hu1H7-V1, and hu1H7-V7
(SEQ ID NO: 25, X1 = I, X2 = K, X3 = A)
QVQLVQSGAEVKKPGASVKVSCKASGYTFTNYWMHWVRQAPGQGLEWIGEINPTNGRTNY

NENFKSKVTLTVDX2STSTX3YMELSSLRSEDTAVYYCARLNTHYVFDSWGQGTLVTVSS (SEQ ID NO: 56)
QVQLVQSGAEVKKPGASVKVSCKASGYTFTNYWMHWVRQAPGQGLEWIGEINPTNGRTNYN

ENFKSKVTLTVDKSTSTAYMELSSLRSEDTAVYYCARLNTHYVFDSWGQGTLVTVSS

VH for hu1H7-V2, and hu1H7-V8
(SEQ ID NO: 27, X1 = K, X2 = L, X3 = R)
QVQLVQSGAEVKKPGASVKVSCKASGYTFTNYWMHWVRQAPGQGLEWIGEINPTNGRTNYN

ENFKSX1VTX2TX3DTSTSTVYMELSSLRSEDTAVYYCARLNTHYVFDSWGQGTLVTVSS (SEQ ID NO: 63)
QVQLVQSGAEVKKPGASVKVSCKASGYTFTNYWMHWVRQAPGQGLEWIGEINPTNGRTNYN

ENFKSKVTLTRDTSTSTVYMELSSLRSEDTAVYYCARLNTHYVFDSWGQGTLVTVSS

VH for hu1H7-V3, and hu1H7-V9
(SEQ ID NO: 27, X1 = K, X2 = M, X3 = V)
QVQLVQSGAEVKKPGASVKVSCKASGYTFTNYWMHWVRQAPGQGLEWIGEINPTNGRTNYN

ENFKSX1VTX2TX3DTSTSTVYMELSSLRSEDTAVYYCARLNTHYVFDSWGQGTLVTVSS (SEQ ID NO: 64)
QVQLVQSGAEVKKPGASVKVSCKASGYTFTNYWMHWVRQAPGQGLEWIGEINPTNGRTNYN

ENFKSKVTMTVDTSTSTVYMELSSLRSEDTAVYYCARLNTHYVFDSWGQGTLVTVSS

VH for hu1H7-V4, and hu1H7-V10
(SEQ ID NO: 25, X1 = M, X2 = T, X3 = V)
QVQLVQSGAEVKKPGASVKVSCKASGYTFTNYWMHWVRQAPGQGLEWX1GEINPTNGRTNY

NENFKSKVTLTVDX2STSTX3YMELSSLRSEDTAVYYCARLNTHYVFDSWGQGTLVTVSS (SEQ ID NO: 61)
QVQLVQSGAEVKKPGASVKVSCKASGYTFTNYWMHWVRQAPGQGLEWMGEINPTNGRTNY

NENFKSKVTLTVDTSTSTVYMELSSLRSEDTAVYYCARLNTHYVFDSWGQGTLVTVSS

VH for hu1H7-V5, and hu1H7-V11
(SEQ ID NO: 27, X1 = R, X2 = L, X3 = V)
QVQLVQSGAEVKKPGASVKVSCKASGYTFTNYWMHWVRQAPGQGLEWIGEINPTNGRTNYN

ENFKSX1VTX2TX3DTSTSTVYMELSSLRSEDTAVYYCARLNTHYVFDSWGQGTLVTVSS (SEQ ID NO: 48)
QVQLVQSGAEVKKPGASVKVSCKASGYTFTNYWMHWVRQAPGQGLEWIGEINPTNGRTNYN

ENFKSRVTLTVDTSTSTVYMELSSLRSEDTAVYYCARLNTHYVFDSWGQGTLVTVSS

CAAGTGCAGCTGGTGCAAAGCGGAGCCGAGGTGAAAAAGCCCGGCGCCAGCGTGAAGGTG

AGCTGCAAGGCCAGCGGCTACACCTTCACCAACTACTGGATGCACTGGGTGAGACAAGCC

CCCGGCCAAGGACTGGAGTGGATCGGCGAGATCAACCCTACCAACGGAAGAACCAACTAC

AACGAGAACTTCAAGTCTAGAGTGACACTGACCGTGGACACCTCCACAAGCACCGTGTAC

ATGGAGCTGAGCTCTCTGAGATCCGAGGACACCGCCGTGTACTACTGCGCTAGACTGAACA

CCCACTACGTGTTCGACAGCTGGGGCCAAGGCACACTGGTGACCGTGTCCTCC

VH for hu1H7-V6, and hu1H7-V12
(SEQ ID NO: 25, X1 = I, X2 = T, X3 = V)
QVQLVQSGAEVKKPGASVKVSCKASGYTFTNYWMHWVRQAPGQGLEWX1GEINPTNGRTNY

NENFKSKVTLTVDX2STSTX3YMELSSLRSEDTAVYYCARLNTHYVFDSWGQGTLVTVSS (SEQ ID NO: 62)
QVQLVQSGAEVKKPGASVKVSCKASGYTFTNYWMHWVRQAPGQGLEWIGEINPTNGRTNYN

ENFKSKVTLTVDTSTSTVYMELSSLRSEDTAVYYCARLNTHYVFDSWGQGTLVTVSS

-continued

VL for mouse and chimeric 1H7

(SEQ ID NO: 34)

EIVLTQSPTTLAASPGEKITFTCSVSSSISSNYLHWYQQKPGFSPKLLISRTSTLASGVP

ARFSGSGSGTSYSLTIGTMEAEDVATYYCQQGSGIPFTFGSGTKLELK

VL for mouse 1H7

(SEQ ID NO: 49)

GAAATTGTTCTCACCCAGTCTCCAACCACCTTGGCTGCATCTCCCGGGGAGAAGATCACTTT

CACCTGCAGTGTCAGTTCAAGTATAAGTTCCAATTACTTGCATTGGTATCAGCAGAAGCCA

GGATTCTCCCCTAAACTCTTGATTTCTAGGACATCCACTCTGGCTTCTGGAGTCCCAGCTCG

CTTCAGTGGCAGTGGGTCTGGGACCTCTTACTCTCTCACAATTGGCACCATGGAGGCTGAA

GATGTTGCCACTTACTACTGCCAGCAGGGTAGTGGTATACCATTCACGTTCGGCTCGGGGA

CAAAGTTGGAATTAAAA

VL for chimeric 1H7

(SEQ ID NO: 50)

GAGATCGTGCTGACCCAGAGCCCTACAACACTGGCTGCCAGCCCCGGCGAGAAGATCACC

TTCACATGCAGCGTGAGCAGCAGCATCAGCTCCAATTATCTGCACTGGTATCAGCAGAAGC

CCGGCTTCAGCCCCAAACTGCTGATCTCTAGAACCAGCACACTGGCTTCCGGCGTGCCCGC

CAGATTTTCCGGCAGCGGAAGCGGCACCAGCTACTCTCTGACCATTGGCACCATGGAGGCC

GAGGATGTGGCCACCTACTACTGCCAGCAAGGCTCCGGCATTCCCTTCACCTTCGGCAGCG

GCACCAAGCTGGAGCTGAAG

VL for hu1H7-V1-2

(SEQ ID NO: 36)

EIVLTQSPGTLSLSPGERATLTCSVSSSISSNYLHWYQQKPGFSPRLLISRTSTLASGIPA

RFSGSGSGTSYSLTISRMQSEDFAVYYCQQGSGIPFTFGQGTKLEIK

VL for hu1H7-V1-hu1H7-V6

(SEQ ID NO: 35, X1 = Y, X2 = M)

EIVLTQSPGTLSLSPGERATLSCSVSSSISSNYLHWYQQKPGLSPRLLISRTSTLASGIPA

RFSGSGSGTEX1TLTISRX2QSEDFAVYYCQQGSGIPFTFGQGTKLEIK (SEQ ID NO: 51)

EIVLTQSPGTLSLSPGERATLSCSVSSSISSNYLHWYQQKPGLSPRLLISRTSTLASGIPA

RFSGSGSGTEYTLTISRMQSEDFAVYYCQQGSGIPFTFGQGTKLEIK

GAGATCGTGCTGACCCAGAGCCCCGGCACACTGTCTCTGAGCCCCGGCGAGAGAGCCACA

CTGAGCTGCAGCGTGAGCAGCAGCATCAGCAGCAACTATCTGCACTGGTATCAGCAGAAG

CCCGGACTGAGCCCTAGACTGCTGATCTCTAGAACCTCCACACTGGCCAGCGGCATCCCCG

CCAGATTTAGCGGAAGCGGAAGCGGCACCGAGTACACACTGACCATCTCTAGAATGCAGA

GCGAGGACTTCGCCGTGTACTACTGCCAGCAAGGCAGCGGAATCCCCTTCACCTTCGGCCA

AGGCACCAAGCTGGAGATCAAG

VL for hu1H7-V7-hu1H7-V12

(SEQ ID NO: 35, X1 = F, X2 = L)

EIVLTQSPGTLSLSPGERATLSCSVSSSISSNYLHWYQQKPGLSPRLLISRTSTLASGIPA

RFSGSGSGTEX1TLTISRX2QSEDFAVYYCQQGSGIPFTFGQGTKLEIK (SEQ ID NO: 66)

EIVLTQSPGTLSLSPGERATLSCSVSSSISSNYLHWYQQKPGLSPRLLISRTSTLASGIPA

RFSGSGSGTEFTLTISRLQSEDFAVYYCQQGSGIPFTFGQGTKLEIK

Heavy chain constant region (SEQ ID NO: 41)

ASTKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPAPELLGGPSVFLFPP

-continued

KPKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGNVFSCSVMHEALHN

HYTQKSLSLSPGK (SEQ ID NO: 52)

GCTAGCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTG

GAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACA

TCTGCAACGTGAATCACAAGCCCAGCAACACCAAGGTGGACAAGAAAGTTGAGCCCAAAT

CTTGTGACAAAACTCACACATGCCCACCGTGCCCAGCACCTGAACTCCTGGGGGGACCGTC

AGTCTTCCTCTTCCCCCCAAAACCCAAGGACACCCTCATGATCTCCCGGACCCCTGAGGTC

ACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTAC

AAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGATGACC

AAGAACCAGGTCAGCCTGACCTGCCTGGTCAAAGGCTTCTATCCCAGCGACATCGCCGTGG

AGTGGGAGAGCAATGGGCAGCCGGAGAACAACTACAAGACCACGCCTCCCGTGCTGGACT

CCGACGGCTCCTTCTTCCTCTACAGCAAGCTCACCGTGGACAAGAGCAGGTGGCAGCAGGG

GAACGTCTTCTCATGCTCCGTGATGCATGAGGCTCTGCACAACCACTACACGCAGAAGAGC

CTCTCCCTGTCTCCGGGTAAATGA

Light chain constant region (SEQ ID NO: 42)

RTVAAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC (SEQ ID NO: 53)

CGTACGGTGGCGGCGCCATCTGTCTTCATCTTCCCGCCATCTGATGAGCAGTTGAAATCTGG

AACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGACTACGAGAAA

CACAAAGTCTACGCCTGCGAAGTCACCCATCAGGGCCTGAGCTCGCCCGTCACAAAGAGCT

TCAACAGGGGAGAGTGTTGA

VH CDR1 for mouse 1F7

(SEQ ID NO: 2)

SYWMH

VH CDR2 for mouse 1F7

(SEQ ID NO: 5)

EINPSNGRTNYNEKFKN

VH CDR3 for mouse 1F7

(SEQ ID NO: 12)

LSIHYVFDY

VL CDR1 for mouse 1F7

(SEQ ID NO: 16)

SASSSISSNYLH

VL CDR2 for mouse 1F7

(SEQ ID NO: 19)

GTSNLAS

-continued

VL CDR3 for mouse 1F7
(SEQ ID NO: 22)
QQGSGIPFT

VH for mouse 1F7
(SEQ ID NO: 28)
QVQLQQPGAELVKPGASVKLSCKASDYTFTSYWMHWVKQRPGQGLEWIGEINPSNGRTNYNE

KFKNKATLTVDKSSSTAYVQLYSLTSEDSAVYYCARLSIHYVFDYWGQGTTLTVSS

VL for mouse 1F7
(SEQ ID NO: 37)
ELVLTQSPTTMAASPGEKITFTCSASSSISSNYLHWYQQKPGFSPKLLISGTSNLASGVPPRF

SGSGSGTSYSLTIVTMEAEDVATYYCQQGSGIPFTFGSGTKLEIK

VH CDR1 for mouse and chimeric 1B5
(SEQ ID NO: 2)
SYWMH

VH CDR2 for mouse and chimeric 1B5
(SEQ ID NO: 6)
EINPSNGRTNYNENFKS

VH CDR3 for mouse and chimeric 1B5
(SEQ ID NO: 13)
LNTHYVFDY

VL CDR1 for mouse and chimeric 1B5
(SEQ ID NO: 15)
SVSSSISSNYLH

VL CDR2 for mouse and chimeric 1B5
(SEQ ID NO: 20)
RTSNLAS

VL CDR3 for mouse and chimeric 1B5
(SEQ ID NO: 22)
QQGSGIPFT

VH for mouse and chimeric 1B5
(SEQ ID NO: 29)
QVQLQQPGAELVKPGASVKLSCKASGYTFTSYWMHWVKQRPGQGLEWIGEINPSNGRTNYNE

NFKSKATLTVDKSSSTAYMQLSSLTSEDSAVYYCARLNTHYVFDYWGQGTTLTVSS

VL for mouse and chimeric 1B5
(SEQ ID NO: 38)
EIVLTQSPTILAASPGEKITFTCSVSSSISSNYLHWYQQKPGFSPKLLIYRTSNLASGVPA

RFSGSGSGTSYSLTIGTMEAEDVATYYCQQGSGIPFTFGSGTKLEIK

VH CDR1 for mouse 3C2
(SEQ ID NO: 3)
TYWIH

VH CDR2 for mouse 3C2
(SEQ ID NO: 7)
EINPSNGRTNYNEHFKS

VH CDR3 formouse 3C2
(SEQ ID NO: 11)
LNTHYVFDS

VL CDR1 for mouse 3C2
(SEQ ID NO: 16)
SASSSISSNYLH

VL CDR2 for mouse 3C2
(SEQ ID NO: 20)
RTSNLAS

VL CDR3 for mouse 3C2
(SEQ ID NO: 22)
QQGSGIPFT

-continued

VH for mouse 3C2

(SEQ ID NO: 30)

QVQLQQPGTELVKPGASVKLSCKASGYTFTTYWIHWVKQRPGQGLEWIGEINPSNGRTNYNEH

FKSKATLTVDKSSSTASMQLSSLTSADSAVYYCARLNTHYVFDSWGQGTTLTVSS

VL for mouse 3C2

(SEQ ID NO: 39, X1 = Y, X2 = H, X3 = E)

EIVLTQSPTTMAASPGEKITITCSASSSISSNYLHWYQQKPGFSPKLLIX1RTSNLASGVPT

X2FSGSGSGTSYSLTIGTMEAX3DVATYYCQQGSGIPFTFGSGTKLEIK (SEQ ID NO: 67)

EIVLTQSPTTMAASPGEKITITCSASSSISSNYLHWYQQKPGFSPKLLIYRTSNLASGVPT

HFSGSGSGTSYSLTIGTMEAEDVATYYCQQGSGIPFTFGSGTKLEIK

VH CDR1 for mouse 1A3

(SEQ ID NO: 2)

SYWMH

VH CDR2 for mouse 1A3

(SEQ ID NO: 8)

EINPSNGRTNFNEKFKT

VH CDR3 for mouse 1A3

(SEQ ID NO: 13)

LNTHYVFDY

VL CDR1 for mouse 1A3

(SEQ ID NO: 16)

SASSSISSNYLH

VL CDR2 for mouse 1A3

(SEQ ID NO: 20)

RTSNLAS

VL CDR3 for mouse 1A3

(SEQ ID NO: 22)

QQGSGIPFT

VH for mouse 1A3

(SEQ ID NO: 31)

QVQLQQPGAELVKPGASVKLSCKASGYTFTSYWMHWVKQRPAQGLEWIGEINPSNGRTNFNE

KFKTKATLTVDKSSNTAYMQLSSLTSEDSAVYSCLRLNTHYVFDYWGQGTTLTVSS

VL for mouse 1A3

(SEQ ID NO: 39, X1 = S, X2 = R, X3 = G)

EIVLTQSPTTMAASPGEKITITCSASSSISSNYLHWYQQKPGFSPKLLIX1RTSNLASGVP

STX2FSGGSGTSYSLTIGTMEAX3DVATYYCQQGSGIPFTFGSGTKLEIK (SEQ ID NO: 60)

EIVLTQSPTTMAASPGEKITITCSASSSISSNYLHWYQQKPGFSPKLLISRTSNLASGVPT

RFSGSGSGTSYSLTIGTMEAGDVATYYCQQGSGIPFTFGSGTKLEIK

VH CDR1 formouse 1D4

(SEQ ID NO: 2)

SYWMH

VH CDR2 for mouse 1D4

(SEQ ID NO: 9)

EINPTNGRTNYNEDFKS

VH CDR3 for mouse 1D4

(SEQ ID NO: 13)

LNTHYVFDY

VL CDR1 for mouse 1D4

(SEQ ID NO: 15)

SVSSSISSNYLH

VL CDR2 for mouse 1D4

(SEQ ID NO: 20)

RTSNLAS

-continued

VL CDR3 for mouse 1D4
(SEQ ID NO: 22)
QQGSGIPFT

VH for mouse 1D4
(SEQ ID NO: 32, X1 = N, X2 = L)
QVQLQQPGAELVKPGASVKLSCKASGYTFTSYWMHWVKVRPGQGLEWIGEINPTNGRTNYNE

DFKSKATLTVX1SSSSTAYMQX2SSLTSEDSAVYYCARLNTHYVFDYWGQGTTLTVSS (SEQ ID NO: 58)
QVQLQQPGAELVKPGASVKLSCKASGYTFTSYWMHWVKVRPGQGLEWIGEINPTNGRTNYNE

DFKSKATLTVNSSSSTAYMQLSSLTSEDSAVYYCARLNTHYVFDYWGQGTTLTVSS

VL for mouse 1D4
(SEQ ID NO: 38)
EIVLTQSPTILAASPGEKITFTCSVSSSISSNYLHWYQQKPGFSPKLLIYRTSNLASGVPAR

FSGSGSGTSYSLTIGTMEAEDVATYYCQQGSGIPFTFGSGTKLEIK

VH CDR1 formouse 1G1
(SEQ ID NO: 2)
SYWMH

VH CDR2 for mouse 1G1
(SEQ ID NO: 9)
EINPTNGRTNYNEDFKS

VH CDR3 for mouse 1G1
(SEQ ID NO: 13)
LNTHYVFDY

VL CDR1 formouse 1G1
(SEQ ID NO: 15)
SVSSSISSNYLH

VL CDR2 for mouse 1G1
(SEQ ID NO: 20)
RTSNLAS

VL CDR3 formouse 1G1
(SEQ ID NO: 22)
QQGSGIPFT

VH for mouse 1G1
(SEQ ID NO: 32, X1 = E, X2 = F)
QVQLQQPGAELVKPGASVKLSCKASGYTFTSYWMHWVKVRPGQGLEWIGEINPTNGRTNYNE

DFKSKATLTVX1SSSSTAYMQX2SSLTSEDSAVYYCARLNTHYVFDYWGQGTTLTVSS (SEQ ID NO: 65)
QVQLQQPGAELVKPGASVKLSCKASGYTFTSYWMHWVKVRPGQGLEWIGEINPTNGRTNYNE

DFKSKATLTVESSSSTAYMQFSSLTSEDSAVYYCARLNTHYVFDYWGQGTTLTVSS

VL for mouse 1G1
(SEQ ID NO: 38)
EIVLTQSPTILAASPGEKITFTCSVSSSISSNYLHWYQQKPGFSPKLLIYRTSNLASGVPAR

FSGSGSGTSYSLTIGTMEAEDVATYYCQQGSGIPFTFGSGTKLEIK

VH CDR1 for mouse and chimeric 1H9
(SEQ ID NO: 2)
SYWMH

VH CDR2 for mouse and chimeric 1H9
(SEQ ID NO: 10)
EINPTNGRTNYYEKFKN

VH CDR3 for mouse and chimeric 1H9
(SEQ ID NO: 14)
FHYSRWYFDV

VL CDR1 for mouse and chimeric 1H9
(SEQ ID NO: 17)
KASQNVGTAVV

-continued

VL CDR2 for mouse and chimeric 1H9

(SEQ ID NO: 21)

PASNRYT

VL CDR3 for mouse and chimeric 1H9

(SEQ ID NO: 23)

QQYSSYPLT

VH for mouse and chimeric 1H9

(SEQ ID NO: 33)

QVQLQQPGAELVKPGASVKLSCKASGYTFTSYWMHWVKLRPGQGLEWIGEINPTNGRTNYYE

KFKNRATLTADKSSSTAYMQLSSLTFEDSAVYFCAKFHYSRWYFDVWGTGTTVTVSS

VL for mouse and chimeric 1H9

(SEQ ID NO: 40)

DIVMTQSQKFMSTSVGDRVSITCKASQNVGTAVVWYQQKPGQSPKLLINPASNRYTGVPDRFT

GSGSGTDFTLTISNMQSEDLADYFCQQYSSYPLTFGAGTKLELK

Human IL6R Fc protein (SEQ ID NO: 43)

LAPRRCPAQEVARGVLTSLPGDSVTLTCPGVEPEDNATVHWVLRKPAAGSHPSRWAGMGRRL

LLRSVQLHDSGNYSCYRAGRPAGTVHLLVDVPPEEPQLSCFRKSPLSNVVCEWGPRSTPSLTTK

AVLLVRKFQNSPAEDFQEPCQYSQESQKFSCQLAVPEGDSSFYIVSMCVASSVGSKFSKTQTFQ

GCGILQPDPPANITVTAVARNPRWLSVTWQDPHSWNSSFYRLRFELRYRAERSKTFTTWMVKD

LQHHCVIHDAWSGLRHVVQLRAQEEFGQGEWSEWSPEAMGTPWTESRSPPAENEVSTPMQALTT

NKDDDNILFRDSANATSLPVQDSSSVPLPEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALHNHYTQ

KSLSLSPGK

Human IL6R-his protein (SEQ ID NO: 44)

LAPRRCPAQEVARGVLTSLPGDSVTLTCPGVEPEDNATVHWVLRKPAAGSHPSRWAGMGRRL

LLRSVQLHDSGNYSCYRAGRPAGTVHLLVDVPPEEPQLSCFRKSPLSNVVCEWGPRSTPSLTTK

AVLLVRKFQNSPAEDFQEPCQYSQESQKFSCQLAVPEGDSSFYIVSMCVASSVGSKFSKTQTFQ

GCGILQPDPPANITVTAVARNPRWLSVTWQDPHSWNSSFYRLRFELRYRAERSKTFTTWMVKD

LQHHCVIHDAWSGLRHVVQLRAQEEFGQGEWSEWSPEAMGTPWTESRSPPAENEVSTPMQAL

TTNKDDDNILFRDSANATSLPVQDSSSVPLPHHHHHHHHHH

Macaca IL6R-his protein (SEQ ID NO: 45)

MNSVSTSAFGPVAFSLGLLLVLPAAFPAPVLPGEDSKDVAAPHSQPLTSSERIDKHIRYILDGISA

LRKETCNRSNMCESSKEALAENNLNLPKMAEKDGCFQSGFNEDTCLVKIITGLLEFEVYLEYLQ

NRFESSEEQARAVQMSTKVLIQFLQKKAKNLDAITTPEPTTNASLLTKLQAQNQWLQDMTTHL

ILRSFKEFLQSSLRALRQMHHHHHHHHHH

Heavy chain of Tocilizumab (SEQ ID NO: 54)

QVQLQESGPGLVRPSQTLSLTCTVSGYSITSDHAWSWVRQPPGRGLEWIGYISYSGITTYNPSLK

SRVTMLRDTSKNQFSLRLSSVTAADTAVYYCARSLARTTAMDYWGQGSLVTVSSASTKGPSV

FPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNG

-continued

KEYKCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLS

LSPG

Light chain of Tocilizumab (SEQ ID NO: 55)

DIQMTQSPSSLSASVGDRVTITCRASQDISSYLNWYQQKPGKAPKLLIYYTSRLHSGVPSRFSGS

GSGTDFTFTISSLQPEDIATYYCQQGNTLPYTFGQGTKVEIKRTVAAPSVFIFPPSDEQLKSGTAS

VVCLLNNFYPREAKVQWKVDNALQSGNSQESVTEQDSKDSTYSLSSTLTLSKADYEKHKVYA

CEVTHQGLSSPVTKSFNRGEC

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated monoclonal antibody or an antigen-binding portion thereof, specifically binding to interleukin 6 receptor subunit alpha (IL6R), comprising i) a heavy chain variable region comprising a VH CDR1 region, a VH CDR2 region and a VH CDR3 region, and ii) a light chain variable region comprising a VL CDR1 region, a VL CDR2 region and a VL CDR3 region, wherein the VH CDR1 region, the VH CDR2 region, the VH CDR3 region, the VL CDR1 region, the VL CDR2 region and the VL CDR3 region comprise the amino acid sequences of (1) SEQ ID NOs: 1, 4, 11, 15, 18, and 22, respectively; (2) SEQ ID NOs: 2, 5, 12, 16, 19, and 22, respectively; (3) SEQ ID NOs: 2, 6, 13, 15, 20, and 22, respectively; (4) SEQ ID NOs: 3, 7, 11, 16, 20, and 22, respectively; (5) SEQ ID NOs: 2, 8, 13, 16, 20, and 22, respectively; (6) SEQ ID NOs: 2, 9, 13, 15, 20, and 22, respectively; or (7) SEQ ID NOs: 2, 10, 14, 17, 21, and 23, respectively.

2. The isolated monoclonal antibody or the antigen-binding portion thereof, of claim 1, wherein the heavy chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 24, 56, 61, 62, 26, 57, 63, 64, 28, 29, 30, 31, 58, 65 or 33.

3. The isolated monoclonal antibody or the antigen-binding portion thereof, of claim 1, wherein the light chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 34, 59, 66, 36, 37, 38, 60, 67 or 40.

4. The isolated monoclonal antibody or the antigen-binding portion thereof, of claim 2, wherein the heavy chain variable region and the light chain variable region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 24 and 34, respectively;
(2) SEQ ID NOs: 56 and 59, respectively;
(3) SEQ ID NOs: 26 and 36, respectively;
(4) SEQ ID NOs: 63 and 59, respectively;
(5) SEQ ID NOs: 64 and 59, respectively;
(6) SEQ ID NOs: 61 and 59, respectively;
(7) SEQ ID NOs: 57 and 59, respectively;
(8) SEQ ID NOs: 62 and 59, respectively;
(9) SEQ ID NOs: 56 and 66, respectively;
(10) SEQ ID NOs: 63 and 66, respectively;
(11) SEQ ID NOs: 64 and 66, respectively;
(12) SEQ ID NOs: 61 and 66, respectively;
(13) SEQ ID NOs: 57 and 66, respectively;
(14) SEQ ID NOs: 62 and 66 respectively;
(15) SEQ ID NOs: 28 and 37, respectively;
(16) SEQ ID NOs: 29 and 38, respectively;
(17) SEQ ID NOs: 30 and 67, respectively;
(18) SEQ ID NOs: 31 and 60, respectively;
(19) SEQ ID NOs: 58 and 38, respectively;
(20) SEQ ID NOs: 65 and 38, respectively; or
(21) SEQ ID NOs: 33 and 40, respectively.

5. The isolated monoclonal antibody or the antigen-binding portion thereof of claim 1, which is an IgG1, IgG2 or IgG4 isotype.

6. The isolated monoclonal antibody or the antigen-binding portion thereof, of claim 4, comprising a heavy chain constant region comprising the amino acid sequence of SEQ ID NO: 41, linked to the heavy chain variable region, and a light chain constant region comprising the amino acid sequence of SEQ ID NO: 42, linked to the light chain variable region.

7. The isolated monoclonal antibody or the antigen-binding portion thereof, of claim 1, which is able to (a) bind human IL6R; (b) bind monkey IL6R; (c) block IL6-IL6R binding; and/or (d) inhibit IL6-IL6R induced cell signaling.

8. The isolated monoclonal antibody or the antigen-binding portion thereof, of claim 1, which is mouse, chimeric or humanized.

9. A nucleic acid molecule encoding the isolated monoclonal antibody or the antigen-binding portion thereof, of claim 1.

10. An expression vector comprising the nucleic acid molecule of claim 9.

11. A host cell comprising the expression vector of claim 10.

12. A pharmaceutical composition comprising the isolated monoclonal antibody or antigen-binding portion thereof, of claim 1, and a pharmaceutically acceptable carrier.

13. The pharmaceutical composition of claim 12, further comprising an anti-inflammatory agent or an anti-tumor agent.

14. A method for treating a disease associated with excessive IL6/IL6R signaling in a subject in need thereof, comprising administering to the subject a therapeutically effective amount of the pharmaceutical composition of claim 12.

15. The method of claim 14, wherein the disease is an inflammatory disease.

16. The method of claim 15, wherein the inflammatory disease is rheumatoid arthritis, systemic and polyarticular juvenile idiopathic arthritis, giant cell arteritis, Takayasu arteritis, Castleman's disease, cytokine release syndrome, Schnitzler syndrome, or neuromyelitis optica.

17. The method of claim 14, wherein the disease is cancer.

18. The method of claim 17, wherein the cancer is non-small cell lung cancer, or diffuse large B-cell lymphoma.

* * * * *

SEQUENCE LISTING

```
<160> NUMBER OF SEQ ID NOS: 67

<210> SEQ ID NO 1
<211> LENGTH: 5
<212> TYPE: PRT
<213> ORGANISM: Artificial Sequence
<220> FEATURE:
<223> OTHER INFORMATION: VH CDR1 for mouse, chimeric and humanized 1H7

<400> SEQUENCE: 1

Asn Tyr Trp Met His
1               5


<210> SEQ ID NO 2
<211> LENGTH: 5
<212> TYPE: PRT
<213> ORGANISM: Artificial Sequence
<220> FEATURE:
<223> OTHER INFORMATION: VH CDR1 for mouse 1F7, mouse and chimeric 1B5,
      mouse 1A3, mouse 1D4, mouse 1G1, mouse and chimeric 1H9

<400> SEQUENCE: 2

Ser Tyr Trp Met His
1               5


<210> SEQ ID NO 3
<211> LENGTH: 5
<212> TYPE: PRT
<213> ORGANISM: Artificial Sequence
<220> FEATURE:
<223> OTHER INFORMATION: VH CDR1 for mouse 3C2

<400> SEQUENCE: 3

Thr Tyr Trp Ile His
1               5


<210> SEQ ID NO 4
<211> LENGTH: 17
<212> TYPE: PRT
<213> ORGANISM: Artificial Sequence
<220> FEATURE:
<223> OTHER INFORMATION: VH CDR2 for mouse, chimeric and humanized 1H7

<400> SEQUENCE: 4

Glu Ile Asn Pro Thr Asn Gly Arg Thr Asn Tyr Asn Glu Asn Phe Lys
1               5                   10                  15
```

Ser

<210> SEQ ID NO 5
<211> LENGTH: 17
<212> TYPE: PRT
<213> ORGANISM: Artificial Sequence
<220> FEATURE:
<223> OTHER INFORMATION: VH CDR2 for mouse 1F7

<400> SEQUENCE: 5

Glu Ile Asn Pro Ser Asn Gly Arg Thr Asn Tyr Asn Glu Lys Phe Lys
1 5 10 15

Asn

<210> SEQ ID NO 6
<211> LENGTH: 17
<212> TYPE: PRT
<213> ORGANISM: Artificial Sequence
<220> FEATURE:
<223> OTHER INFORMATION: VH CDR2 for mouse and chimeric 1B5

<400> SEQUENCE: 6

Glu Ile Asn Pro Ser Asn Gly Arg Thr Asn Tyr Asn Glu Asn Phe Lys
1 5 10 15

Ser

<210> SEQ ID NO 7
<211> LENGTH: 17
<212> TYPE: PRT
<213> ORGANISM: Artificial Sequence
<220> FEATURE:
<223> OTHER INFORMATION: VH CDR2 for mouse 3C2

<400> SEQUENCE: 7

Glu Ile Asn Pro Ser Asn Gly Arg Thr Asn Tyr Asn Glu His Phe Lys
1 5 10 15

Ser

<210> SEQ ID NO 8
<211> LENGTH: 17
<212> TYPE: PRT
<213> ORGANISM: Artificial Sequence
<220> FEATURE:
<223> OTHER INFORMATION: VH CDR2 for mouse 1A3

<400> SEQUENCE: 8

Glu Ile Asn Pro Ser Asn Gly Arg Thr Asn Phe Asn Glu Lys Phe Lys
1 5 10 15

Thr

<210> SEQ ID NO 9
<211> LENGTH: 17
<212> TYPE: PRT
<213> ORGANISM: Artificial Sequence
<220> FEATURE:
<223> OTHER INFORMATION: VH CDR2 for mouse 1D4 and mouse 1G1

<400> SEQUENCE: 9

Glu Ile Asn Pro Thr Asn Gly Arg Thr Asn Tyr Asn Glu Asp Phe Lys
1 5 10 15

Ser

<210> SEQ ID NO 10

<211> LENGTH: 17
<212> TYPE: PRT
<213> ORGANISM: Artificial Sequence
<220> FEATURE:
<223> OTHER INFORMATION: VH CDR2 for mouse and chimeric 1H9

<400> SEQUENCE: 10

Glu Ile Asn Pro Thr Asn Gly Arg Thr Asn Tyr Tyr Glu Lys Phe Lys
1               5                   10                  15

Asn

<210> SEQ ID NO 11
<211> LENGTH: 9
<212> TYPE: PRT
<213> ORGANISM: Artificial Sequence
<220> FEATURE:
<223> OTHER INFORMATION: VH CDR3 for mouse, chimeric and humanized 1H7, and mouse 3C2

<400> SEQUENCE: 11

Leu Asn Thr His Tyr Val Phe Asp Ser
1               5

<210> SEQ ID NO 12
<211> LENGTH: 9
<212> TYPE: PRT
<213> ORGANISM: Artificial Sequence
<220> FEATURE:
<223> OTHER INFORMATION: VH CDR3 for mouse 1F7

<400> SEQUENCE: 12

Leu Ser Ile His Tyr Val Phe Asp Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: VH CDR3 for mouse and chimeric 1B5, mouse 1A3, mouse 1D4, and mouse 1G1

<400> SEQUENCE: 13

Leu Asn Thr His Tyr Val Phe Asp Tyr
1               5

<210> SEQ ID NO 14
<211> LENGTH: 10
<212> TYPE: PRT
<213> ORGANISM: Artificial Sequence
<220> FEATURE:
<223> OTHER INFORMATION: VH CDR3 for mouse and chimeric 1H9

<400> SEQUENCE: 14

Phe His Tyr Ser Arg Trp Tyr Phe Asp Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: VL CDR1 for mouse, chimeric and humanized 1H7, mouse and chimeric 1B5, mouse 1D4, and mouse 1G1

<400> SEQUENCE: 15

Ser Val Ser Ser Ser Ile Ser Ser Asn Tyr Leu His 1 5 10

<210> SEQ ID NO 16
<211> LENGTH: 12
<212> TYPE: PRT
<213> ORGANISM: Artificial Sequence
<220> FEATURE:
<223> OTHER INFORMATION: VL CDR1 for mouse 1F7, mouse 3C2, and mouse 1A3

<400> SEQUENCE: 16

Ser Ala Ser Ser Ser Ile Ser Ser Asn Tyr Leu His
1 5 10

<210> SEQ ID NO 17
<211> LENGTH: 11
<212> TYPE: PRT
<213> ORGANISM: Artificial Sequence
<220> FEATURE:
<223> OTHER INFORMATION: VL CDR1 for mouse and chimeric 1H9

<400> SEQUENCE: 17

Lys Ala Ser Gln Asn Val Gly Thr Ala Val Val
1 5 10

<210> SEQ ID NO 18
<211> LENGTH: 7
<212> TYPE: PRT
<213> ORGANISM: Artificial Sequence
<220> FEATURE:
<223> OTHER INFORMATION: VL CDR2 for mouse, chimeric and humanized 1H7

<400> SEQUENCE: 18

Arg Thr Ser Thr Leu Ala Ser
1 5

<210> SEQ ID NO 19
<211> LENGTH: 7
<212> TYPE: PRT
<213> ORGANISM: Artificial Sequence
<220> FEATURE:
<223> OTHER INFORMATION: VL CDR2 for mouse 1F7

<400> SEQUENCE: 19

Gly Thr Ser Asn Leu Ala Ser
1 5

<210> SEQ ID NO 20
<211> LENGTH: 7
<212> TYPE: PRT
<213> ORGANISM: Artificial Sequence
<220> FEATURE:
<223> OTHER INFORMATION: VL CDR2 for mouse and chimeric 1B5, mouse 3C2, mouse 1A3, mouse 1D4, and mouse 1G1

<400> SEQUENCE: 20

Arg Thr Ser Asn Leu Ala Ser
1 5

<210> SEQ ID NO 21
<211> LENGTH: 7
<212> TYPE: PRT
<213> ORGANISM: Artificial Sequence
<220> FEATURE:
<223> OTHER INFORMATION: VL CDR2 for mouse and chimeric 1H9

<400> SEQUENCE: 21

Pro Ala Ser Asn Arg Tyr Thr 1 5

<210> SEQ ID NO 22
<211> LENGTH: 9
<212> TYPE: PRT
<213> ORGANISM: Artificial Sequence
<220> FEATURE:
<223> OTHER INFORMATION: VL CDR3 for mouse, chimeric and humanized 1H7, mouse and chimeric 1F7, mouse and chimeric 1B5, mouse 3C2, mouse 1A3, mouse 1D4, and mouse 1G1

<400> SEQUENCE: 22

Gln Gln Gly Ser Gly Ile Pro Phe Thr
1 5

<210> SEQ ID NO 23
<211> LENGTH: 9
<212> TYPE: PRT
<213> ORGANISM: Artificial Sequence
<220> FEATURE:
<223> OTHER INFORMATION: VL CDR3 for mouse and chimeric 1H9

<400> SEQUENCE: 23

Gln Gln Tyr Ser Ser Tyr Pro Leu Thr
1 5

<210> SEQ ID NO 24
<211> LENGTH: 118
<212> TYPE: PRT
<213> ORGANISM: Artificial Sequence
<220> FEATURE:
<223> OTHER INFORMATION: VH for mouse and chimeric 1H7

<400> SEQUENCE: 24

Gln Val Gln Leu Gln Gln Pro Gly Thr Glu Leu Val Lys Pro Gly Ala
1 5 10 15

Ser Val Lys Leu Ser Cys Lys Ala Ser Gly Tyr Thr Phe Thr Asn Tyr
20 25 30

Trp Met His Trp Val Lys Gln Arg Pro Gly Gln Gly Leu Asp Trp Ile
35 40 45

Gly Glu Ile Asn Pro Thr Asn Gly Arg Thr Asn Tyr Asn Glu Asn Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Leu Asn Thr His Tyr Val Phe Asp Ser Trp Gly Gln Gly Thr
100 105 110

Thr Leu Thr Leu Ser Ser
115

<210> SEQ ID NO 25
<211> LENGTH: 118
<212> TYPE: PRT
<213> ORGANISM: Artificial Sequence
<220> FEATURE:
<223> OTHER INFORMATION: VH for hu1H7-V1, hu1H7-V4, hu1H7-V6, hu1H7-V7, hu1H7-V10 and hu1H7-V12
<220> FEATURE:
<221> NAME/KEY: misc_feature
<222> LOCATION: (48)..(48)
<223> OTHER INFORMATION: Xaa can be Ile or Met
<220> FEATURE:
<221> NAME/KEY: misc_feature
<222> LOCATION: (74)..(74)

<223> OTHER INFORMATION: Xaa can be Lys or Thr
<220> FEATURE:
<221> NAME/KEY: misc_feature
<222> LOCATION: (79)..(79)
<223> OTHER INFORMATION: Xaa can be Ala or Val

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Xaa
        35                  40                  45

Gly Glu Ile Asn Pro Thr Asn Gly Arg Thr Asn Tyr Asn Glu Asn Phe
    50                  55                  60

Lys Ser Lys Val Thr Leu Thr Val Asp Xaa Ser Thr Ser Thr Xaa Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115
```

<210> SEQ ID NO 26
<211> LENGTH: 118
<212> TYPE: PRT
<213> ORGANISM: Artificial Sequence
<220> FEATURE:
<223> OTHER INFORMATION: VH for hu1H7-V1-2

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Lys Gln Ala Pro Gly Gln Gly Leu Asp Trp Ile
        35                  40                  45

Gly Glu Ile Asn Pro Thr Asn Gly Arg Thr Asn Tyr Asn Glu Asn Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115
```

<210> SEQ ID NO 27
<211> LENGTH: 118
<212> TYPE: PRT
<213> ORGANISM: Artificial Sequence
<220> FEATURE:
<223> OTHER INFORMATION: VH for hu1H7-V2, hu1H7-V3, hu1H7-V5, hu1H7-V8,
hu1H7-V9, and hu1H7-V11
<220> FEATURE:
<221> NAME/KEY: misc_feature
<222> LOCATION: (67)..(67)
<223> OTHER INFORMATION: Xaa can be Lys or Arg
<220> FEATURE:

<221> NAME/KEY: misc_feature
<222> LOCATION: (70)..(70)
<223> OTHER INFORMATION: Xaa can be Leu or Met
<220> FEATURE:
<221> NAME/KEY: misc_feature
<222> LOCATION: (72)..(72)
<223> OTHER INFORMATION: Xaa can be Arg or Val

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Xaa Val Thr Xaa Thr Xaa Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115
```

<210> SEQ ID NO 28
<211> LENGTH: 118
<212> TYPE: PRT
<213> ORGANISM: Artificial Sequence
<220> FEATURE:
<223> OTHER INFORMATION: VH for mouse 1F7

<400> SEQUENCE: 28

```
Gln Val Gln Leu Gln Gln Pro Gly Ala Glu Leu Val Lys Pro Gly Ala
1               5                   10                  15

Ser Val Lys Leu Ser Cys Lys Ala Ser Asp Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Val Gln Leu Tyr Ser Leu Thr Ser Glu Asp Ser Ala Val Tyr Tyr Cys
                85                  90                  95

Ala Arg Leu Ser Ile His Tyr Val Phe Asp Tyr Trp Gly Gln Gly Thr
            100                 105                 110

Thr Leu Thr Val Ser Ser
        115
```

<210> SEQ ID NO 29
<211> LENGTH: 118
<212> TYPE: PRT
<213> ORGANISM: Artificial Sequence
<220> FEATURE:
<223> OTHER INFORMATION: VH for mouse and chimeric 1B5

<400> SEQUENCE: 29

```
Gln Val Gln Leu Gln Gln Pro Gly Ala Glu Leu Val Lys Pro Gly Ala
```

```
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Asn Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Asn Thr His Tyr Val Phe Asp Tyr Trp Gly Gln Gly Thr
            100                 105                 110

Thr Leu Thr Val Ser Ser
        115


<210> SEQ ID NO 30
<211> LENGTH: 118
<212> TYPE: PRT
<213> ORGANISM: Artificial Sequence
<220> FEATURE:
<223> OTHER INFORMATION: VH for mouse 3C2

<400> SEQUENCE: 30

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Ile His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu His Phe
    50                  55                  60

Lys Ser Lys Ala Thr Leu Thr Val Asp Lys Ser Ser Ser Thr Ala Ser
65                  70                  75                  80

Met Gln Leu Ser Ser Leu Thr Ser Ala Asp Ser Ala Val Tyr Tyr Cys
                85                  90                  95

Ala Arg Leu Asn Thr His Tyr Val Phe Asp Ser Trp Gly Gln Gly Thr
            100                 105                 110

Thr Leu Thr Val Ser Ser
        115


<210> SEQ ID NO 31
<211> LENGTH: 118
<212> TYPE: PRT
<213> ORGANISM: Artificial Sequence
<220> FEATURE:
<223> OTHER INFORMATION: VH for mouse 1A3

<400> SEQUENCE: 31

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Ala Gln Gly Leu Glu Trp Ile
        35                  40                  45

Gly Glu Ile Asn Pro Ser Asn Gly Arg Thr Asn Phe Asn Glu Lys Phe
    50                  55                  60
```

```
Lys Thr Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Ser Cys
                85                  90                  95

Leu Arg Leu Asn Thr His Tyr Val Phe Asp Tyr Trp Gly Gln Gly Thr
            100                 105                 110

Thr Leu Thr Val Ser Ser
        115


<210> SEQ ID NO 32
<211> LENGTH: 118
<212> TYPE: PRT
<213> ORGANISM: Artificial Sequence
<220> FEATURE:
<223> OTHER INFORMATION: VH for mouse 1D4 and 1G1
<220> FEATURE:
<221> NAME/KEY: misc_feature
<222> LOCATION: (73)..(73)
<223> OTHER INFORMATION: Xaa can be Asn or Glu
<220> FEATURE:
<221> NAME/KEY: misc_feature
<222> LOCATION: (83)..(83)
<223> OTHER INFORMATION: Xaa can be Leu or Phe

<400> SEQUENCE: 32

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Val Arg Pro Gly Gln Gly Leu Glu Trp Ile
        35                  40                  45

Gly Glu Ile Asn Pro Thr Asn Gly Arg Thr Asn Tyr Asn Glu Asp Phe
    50                  55                  60

Lys Ser Lys Ala Thr Leu Thr Val Xaa Ser Ser Ser Ser Thr Ala Tyr
65                  70                  75                  80

Met Gln Xaa Ser Ser Leu Thr Ser Glu Asp Ser Ala Val Tyr Tyr Cys
                85                  90                  95

Ala Arg Leu Asn Thr His Tyr Val Phe Asp Tyr Trp Gly Gln Gly Thr
            100                 105                 110

Thr Leu Thr Val Ser Ser
        115


<210> SEQ ID NO 33
<211> LENGTH: 119
<212> TYPE: PRT
<213> ORGANISM: Artificial Sequence
<220> FEATURE:
<223> OTHER INFORMATION: VH for mouse and chimeric 1H9

<400> SEQUENCE: 33

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Leu Arg Pro Gly Gln Gly Leu Glu Trp Ile
        35                  40                  45

Gly Glu Ile Asn Pro Thr Asn Gly Arg Thr Asn Tyr Tyr Glu Lys Phe
    50                  55                  60

Lys Asn Arg Ala Thr Leu Thr Ala Asp Lys Ser Ser Ser Thr Ala Tyr
65                  70                  75                  80
```

```
Met Gln Leu Ser Ser Leu Thr Phe Glu Asp Ser Ala Val Tyr Phe Cys
                85                  90                  95

Ala Lys Phe His Tyr Ser Arg Trp Tyr Phe Asp Val Trp Gly Thr Gly
            100                 105                 110

Thr Thr Val Thr Val Ser Ser
        115
```

<210> SEQ ID NO 34
<211> LENGTH: 108
<212> TYPE: PRT
<213> ORGANISM: Artificial Sequence
<220> FEATURE:
<223> OTHER INFORMATION: VL for mouse and chimeric 1H7

<400> SEQUENCE: 34

```
Glu Ile Val Leu Thr Gln Ser Pro Thr Thr Leu Ala Ala Ser Pro Gly
1               5                   10                  15

Glu Lys Ile Thr Phe Thr Cys Ser Val Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Ser Arg Thr Ser Thr Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Gly Ile Pro
                85                  90                  95

Phe Thr Phe Gly Ser Gly Thr Lys Leu Glu Leu Lys
            100                 105
```

<210> SEQ ID NO 35
<211> LENGTH: 108
<212> TYPE: PRT
<213> ORGANISM: Artificial Sequence
<220> FEATURE:
<223> OTHER INFORMATION: VL for hu1H7-V1 - hu1H7-V12
<220> FEATURE:
<221> NAME/KEY: misc_feature
<222> LOCATION: (72)..(72)
<223> OTHER INFORMATION: Xaa can be Tyr or Phe
<220> FEATURE:
<221> NAME/KEY: misc_feature
<222> LOCATION: (79)..(79)
<223> OTHER INFORMATION: Xaa can Met or Leu

<400> SEQUENCE: 35

```
Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Asn
            20                  25                  30

Tyr Leu His Trp Tyr Gln Gln Lys Pro Gly Leu Ser Pro Arg Leu Leu
        35                  40                  45

Ile Ser Arg Thr Ser Thr Leu Ala Ser Gly Ile Pro Ala Arg Phe Ser
    50                  55                  60

Gly Ser Gly Ser Gly Thr Glu Xaa Thr Leu Thr Ile Ser Arg Xaa Gln
65                  70                  75                  80

Ser Glu Asp Phe Ala Val Tyr Tyr Cys Gln Gln Gly Ser Gly Ile Pro
                85                  90                  95

Phe Thr Phe Gly Gln Gly Thr Lys Leu Glu Ile Lys
            100                 105
```

<210> SEQ ID NO 36
<211> LENGTH: 108
<212> TYPE: PRT
<213> ORGANISM: Artificial Sequence
<220> FEATURE:
<223> OTHER INFORMATION: VL for hu1H7-V1-2

<400> SEQUENCE: 36

```
Glu Ile Val Leu Thr Gln Ser Pro Gly Thr Leu Ser Leu Ser Pro Gly
1               5                   10                  15

Glu Arg Ala Thr Leu Thr Cys Ser Val Ser Ser Ser Ile Ser Ser Asn
            20                  25                  30

Tyr Leu His Trp Tyr Gln Gln Lys Pro Gly Phe Ser Pro Arg Leu Leu
        35                  40                  45

Ile Ser Arg Thr Ser Thr Leu Ala Ser Gly Ile Pro Ala Arg Phe Ser
    50                  55                  60

Gly Ser Gly Ser Gly Thr Ser Tyr Ser Leu Thr Ile Ser Arg Met Gln
65                  70                  75                  80

Ser Glu Asp Phe Ala Val Tyr Tyr Cys Gln Gln Gly Ser Gly Ile Pro
                85                  90                  95

Phe Thr Phe Gly Gln Gly Thr Lys Leu Glu Ile Lys
            100                 105
```

<210> SEQ ID NO 37
<211> LENGTH: 108
<212> TYPE: PRT
<213> ORGANISM: Artificial Sequence
<220> FEATURE:
<223> OTHER INFORMATION: VL for mouse 1F7

<400> SEQUENCE: 37

```
Glu Leu Val Leu Thr Gln Ser Pro Thr Thr Met Ala Ala Ser Pro Gly
1               5                   10                  15

Glu Lys Ile Thr Phe Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Ser Gly Thr Ser Asn Leu Ala Ser Gly Val Pro Pro Arg Phe Ser
    50                  55                  60

Gly Ser Gly Ser Gly Thr Ser Tyr Ser Leu Thr Ile Val Thr Met Glu
65                  70                  75                  80

Ala Glu Asp Val Ala Thr Tyr Tyr Cys Gln Gln Gly Ser Gly Ile Pro
                85                  90                  95

Phe Thr Phe Gly Ser Gly Thr Lys Leu Glu Ile Lys
            100                 105
```

<210> SEQ ID NO 38
<211> LENGTH: 108
<212> TYPE: PRT
<213> ORGANISM: Artificial Sequence
<220> FEATURE:
<223> OTHER INFORMATION: VL for mouse and chimeric 1B5, mouse 1D4, and
      mouse 1G1

<400> SEQUENCE: 38

```
Glu Ile Val Leu Thr Gln Ser Pro Thr Ile Leu Ala Ala Ser Pro Gly
1               5                   10                  15

Glu Lys Ile Thr Phe Thr Cys Ser Val Ser Ser Ser Ile Ser Ser Asn
            20                  25                  30
```

```
Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Gly Ile Pro
                85                  90                  95

Phe Thr Phe Gly Ser Gly Thr Lys Leu Glu Ile Lys
            100                 105


<210> SEQ ID NO 39
<211> LENGTH: 108
<212> TYPE: PRT
<213> ORGANISM: Artificial Sequence
<220> FEATURE:
<223> OTHER INFORMATION: VL for mouse 3C2 and mouse 1A3
<220> FEATURE:
<221> NAME/KEY: misc_feature
<222> LOCATION: (50)..(50)
<223> OTHER INFORMATION: Xaa can be Tyr or Ser
<220> FEATURE:
<221> NAME/KEY: misc_feature
<222> LOCATION: (62)..(62)
<223> OTHER INFORMATION: Xaa can be His or Arg
<220> FEATURE:
<221> NAME/KEY: misc_feature
<222> LOCATION: (82)..(82)
<223> OTHER INFORMATION: Xaa can be Glu or Gly

<400> SEQUENCE: 39

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Xaa Arg Thr Ser Asn Leu Ala Ser Gly Val Pro Thr Xaa Phe Ser
    50                  55                  60

Gly Ser Gly Ser Gly Thr Ser Tyr Ser Leu Thr Ile Gly Thr Met Glu
65                  70                  75                  80

Ala Xaa Asp Val Ala Thr Tyr Tyr Cys Gln Gln Gly Ser Gly Ile Pro
                85                  90                  95

Phe Thr Phe Gly Ser Gly Thr Lys Leu Glu Ile Lys
            100                 105


<210> SEQ ID NO 40
<211> LENGTH: 107
<212> TYPE: PRT
<213> ORGANISM: Artificial Sequence
<220> FEATURE:
<223> OTHER INFORMATION: VL for mouse and chimeric 1H9

<400> SEQUENCE: 40

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Val Trp Tyr Gln Gln Lys Pro Gly Gln Ser Pro Lys Leu Leu Ile
        35                  40                  45

Asn Pro Ala Ser Asn Arg Tyr Thr Gly Val Pro Asp Arg Phe Thr Gly
    50                  55                  60
```

Ser Gly Ser Gly Thr Asp Phe Thr Leu Thr Ile Ser Asn Met Gln Ser
65 70 75 80

Glu Asp Leu Ala Asp Tyr Phe Cys Gln Gln Tyr Ser Ser Tyr Pro Leu
85 90 95

Thr Phe Gly Ala Gly Thr Lys Leu Glu Leu Lys
100 105

<210> SEQ ID NO 41
<211> LENGTH: 330
<212> TYPE: PRT
<213> ORGANISM: Homo sapiens

<400> SEQUENCE: 41

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys 325 330

<210> SEQ ID NO 42
<211> LENGTH: 107
<212> TYPE: PRT
<213> ORGANISM: Homo sapiens

<400> SEQUENCE: 42

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 43
<211> LENGTH: 578
<212> TYPE: PRT
<213> ORGANISM: Artificial Sequence
<220> FEATURE:
<223> OTHER INFORMATION: Human IL6R Fc

<400> SEQUENCE: 43

Leu Ala Pro Arg Arg Cys Pro Ala Gln Glu Val Ala Arg Gly Val Leu
1 5 10 15

Thr Ser Leu Pro Gly Asp Ser Val Thr Leu Thr Cys Pro Gly Val Glu
20 25 30

Pro Glu Asp Asn Ala Thr Val His Trp Val Leu Arg Lys Pro Ala Ala
35 40 45

Gly Ser His Pro Ser Arg Trp Ala Gly Met Gly Arg Arg Leu Leu Leu
50 55 60

Arg Ser Val Gln Leu His Asp Ser Gly Asn Tyr Ser Cys Tyr Arg Ala
65 70 75 80

Gly Arg Pro Ala Gly Thr Val His Leu Leu Val Asp Val Pro Pro Glu
85 90 95

Glu Pro Gln Leu Ser Cys Phe Arg Lys Ser Pro Leu Ser Asn Val Val
100 105 110

Cys Glu Trp Gly Pro Arg Ser Thr Pro Ser Leu Thr Thr Lys Ala Val
115 120 125

Leu Leu Val Arg Lys Phe Gln Asn Ser Pro Ala Glu Asp Phe Gln Glu
130 135 140

Pro Cys Gln Tyr Ser Gln Glu Ser Gln Lys Phe Ser Cys Gln Leu Ala
145 150 155 160

Val Pro Glu Gly Asp Ser Ser Phe Tyr Ile Val Ser Met Cys Val Ala
165 170 175

Ser Ser Val Gly Ser Lys Phe Ser Lys Thr Gln Thr Phe Gln Gly Cys
180 185 190

Gly Ile Leu Gln Pro Asp Pro Pro Ala Asn Ile Thr Val Thr Ala Val
195 200 205

```
Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Ser Val Pro Leu Pro Glu Pro Lys Ser Cys Asp
            340                 345                 350

Lys Thr His Thr Cys Pro Pro Cys Pro Ala Pro Glu Leu Leu Gly Gly
        355                 360                 365

Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
        435                 440                 445

Glu Tyr Lys Cys Lys Val Ser Asn Lys Ala Leu Pro Ala Pro Ile Glu
    450                 455                 460

Lys Thr Ile Ser Lys Ala Lys Gly Gln Pro Arg Glu Pro Gln Val Tyr
465                 470                 475                 480

Thr Leu Pro Pro Ser Arg Glu Glu Met Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
        515                 520                 525

Leu Asp Ser Asp Gly Ser Phe Phe Leu Tyr Ser Lys Leu Thr Val Asp
    530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys
```

<210> SEQ ID NO 44
<211> LENGTH: 356
<212> TYPE: PRT
<213> ORGANISM: Artificial Sequence
<220> FEATURE:
<223> OTHER INFORMATION: Human IL6R-his

<400> SEQUENCE: 44

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Ser Val Pro Leu Pro His His His His His His
            340                 345                 350

His His His His
        355
```

<210> SEQ ID NO 45
<211> LENGTH: 222
<212> TYPE: PRT
<213> ORGANISM: Artificial Sequence
<220> FEATURE:
<223> OTHER INFORMATION: Macaca IL6R-his

<400> SEQUENCE: 45

Met Asn Ser Val Ser Thr Ser Ala Phe Gly Pro Val Ala Phe Ser Leu
1               5                   10                  15

Gly Leu Leu Leu Val Leu Pro Ala Ala Phe Pro Ala Pro Val Leu Pro
            20                  25                  30

Gly Glu Asp Ser Lys Asp Val Ala Ala Pro His Ser Gln Pro Leu Thr
        35                  40                  45

Ser Ser Glu Arg Ile Asp Lys His Ile Arg Tyr Ile Leu Asp Gly Ile
    50                  55                  60

Ser Ala Leu Arg Lys Glu Thr Cys Asn Arg Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Asp Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Glu Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met His His His His His His His His His His
    210                 215                 220

<210> SEQ ID NO 46
<211> LENGTH: 354
<212> TYPE: DNA
<213> ORGANISM: Artificial Sequence
<220> FEATURE:
<223> OTHER INFORMATION: VH for mouse 1H7

<400> SEQUENCE: 46
caggtccaac tgcagcagcc tgggactgaa ctggtgaagc ctggggcttc agtgaaactg 60
tcctgcaagg cttctggcta caccttcacc aactactgga tgcactgggt gaaacagagg 120
cctggacaag gccttgactg gattggagag attaatccta ccaacggtcg tacaaactac 180
aatgagaatt tcaagagtaa ggccacactg actgtagaca aatcctccag cacagcctac 240
atgcaactca gtagcctgac atctgaagac tctgcggtct attactgtgc aagattgaat 300
actcactacg tttttgactc ctggggccaa ggcaccactc tcacactgtc ctca 354

<210> SEQ ID NO 47
<211> LENGTH: 354
<212> TYPE: DNA
<213> ORGANISM: Artificial Sequence
<220> FEATURE:
<223> OTHER INFORMATION: VH for chimeric 1H7

<400> SEQUENCE: 47
caagtgcagc tgcagcagcc cggcacagag ctggtgaaac ccggcgccag cgtgaagctg 60

-continued agctgcaagg ccagcggcta taccttcacc aactactgga tgcactgggt gaagcagaga 120
cccggccaag gactggattg gatcggcgag atcaatccca ccaacggaag aaccaactac 180
aacgagaact tcaagtccaa ggccacactg accgtggaca agagcagcag cacagcctac 240
atgcagctga gctctctgac cagcgaggac tccgccgtgt actactgcgc cagactgaac 300
acccactacg tgttcgacag ctggggccaa ggcaccacac tgacactgtc cagc 354

<210> SEQ ID NO 48
<211> LENGTH: 354
<212> TYPE: DNA
<213> ORGANISM: Artificial Sequence
<220> FEATURE:
<223> OTHER INFORMATION: VH for hu1H7-V5, and hu1H7-V11

<400> SEQUENCE: 48
caagtgcagc tggtgcaaag cggagccgag gtgaaaaagc ccggcgccag cgtgaaggtg 60
agctgcaagg ccagcggcta caccttcacc aactactgga tgcactgggt gagacaagcc 120
cccggccaag gactggagtg gatcggcgag atcaacccta ccaacggaag aaccaactac 180
aacgagaact tcaagtctag agtgacactg accgtggaca cctccacaag caccgtgtac 240
atggagctga gctctctgag atccgaggac accgccgtgt actactgcgc tagactgaac 300
acccactacg tgttcgacag ctggggccaa ggcacactgg tgaccgtgtc ctcc 354

<210> SEQ ID NO 49
<211> LENGTH: 324
<212> TYPE: DNA
<213> ORGANISM: Artificial Sequence
<220> FEATURE:
<223> OTHER INFORMATION: VL for mouse 1H7

<400> SEQUENCE: 49
gaaattgttc tcacccagtc tccaaccacc ttggctgcat ctcccgggga gaagatcact 60
ttcacctgca gtgtcagttc aagtataagt tccaattact tgcattggta tcagcagaag 120
ccaggattct cccctaaact cttgatttct aggacatcca ctctggcttc tggagtccca 180
gctcgcttca gtggcagtgg gtctgggacc tcttactctc tcacaattgg caccatggag 240
gctgaagatg ttgccactta ctactgccag cagggtagtg gtataccatt cacgttcggc 300
tcggggacaa agttggaatt aaaa 324

<210> SEQ ID NO 50
<211> LENGTH: 324
<212> TYPE: DNA
<213> ORGANISM: Artificial Sequence
<220> FEATURE:
<223> OTHER INFORMATION: VL for chimeric 1H7

<400> SEQUENCE: 50
gagatcgtgc tgacccagag ccctacaaca ctggctgcca gccccggcga gaagatcacc 60
ttcacatgca gcgtgagcag cagcatcagc tccaattatc tgcactggta tcagcagaag 120
cccggcttca gccccaaact gctgatctct agaaccagca cactggcttc cggcgtgccc 180
gccagatttt ccggcagcgg aagcggcacc agctactctc tgaccattgg caccatggag 240
gccgaggatg tggccaccta ctactgccag caaggctccg gcattccctt caccttcggc 300
agcggcacca agctggagct gaag 324

<210> SEQ ID NO 51
<211> LENGTH: 324

<212> TYPE: DNA
<213> ORGANISM: Artificial Sequence
<220> FEATURE:
<223> OTHER INFORMATION: VL for hu1H7-V1 - hu1H7-V6

<400> SEQUENCE: 51
gagatcgtgc tgacccagag ccccggcaca ctgtctctga gccccggcga gagagccaca 60
ctgagctgca gcgtgagcag cagcatcagc agcaactatc tgcactggta tcagcagaag 120
cccggactga gccctagact gctgatctct agaacctcca cactggccag cggcatcccc 180
gccagattta gcggaagcgg aagcggcacc gagtacacac tgaccatctc tagaatgcag 240
agcgaggact tcgccgtgta ctactgccag caaggcagcg gaatcccctt caccttcggc 300
caaggcacca agctggagat caag 324

<210> SEQ ID NO 52
<211> LENGTH: 993
<212> TYPE: DNA
<213> ORGANISM: Artificial Sequence
<220> FEATURE:
<223> OTHER INFORMATION: Heavy chain constant region

<400> SEQUENCE: 52
gctagcacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa tga 993

<210> SEQ ID NO 53
<211> LENGTH: 324
<212> TYPE: DNA
<213> ORGANISM: Artificial Sequence
<220> FEATURE:
<223> OTHER INFORMATION: Light chain constant region

<400> SEQUENCE: 53
cgtacggtgg cggcgccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180

```
agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg ttga                                           324


<210> SEQ ID NO 54
<211> LENGTH: 448
<212> TYPE: PRT
<213> ORGANISM: Artificial Sequence
<220> FEATURE:
<223> OTHER INFORMATION: Heavy chain of Tocilizumab

<400> SEQUENCE: 54

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 55
<211> LENGTH: 214
<212> TYPE: PRT
<213> ORGANISM: Artificial Sequence
<220> FEATURE:
<223> OTHER INFORMATION: Light chain of Tocilizumab

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 56
<211> LENGTH: 118
<212> TYPE: PRT
<213> ORGANISM: Artificial Sequence
<220> FEATURE:
```

<223> OTHER INFORMATION: VH for hu1H7-V1, and hu1H7-V7

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Lys Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: VH for hu1H7-V5, and hu1H7-V11

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: VH for mouse 1D4

<400> SEQUENCE: 58

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Val Arg Pro Gly Gln Gly Leu Glu Trp Ile

```
        35                  40                  45

Gly Glu Ile Asn Pro Thr Asn Gly Arg Thr Asn Tyr Asn Glu Asp Phe
    50                  55                  60

Lys Ser Lys Ala Thr Leu Thr Val Asn Ser Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Asn Thr His Tyr Val Phe Asp Tyr Trp Gly Gln Gly Thr
            100                 105                 110

Thr Leu Thr Val Ser Ser
        115


<210> SEQ ID NO 59
<211> LENGTH: 108
<212> TYPE: PRT
<213> ORGANISM: Artificial Sequence
<220> FEATURE:
<223> OTHER INFORMATION: VL for hu1H7-V1 - hu1H7-V6

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Asn
            20                  25                  30

Tyr Leu His Trp Tyr Gln Gln Lys Pro Gly Leu Ser Pro Arg Leu Leu
        35                  40                  45

Ile Ser Arg Thr Ser Thr Leu Ala Ser Gly Ile Pro Ala Arg Phe Ser
    50                  55                  60

Gly Ser Gly Ser Gly Thr Glu Tyr Thr Leu Thr Ile Ser Arg Met Gln
65                  70                  75                  80

Ser Glu Asp Phe Ala Val Tyr Tyr Cys Gln Gln Gly Ser Gly Ile Pro
                85                  90                  95

Phe Thr Phe Gly Gln Gly Thr Lys Leu Glu Ile Lys
            100                 105


<210> SEQ ID NO 60
<211> LENGTH: 108
<212> TYPE: PRT
<213> ORGANISM: Artificial Sequence
<220> FEATURE:
<223> OTHER INFORMATION: VL for mouse 1A3

<400> SEQUENCE: 60

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Ser Arg Thr Ser Asn Leu Ala Ser Gly Val Pro Thr Arg Phe Ser
    50                  55                  60

Gly Ser Gly Ser Gly Thr Ser Tyr Ser Leu Thr Ile Gly Thr Met Glu
65                  70                  75                  80

Ala Gly Asp Val Ala Thr Tyr Tyr Cys Gln Gln Gly Ser Gly Ile Pro
                85                  90                  95

Phe Thr Phe Gly Ser Gly Thr Lys Leu Glu Ile Lys
            100                 105
```

<210> SEQ ID NO 61
<211> LENGTH: 118
<212> TYPE: PRT
<213> ORGANISM: Artificial Sequence
<220> FEATURE:
<223> OTHER INFORMATION: VH for hu1H7-V4, and hu1H7-V10

<400> SEQUENCE: 61

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asn Pro Thr Asn Gly Arg Thr Asn Tyr Asn Glu Asn Phe
    50                  55                  60

Lys Ser Lys Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115
```

<210> SEQ ID NO 62
<211> LENGTH: 118
<212> TYPE: PRT
<213> ORGANISM: Artificial Sequence
<220> FEATURE:
<223> OTHER INFORMATION: VH for hu1H7-V6, and hu1H7-V12

<400> SEQUENCE: 62

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Lys Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115
```

<210> SEQ ID NO 63
<211> LENGTH: 118
<212> TYPE: PRT
<213> ORGANISM: Artificial Sequence
<220> FEATURE:
<223> OTHER INFORMATION: VH for hu1H7-V2, and hu1H7-V8

<400> SEQUENCE: 63

```
Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Lys Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115


<210> SEQ ID NO 64
<211> LENGTH: 118
<212> TYPE: PRT
<213> ORGANISM: Artificial Sequence
<220> FEATURE:
<223> OTHER INFORMATION: VH for hu1H7-V3, and hu1H7-V9

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Glu Ile Asn Pro Thr Asn Gly Arg Thr Asn Tyr Asn Glu Asn Phe
    50                  55                  60

Lys Ser Lys Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asn Thr His Tyr Val Phe Asp Ser Trp Gly Gln Gly Thr
            100                 105                 110

Leu Val Thr Val Ser Ser
        115


<210> SEQ ID NO 65
<211> LENGTH: 118
<212> TYPE: PRT
<213> ORGANISM: Artificial Sequence
<220> FEATURE:
<223> OTHER INFORMATION: VH for mouse 1G1

<400> SEQUENCE: 65

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Val Arg Pro Gly Gln Gly Leu Glu Trp Ile
        35                  40                  45

Gly Glu Ile Asn Pro Thr Asn Gly Arg Thr Asn Tyr Asn Glu Asp Phe
    50                  55                  60
```

-continued

Lys Ser Lys Ala Thr Leu Thr Val Glu Ser Ser Ser Ser Thr Ala Tyr
65 70 75 80

Met Gln Phe Ser Ser Leu Thr Ser Glu Asp Ser Ala Val Tyr Tyr Cys
85 90 95

Ala Arg Leu Asn Thr His Tyr Val Phe Asp Tyr Trp Gly Gln Gly Thr
100 105 110

Thr Leu Thr Val Ser Ser
115

<210> SEQ ID NO 66
<211> LENGTH: 108
<212> TYPE: PRT
<213> ORGANISM: Artificial Sequence
<220> FEATURE:
<223> OTHER INFORMATION: VL for hu1H7-V7 - hu1H7-V12

<400> SEQUENCE: 66

Glu Ile Val Leu Thr Gln Ser Pro Gly Thr Leu Ser Leu Ser Pro Gly
1 5 10 15

Glu Arg Ala Thr Leu Ser Cys Ser Val Ser Ser Ser Ile Ser Ser Asn
20 25 30

Tyr Leu His Trp Tyr Gln Gln Lys Pro Gly Leu Ser Pro Arg Leu Leu
35 40 45

Ile Ser Arg Thr Ser Thr Leu Ala Ser Gly Ile Pro Ala Arg Phe Ser
50 55 60

Gly Ser Gly Ser Gly Thr Glu Phe Thr Leu Thr Ile Ser Arg Leu Gln
65 70 75 80

Ser Glu Asp Phe Ala Val Tyr Tyr Cys Gln Gln Gly Ser Gly Ile Pro
85 90 95

Phe Thr Phe Gly Gln Gly Thr Lys Leu Glu Ile Lys
100 105

<210> SEQ ID NO 67
<211> LENGTH: 108
<212> TYPE: PRT
<213> ORGANISM: Artificial Sequence
<220> FEATURE:
<223> OTHER INFORMATION: VL for mouse 3C2

<400> SEQUENCE: 67

Glu Ile Val Leu Thr Gln Ser Pro Thr Thr Met Ala Ala Ser Pro Gly
1 5 10 15

Glu Lys Ile Thr Ile Thr Cys Ser Ala Ser Ser Ser Ile Ser Ser Asn
20 25 30

Tyr Leu His Trp Tyr Gln Gln Lys Pro Gly Phe Ser Pro Lys Leu Leu
35 40 45

Ile Tyr Arg Thr Ser Asn Leu Ala Ser Gly Val Pro Thr His Phe Ser
50 55 60

Gly Ser Gly Ser Gly Thr Ser Tyr Ser Leu Thr Ile Gly Thr Met Glu
65 70 75 80

Ala Glu Asp Val Ala Thr Tyr Tyr Cys Gln Gln Gly Ser Gly Ile Pro
85 90 95

Phe Thr Phe Gly Ser Gly Thr Lys Leu Glu Ile Lys
100 105